US012123882B2

(12) United States Patent
Anderberg et al.

(10) Patent No.: US 12,123,882 B2
(45) Date of Patent: *Oct. 22, 2024

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Encinitas, CA (US); James Patrick Kampf, San Diego, CA (US)

(73) Assignee: ASTUTE MEDICAL, INC., San Diego, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/681,493

(22) Filed: Feb. 25, 2022

(65) Prior Publication Data
US 2022/0187319 A1 Jun. 16, 2022

Related U.S. Application Data

(63) Continuation of application No. 15/676,828, filed on Aug. 14, 2017, now Pat. No. 11,262,363, which is a continuation of application No. 13/517,244, filed as application No. PCT/US2010/061377 on Dec. 20, 2010, now Pat. No. 10,830,773.

(60) Provisional application No. 61/410,875, filed on Nov. 6, 2010, provisional application No. 61/410,878, filed on Nov. 6, 2010, provisional application No. 61/410,880, filed on Nov. 6, 2010, provisional application No. 61/410,879, filed on Nov. 6, 2010, provisional application No. 61/308,861, filed on Feb. 26, 2010, provisional application No. 61/288,327, filed on Dec. 20, 2009.

(51) Int. Cl.
*G01N 33/68* (2006.01)
(52) U.S. Cl.
CPC ... *G01N 33/6893* (2013.01); *G01N 2800/347* (2013.01); *G01N 2800/52* (2013.01)
(58) Field of Classification Search
CPC .................................. G01N 2800/347
See application file for complete search history.

(56) References Cited

U.S. PATENT DOCUMENTS

| | | |
|---|---|---|
| 5,118,614 A | 6/1992 | Rybák et al. |
| 5,324,634 A | 6/1994 | Zucker |
| 5,480,792 A | 1/1996 | Buechler |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler et al. |
| 6,140,045 A | 10/2000 | Wohlstadter et al. |
| 6,143,576 A | 11/2000 | Buechler |
| 6,218,122 B1 | 4/2001 | Friend et al. |

(Continued)

FOREIGN PATENT DOCUMENTS

| | | |
|---|---|---|
| CN | 1791797 | 6/2006 |
| EP | 0828159 | 3/1998 |

(Continued)

OTHER PUBLICATIONS

Kutsukake et al. Reproductive Biology Endocrinology. 2008; 6(54): 1-6 (Year: 2008).*
Abd El Latif et al., "Urinary Epidermal Growth Factor Excretion: A Useful Prognostic Marker for Progression of Renal Damage in Children," J Med Sci, Oct. 1, 2007, 7(7):1171-1176.
Abou-Shousha et al., "Interleukin-2 Regulatory Effect on P-Selectin and Interleukin-8 Production in Patients with Chronic Renal Failure," Egypt J Immunol, 2006, 13(1):11-18.

(Continued)

*Primary Examiner* — Vanessa L. Ford
*Assistant Examiner* — Sandra Carter
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using a plurality of assays, one or more of which is configured to detect a kidney injury marker selected from the group consisting of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 as diagnostic and prognostic biomarkers in renal injuries.

20 Claims, No Drawings

(56) References Cited

U.S. PATENT DOCUMENTS

| | | |
|---|---|---|
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,623,910 B2 | 11/2009 | Couderc et al. |
| 7,662,578 B2 | 2/2010 | Devarajan |
| 7,833,699 B2 | 11/2010 | Locht et al. |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 8,778,615 B2 | 7/2014 | Anderberg et al. |
| 8,993,250 B2 | 3/2015 | Anderberg et al. |
| 9,029,093 B2 | 5/2015 | Anderberg et al. |
| 9,057,735 B2 | 6/2015 | Anderberg et al. |
| 9,229,010 B2 | 1/2016 | Anderberg et al. |
| 9,360,488 B2 | 6/2016 | Anderberg et al. |
| 9,459,261 B2 | 10/2016 | Anderberg et al. |
| 9,696,322 B2 | 7/2017 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | McPherson et al. |
| 11,099,194 B2 | 8/2021 | Anderberg et al. |
| 2002/0012906 A1 | 1/2002 | Comper |
| 2002/0055627 A1 | 5/2002 | Rosen et al. |
| 2003/0003588 A1 | 1/2003 | Comper |
| 2003/0157580 A1 | 8/2003 | Hochstrasser et al. |
| 2003/0186308 A1 | 10/2003 | Young et al. |
| 2004/0053309 A1 | 3/2004 | Holt et al. |
| 2004/0106155 A1 | 6/2004 | Comper |
| 2004/0126767 A1 | 7/2004 | Anderberg et al. |
| 2004/0253637 A1 | 12/2004 | Buechler et al. |
| 2005/0002934 A1 | 1/2005 | Reed |
| 2005/0048033 A1 | 3/2005 | Fraser et al. |
| 2005/0084880 A1 | 4/2005 | Duman et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2006/0257903 A1 | 11/2006 | Akil et al. |
| 2007/0031905 A1 | 2/2007 | Shariat |
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0184439 A1 | 8/2007 | Guilford et al. |
| 2007/0248989 A1 | 10/2007 | Devarajan |
| 2007/0249002 A1* | 10/2007 | Hu .................. G01N 33/57442 435/7.92 |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0090759 A1 | 4/2008 | Kokenyesi et al. |
| 2008/0090765 A1 | 4/2008 | Schmidt-Ott et al. |
| 2008/0133141 A1 | 6/2008 | Frost |
| 2008/0153092 A1 | 6/2008 | Kienle et al. |
| 2008/0166717 A1 | 7/2008 | Thorin |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0004687 A1 | 1/2009 | Mansfield et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0130693 A1 | 5/2009 | Bassi et al. |
| 2009/0148539 A1 | 6/2009 | Elias et al. |
| 2009/0176656 A1 | 7/2009 | Halloran |
| 2009/0179287 A1 | 7/2009 | Inaba |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0240081 A1 | 9/2010 | Rollinger et al. |
| 2010/0267041 A1 | 10/2010 | Shuber et al. |
| 2010/0267061 A1 | 10/2010 | Hsieh et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0135427 A1 | 5/2012 | Kypros et al. |
| 2012/0156701 A1 | 6/2012 | Anderberg et al. |
| 2012/0190044 A1 | 7/2012 | Anderberg et al. |
| 2012/0190051 A1 | 7/2012 | Anderberg et al. |
| 2012/0208717 A1 | 8/2012 | Hu et al. |
| 2012/0283128 A1 | 11/2012 | Anderberg et al. |
| 2012/0329071 A1 | 12/2012 | Chance et al. |
| 2013/0035290 A1 | 2/2013 | Elias et al. |
| 2013/0157881 A1 | 6/2013 | Anderberg et al. |
| 2013/0210043 A1 | 8/2013 | Anderberg et al. |
| 2014/0213477 A1 | 7/2014 | Anderberg et al. |
| 2014/0315734 A1 | 10/2014 | Arnold et al. |
| 2014/0323594 A1 | 10/2014 | Anderberg et al. |
| 2014/0343600 A1 | 11/2014 | Leschinsky |
| 2014/0356301 A1 | 12/2014 | Shyur et al. |
| 2014/0377777 A1 | 12/2014 | Anderberg et al. |
| 2015/0233946 A1 | 8/2015 | Block et al. |
| 2016/0146832 A1 | 5/2016 | Chawla et al. |
| 2017/0248613 A1 | 8/2017 | Anderberg et al. |
| 2018/0074054 A1 | 3/2018 | McPherson et al. |
| 2019/0263926 A1 | 8/2019 | McPherson et al. |

FOREIGN PATENT DOCUMENTS

| | | |
|---|---|---|
| EP | 1777523 | 4/2007 |
| EP | 1905846 | 4/2008 |
| EP | 2261660 | 12/2010 |
| EP | 2480882 | 8/2012 |
| EP | 2513649 | 10/2012 |
| JP | 2003-081838 | 3/2003 |
| JP | 2006-038877 | 2/2006 |
| JP | 2008-508502 | 3/2008 |
| JP | 2008-527977 | 7/2008 |
| JP | 2009-524029 | 6/2009 |
| JP | 5998057 | 11/2016 |
| RU | 2180965 | 3/2002 |
| SU | 1429031 | 10/1988 |
| WO | WO 1998/055508 | 12/1998 |
| WO | WO 2003/054004 | 7/2003 |
| WO | WO 2003/075016 | 9/2003 |
| WO | WO 2004/005934 | 1/2004 |
| WO | WO 2004/059293 | 7/2004 |
| WO | WO 2005/087264 | 9/2005 |
| WO | WO 2006/010529 | 2/2006 |
| WO | WO 2006/072654 | 7/2006 |
| WO | WO 2006/083986 | 8/2006 |
| WO | WO 2007/013919 | 2/2007 |

(56) References Cited

FOREIGN PATENT DOCUMENTS

| WO | WO 2007/041623 | 4/2007 |
|---|---|---|
| WO | WO 2007/082586 | 7/2007 |
| WO | WO 2007/124331 | 11/2007 |
| WO | WO 2007/124419 | 11/2007 |
| WO | WO 2008/060607 | 5/2008 |
| WO | WO 2008/067065 | 6/2008 |
| WO | WO 2008/084331 | 7/2008 |
| WO | WO 2008/089994 | 7/2008 |
| WO | WO 2008/104804 | 9/2008 |
| WO | WO 2008/116867 | 10/2008 |
| WO | WO 2008/122670 | 10/2008 |
| WO | WO 2008/154238 | 12/2008 |
| WO | WO 2009/038742 | 3/2009 |
| WO | WO 2009/062520 | 5/2009 |
| WO | WO 2010/025424 | 3/2010 |
| WO | WO 2010/025434 | 3/2010 |
| WO | WO 2010/045714 | 4/2010 |
| WO | WO 2010/048346 | 4/2010 |
| WO | WO 2010/048347 | 4/2010 |
| WO | WO 2010/054389 | 5/2010 |
| WO | WO 2010/091236 | 8/2010 |
| WO | WO 2010/111746 | 10/2010 |
| WO | WO 2010/128158 | 11/2010 |
| WO | WO 2011/017614 | 2/2011 |
| WO | WO 2011/025917 | 3/2011 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/070935 | 5/2014 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/060525 | 4/2017 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Akcay et al., "Mediators of Inflammation in Acute Kidney Injury," Mediators Inflamm, 2009, 2009: 137072 (12 pp).

Albright, "Acute Renal Failure: A Practical Update," Mayo Clin Proc, 2001, 76(1):67-74.

Altom et al., "Optimizing enzyme-linked immunosorbent assays on automated 96-well plate robotic systems," Laboratory Robotics and Automation, 1990, 2(3):139-146 (abstract only).

Amemiya et al., "Insulin like growth factor binding protein-7 reduces growth of human breast cancer cells and xenografted tumors," Breast Cancer Res Treat, May 2010 (pub online), 126(2):373-384.

Anders et al., "Chemokines and chemokine receptors are involved in the resolution or progression of renal disease," Kidney Int, Feb. 2003, 63(2):401-415.

Anilkumar et al., "Trimeric assembly of the C-terminal region of Thrombospondin-1 or Thrombospondin-2 is necessary for cell spreading and fascin spike organization," J Cell Sci, Jun. 2002, 115(Pt 11):2357-2366.

Aregger et al., "Identification of IGFBP-7 by urinary proteomics as a novel prognostic marker in early acute kidney injury," Kidney International, Sep. 2013 (pub online, 85(4):909-919.

Arribas et al., "ADAM17 as a Therapeutic Target in Multiple Diseases," Curr Pharm Des, 2009, 15(20):2319-2335.

Arrizabalaga et al., "Tubular and Interstitial Expression of ICAM-1 as a Marker of Renal Injury in IgA Nephropathy," Am J Nephrol, Jan. 2003 (Epub), 23(3):121-128.

Bagshaw et al., "A multi-centre evaluation of the RIFLE criteria for early acute kidney injury in critically ill patients," Nephrol Dial Transplant, Oct. 2007 (advance access pub), 23(4):1203-1210.

Bagshaw et al., "Urinary biomarkers in septic acute kidney injury," Intensive Care Med, 2007, 33(7):1285-1296.

Bajwa et al., "Immune Mechanisms and Novel Pharmacological Therapies of Acute Kidney Injury," Curr Drug Targets, 2009, 10(12):1196-1204.

Barrera-Chimal et al., "Hsp72 is an early and sensitive biomarker to detect acute kidney injury," EMBO Mol Med, 2011, 3(1):5-20.

Basile et al., "Renal ischemia reperfusion inhibits VEGF expression and induces ADAMTS-1, a novel VEGF inhibitor," Am J Physiol Renal Physiol, Feb. 6, 2008, 294(4):F928-F936.

Basu et al., "Identification of candidate serum biomarkers for severe septic shock-associated kidney injury via microarray," Crit Care, 2011, 15(6):R273.

Bellomo et al., "Acute renal failure—definition, outcome measures, animal models, fluid therapy and information technology needs: the Second International Consensus Conference of the Acute Dialysis Quality Initiative (ADQI) Group," Crit Care, 2004, 8(4):R204-R212.

Bennett et al., "Chronic cyclosporine nephropathy: The Achilles' heel of immunosuppressive therapy," Kidney Int., 1996, 50(4):1089-1100.

Berahovich et al., "Proteolytic Activation of Alternative CCR1 Ligands in Inflammation," J Immunol, Jun. 2005, 174(11):7341-7351.

Beushausen, "NWG Biomarker Objectives," ILSI Health and Environmental Sciences Institute, ILSI-HESI Annual Meeting, 2006, 17 pp.

Bicik et al., "Role of Transforming Growth Factor-beta2 in, and a Possible Transforming Growth Factor-beta2 Gene Polymorphism as a Marker of, Renal Dysfunction in Essential Hypertension: A Study in Turkish Patients," Current Therapeutic Research, Jul./Aug. 2005, 66(4):266-278.

Bihorac et al., "Validation of Cell-Cycle Arrest Biomarkers for Acute Kidney Injury Using Clinical Adjudication," Am J Respir Crit Care Med., Apr. 15, 2014, 189(8):932-939. doi: 10.1164/rccm.201401-00770C.

Biotrin International, "Biotrin Biomarkers: How late do you want to detect preclinical kidney damage?," Biotrin's acute kidney injury test (AKI Test), Biotrin's Preclinical Kidney Biomarkers, 8 pp.

Bone et al., "Definitions for Sepsis and Organ Failure and Guidelines for the Use of Innovative Therapies in Sepsis," American College of Chest Physicians/Society of Critical Care Medicine, Jun. 1992, 101(6):1644-55.

Bonomini et al., "Serum Levels of Soluble Adhesion Molecules in Chronic Renal Failure and Dialysis Patients," Nephron, 1998, 79(4):399-407.

Bonventre, "Dedifferentiation and Proliferation of Surviving Epithelial Cells in Acute Renal Failure," J Am Soc Nephrol, 2003, 14(Suppl 1):S55-S61.

Bonventre, "Pathophysiology of Acute Kidney Injury: Roles of Potential Inhibitors of Inflammation," Contrib Nephrol, 2007, 156:39-46.

Bonventre et al., "Ischemic acute renal failure: An inflammatory disease?," Kidney Int, Aug. 2004, 66(2):480-485.

Burne et al., "IL-1 and TNF independent pathways mediate ICAM-1/VCAM-1 up-regulation in ischemia reperfusion injury," J Leukoc Biol, Aug. 2001, 70(2):192-198.

Burne-Taney et al., "The role of adhesion molecules and T cells in ischemic renal injury," Curr Opin Nephrol Hypertens, 2003, 12(1):85-90.

Cai, "Detection and Application for the biomarker of Rental Injury in Early Stage." Laboratory Med Clinic. Jun. 2005;2(3):124-127—with English translation.

Calabrese et al., "Oxidative stress and cellular stress response in diabetic nephropathy," Cell Stress & Chaperones, 2007, 12(4):299-306—Accession No. XP002705326.

(56) References Cited

OTHER PUBLICATIONS

Canani et al., "The Fatty Acid-Binding Protein-2 A54T Polymorphism is Associated With Renal Disease in Patients With Type 2 Diabetes," Diabetes, Nov. 2005, 54(11):3326-3330.
Caron et al., "Ischemic injury alters endothelial cell properties of kidney cortex: Stimulation of MMP-9," Exp Cell Res., Oct. 15, 2005, 301(1):105-116.
Catania et al., "Role of matrix metalloproteinases in renal pathophysiologies," Am J Physiol Renal Physiol, 2007, 292(3):F905-F911.
Chawla et al., "Identifying critically ill patients at high risk for developing acute renal failure: A pilot study," Kidney Int., 2005, 68(5):2274-2280.
Chertow et al., "Acute Kidney Injury, Mortality, Length of Stay, and Costs in Hospitalized Patients," J Am Soc Nephrol, 2005, 16(11):3365-3370.
Chindarkar et al., "Reference intervals of urinary acute kidney injury (AKI) markers [IGFBP7]•[TIMP2] in apparently healthy subjects and chronic comorbid subjects without AKI," Clinica Chimica Acta, 2016, 452:32-37.
Choi et al., "Expression of Vascular Endothelial Growth Factor-C and its Receptor mRNA in the Rat Kidney with Ischemia-Reperfusion Injury," Clinical Kidney J, Jun. 2, 2011, 4(S2):2 pp.
Christenson et al., "Standardization of Cardiac Troponin I Assays: Round Robin of Ten Candidate Reference Materials," Clinical Chemistry, 2001, 47(3):431-437.
Coca et al., "Biomarkers for the diagnosis and risk stratification of acute kidney injury: A systematic review," Kidney Int, May 2008, 73(9):1008-1016.
Coca et al., "Urinary Biomarkers for Acute Kidney Injury: Perspectives on Translation," Clin J Am Soc Nephrol, 2008, 3:481-490.
Constantin et al., "Plasma neutrophil gelatinase-associated lipocalin is an early marker of acute kidney injury in adult critically ill patients: A prospective study," J Crit Care, 2010, 25(1):176.e1-176.e6.
Cooper, "Effect of tobacco smoking on renal function," Indian J Med Res, Sep. 2006, 124(3):261-268.
Cottone et al., "Endothelin-1 and F2-isoprostane relate to and predict renal dysfunction in hypertensive patients," Nephrol Dial Transpl, Feb. 2009, 24(2):497-503.
Cruz et al., North East Italian Prospective Hospital Renal Outcome Survey on Acute Kidney Injury (NEiPHROS-AKI): Targeting the Problem with the RIFLE Criteria, Clin J Amer Soc Nephrol, 2007, 2(3):418-425.
Cutillas et al., "The urinary proteome in Fanconi syndrome implies specificity in the reabsorption of proteins by renal proximal tubule cells," Am J Physiol Renal Physio, 2004, 287(3):F353-F364.
Cwirla et al., "Peptides on phage: A vast library of peptides for identifying ligands," Proc Natl Acad Sci USA, 1990, 87(16):6378-6382.
Daemen et al., "Apoptosis and Chemokine Induction After Renal Ischemia-Reperfusion," Transplantation, Apr. 15, 2001, 71(7):1007-1011.
Daha et al., "Is the proximal tubular cell a proinflammatory cell?," Nephrol Dial Transplant, 2000, 15(Suppl 6):41-43.
De Sá et al., "Leukocyte, Platelet and Endothelial Activation in Patients with Acute Renal Failure Treated by Intermittent Hemodialysis," Am J Nephrol, 2001, 21(4):264-273.
Devarajan, "Cellular and molecular derangements in acute tubular necrosis," Curr Opin Pediatr, 2005, 17(2):193-199.
Devarajan, "Novel biomarkers for the early prediction of acute kidney injury," Cancer Therapy, 2005, 3:477-488.
Devarajan, "Update on Mechanisms of Ischemic Acute Kidney Injury," J Am Soc Nephrol, 2006, 17(6):1503-1520.
Devarajan et al., "Proteomics for Biomarker Discovery in Acute Kidney Injury," Semin Nephrol, Nov. 2007, 27(6):637-651.
Devlin et al., "Random Peptide Libraries: A Source of Specific Protein Binding Molecules," Science, Jul. 27, 1990, 249(A967):404-406.
Domanski et al., "Purine and Cytokine Concentrations in the Renal Vein of the Allograft During Reperfusion," Transplant Proc, 2007, 39(5):1319-1322.
Edelstein, "Biomarkers of Acute Kidney Injury," Adv Chronic Kidney Dis., Jul. 2008, 15(3)222-234.
Endo et al., "Matrix metalloproteinase-2, matrix metalloproteinase-9, and tissue inhibitor of metalloproteinase-1 in the peripheral blood of patients with various glomerular diseases and their implication in pathogenetic lesions: study based on an enzyme-linked assay and immunohistochemical staining," Clin Exp Nephrol, Dec. 2006, 10(4):253-261.
Etzioni et al., "Combining biomarkers to detect disease with application to prostate cancer," Biostatistics, 2003, 4(4):523-538.
FDA, "European Medicines Agency to Consider Additional Test Results When Assessing New Drug Safety—Collaborative effort by FDA and EMEA expected to yield additional safety data," Jun. 12, 2008, http://www.natap.org/2008/ newsUpdates/071608_01.htm.
FDA News Release, U.S. Food and Drug Administration, FDA allows marketing of the first test to assess risk of developing acute kidney injury, N.p., Sep. 5, 2014, Web. Oct. 22, 2014 <http://www.fda.gov/NewsEvents/Newsroom/PressAnnouncements/ucm4 . . . >.
Ferguson et al., "Biomarkers of nephrotoxic acute kidney injury," Toxicology, 2008, 245(3):182-193.
Fischer et al., "A readers' guide to the interpretation of diagnostic test properties: clinical example of sepsis," Intensive Care Med, 2003, 29:1043-1051.
Flynn et al., "Urinary excretion of beta2-glycoprotein-1 (apolipoprotein H) and other markers of tubular malfunction in "non-tubular" renal disease," J Clin Pathol, 1992, 45(7):561-567.
Frangogiannis, "Chemokines in ischemia and reperfusion," Thromb Haemost, 2007, 97(5):738-747.
Fried et al., "Inflammatory and Prothrombotic Markers and the Progression of Renal Disease in Elderly Individuals," J Am Soc Nephrol, Dec. 2004, 15(12):3184-3191.
Fu et al., Study on the expression of VEGF, MMP-2 and TIMP-2 in the progression of IgA nephropathy, J Clin Exp Pathol, Oct. 24, 2008, 24(5):573-576.
Fujisaki et al., "Infusion of radiocontrast agents induces exaggerated release of urinary endothelin in patients with impaired renal function," Clin Exp Nephrol, Dec. 2003, 7(4):279-283.
Furuichi et al., "Chemokine/chemokine receptor-mediated inflammation regulates pathologic changes from acute kidney injury to chronic kidney disease," Clin Exp Nephrol, 2009, 13(1):9-14.
Furuichi et al., "Roles of chemokines in renal ischemia/reperfusion injury," Front Biosci, May 1, 2008, 13:4021-4028.
Galkina et al., "Leukocyte Recruitment and Vascular Injury in Diabetic Nephropathy," J Am Soc Nephrol, 2006, 17(2):368-377.
Garcia et al., "Adenosine A2A receptor activation and macrophage-mediated experimental glomerulonephritis," FASEB J, 2008, 22(2):445-454.
Gbadegesin et al., "Plasma and urinary soluble adhesion molecule expression is increased during first documented acute pyelonephritis," Arch Dis Child, 2002, 86(3):218-221.
Gocze et al., "Urinary Biomarkers TIMP-2 and IGFBP7 Early Predict Acute Kidney Injury after Major Surgery," PLoS One, Mar. 23, 2015, DOI:10.1371/journal.pone.0120863, pp. 1-11.
Goes et al., "Effect of Recombinant Human Insulin-Like Growth Factor-1 on the Inflammatory Response to Acute Renal Injury," J Am Soc Nephrol, 1996, 7(5):710-720.
Goldstein et al., "Renal Angina," Clin J Am Soc Nephrol, 2010, 5(5):943-949.
Grigoryev et al., "The Local and Systemic Inflammatory Transcriptome after Acute Kidney Injury," J Am Soc Nephrol, 2008, 19(3):547-558.
Gümüs et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001, 27(2):133-135.
Gupta et al., "Role of Protein C in Renal Dysfunction after Polymicrobial Sepsis," J Am Soc Nephrol., Mar. 18, 2007, (3):860-867.

(56) References Cited

OTHER PUBLICATIONS

Haase et al., "A comparison of the RIFLE and Acute Kidney Injury Network classifications for cardiac surgery-associated acute kidney injury: A prospective cohort study," J Thorac Cardiovasc Surg, Dec. 2009, 138(6):1370-1376.
Han, "Biomarkers for Early Detection of Acute Kidney Injury," Nephrology Rounds, Apr. 2008, 6(4):6 pp.
Han et al., "Urinary Biomarkers in the Early Diagnosis of Acute Kidney Injury after Cardiac Surgery," Clin J Am Soc Nephrol, 2009, 4:873-882.
Han et al., "Upregulation of hyaluronan and its binding receptors in an experimental model of chronic cyclosporine nephropathy," Nephrology, 2010, 15(2):216-224.
Han et al., "Urinary biomarkers in the early diagnosis of acute kidney injury," Kidney Int, 2008, 73(7):863-869.
Hanley et al., "The Meaning and Use of the Area under a Receiver Operating Characteristic (ROC) Curve," Radiology, Apr. 1982, 143:29-36.
Harpur et al., "Biological Qualification of Biomarkers of Chemical-Induced Renal Toxicity in Two Strains of Male Rat," Toxicol Sci., Aug. 2011, 122(2):235-252.
Harris et al., "Growth Factors and Cytokines in Acute Renal Failure," Adv Ren Replace Ther, Apr. 1997, 4(2 Suppl):43-53.
Hatta et al., "Cytokine Array Comparisons of Plasma from Cycling Fertile Women on Cycle Day 5 and Ovulation," Am J Reprod Immunol, Sep. 2009, 62(3):158-164.
He et al., "A research on serum, urine and tumor tissue hyaluronate assays for detecting malignant ovarian tumors," Zhonghua Fu Chan Ke Za Zhi, Mar. 1995, 30(3):161-163—Abstract only.
He et al., "Interleukin-18 binding protein transgenic mice are protected against ischemic acute kidney injury," Am J Physiol Renal Physiol, 2008, 295(5):F1414-F1421.
Healy et al., "Apoptosis and necrosis: Mechanisms of cell death induced by cyclosporine A in a renal proximal tubular cell line," Kidney Int, 1998, 54:1955-1966.
Herget-Rosenthal et al., "Early detection of acute renal failure by serum cystatin C," Kidney Int, 2004, 66(3):1115-1122.
Hidaka et al., "Urinary clusterin levels in the rat correlate with the severity of tubular damage and may help to differentiate between glomerular and tubular injuries," Cell Tissue Res, 2002, 310(3):289-296.
Hirai et al., "Plasma Endothelin-1(ET-1) is a Useful Marker for Renal Dysfunction," Atheroscler Suppl., Jun. 19, 2006, 7(3):60[Mo-P1:65].
Hirschberg et al., "Factors Predicting Poor Outcome in Patients with Acute Renal Failure (ARF)," J Am Soc Nephrol, Sep. 1, 1996, 7(9):1374.
Honore et al., "Urinary Tissue Inhibitor of Metalloproteinase-2 and Insulin-Like Growth Factor-Binding Protein 7 for Risk Stratification of Acute Kidney Injury in Patients With Sepsis," Crit Care Med, Oct. 2016, 44(10):1851-1860.
Hoste et al., "Derivation and validation of cutoffs for clinical use of cell cycle arrest biomarkers," Nephrol Dial Transplant, 2014, 29:2054-2061.
Hoste et al., "RIFLE criteria for acute kidney injury are associated with hospital mortality in critically ill patients: a cohort analysis.," Crit Care, 2006, 10(3):R73, 10 pp.
Hugo et al., "Thrombospondin 1 precedes and predicts the development of tubulointerstitial fibrosis in glomerular disease in the rat," Kidney Int, 1998, 53(2):302-311.
Hugo et al., "Thrombospondin in Renal Disease," Nephron Exp Nephrol, 2009, 111(3):e61-e66.
Humphreys et al., "Mesenchymal Stem Cells in Acute Kidney Injury," Annu Rev Med., 2008, 59:311-325.
Iglesias et al., "Thyroid Dysfunction and Kidney Disease (Revised version)," Eur J Endocrinol, Dec. 18, 2008, pp. 1-32 retrieved from URL://www.eje.org/content!early/2008/12/18/EJE-08-0837.full.pdf.

Inker et al., "KDOQI US Commentary on the 2012 KDIGO Clinical Practice Guideline for the Evaluation and Management of CKD," Am J Kidney Dis, 2014, 63(5):713-735.
Jaimes et al., "The systemic inflammatory response syndrome (SIRS) to identify infected patients in the emergency room," Intensive Care Med, 2003, 29:1368-1371.
Jang et al., "The innate immune response in ischemic acute kidney injury," Clin Immunol, Jan. 2009, 130(1):41-50.
Jonsson, "The role of fibroblast growth factor 23 in renal disease," Nephrol Dial Transplant, 2005, 20(3):479-482.
Julian et al., "Sources of Urinary Proteins and their Analysis by Urinary Proteomics for the Detection of Biomarkers of Disease," Proteomics Clin Appl., Aug. 26, 2009, 3(9):1029-1043.
Jung et al., "Diagnostic Significance of Urinary Enzymes in Detecting Acute Rejection Crises in Renal Transplant Recipients Depending on Expression of Results Illustrated Through the Example of Alanine Aminopeptidase," Clin Biochem, Aug. 1985, 18(4):257-260.
Kadiroglu et al., The Evaluation of Effects of Demographic Features, Biochemical Parameters, and Cytokines on Clinical Outcomes in Patients with Acute Renal Failure, Renal Failure, 2007, 29(4):503-508.
Kalousová et al., "Soluble Receptor for Advanced Glycation End Products in Patients With Decreased Renal Function," Am J Kidney Dis, Mar. 2006, 47(3):406-411.
Kamata et al., "Up-regulation of glomerular extracellular matrix and transforming growth factor-beta expression in RF/J mice," Kidney Int, 1999, 55(3):864-876.
Kamimoto et al., "Hepatocyte growth factor prevents multiple organ injuries in endotoxemic mice through a heme oxygenase-1-dependent mechanism," Biochem Biophys Res Commun, 2009, 380(2):333-337.
Kasahara et al., "Clinical Significance of Serum Oxidized Low-Density Lipoprotein/beta2-Giycoprotein I Complexes in Patients with Chronic Renal Diseases," Nephron Clin Pract, 2004, 98(1):c15-c24.
Kashani et al., "Discovery and validation of cell cycle arrest biomarkers in human acute kidney injury," Critical Care, 2013, 17(R25):1-12.
Katz and Ronco, "Acute kidney stress—a useful term based on evolution in the understanding of acute kidney injury", Crit Care. 2016; 20: 23, doi: 10.1186/s13054-016-1184-x.
KDIGO Clinical Practice Guideline for Acute Kidney Injury, Official Journal of the International Society of Nephrologoy, Kidney International Supplements, Mar. 2012, 2(1):1-141.
Kehoe et al., "Elevated Plasma Renin Activity Associated with Renal Dysfunction," Nephron, 1986, 44(1):51-57 (abstract only).
Keightley, "A comparison of manual and robotic pipetting for plate-based assays," Laboratory Practice, Journal, 1989, 38(10):53-55—Abstract only.
Kellum, "Acute kidney injury," Crit Care Med, 2008, 36(4):S141-S145.
Kellum et al., "Definition and Classification of Acute Kidney Injury," Nephron Clin Pract, 2008, 109(4):c182-c187.
Keyes et al., "Early diagnosis of acute kidney injury in critically ill patients," Expert Rev Mol Diagn, Jul. 2008, 8(4):455-464.
Khanna et al., "Expression of TGF-beta and fibrogenic genes in transplant recipients with tacrolimus and cyclosporine nephrotoxicity," Kidney Int, 2002, 62(6):2257-2263.
Kharasch et al., "Gene Expression Profiling of Nephrotoxicity from the Sevoflurane Degradation Product Fluoromethyl-2,2-difluoro-1-(trifluoromethyl)vinyl Ether ("Compound A") in Rats," Toxicol Sci, 2006, 90(2):419-431.
Kierdorf et al., "Continuous Renal Replacement Therapies Versus Intermittent Hemodialysis in Acute Renal Failure: What Do We Know?," American Journal of Kidney Diseases, Nov. 1996, 28(5)(Sup 3):S90-S96.
Kiley et al., "Urinary biomarkers: the future looks promising," Kidney Int, 2009, 76(2):133-134.
Kilis-Pstrusinska et al., [Levels of selected soluble adhesion molecules in blood serum of children with chronic glomerulonephritis]. Pol Merkur Lekarski. Apr. 2001;10(58):247-249.

(56) References Cited

OTHER PUBLICATIONS

Kilis-Pstrusinska et al., Serum levels of soluble adhesion molecules in children with glomerulonephritis (GN). Nephrol Dialysis Transplant. Jun. 2001;16(6):A62.

Kimmel et al., "Association of Renal Stress/Damage and Filtration Biomarkers with Subsequent AKI during Hospitalization among Patients Presenting to the Emergency Department," Clin J Am Soc Nephrol, Jun. 2016, 11:938-946.

Kimmel et al., "Immunologic function and survival in hemodialysis patients," Kidney Int, Jul. 1998, 54(1):236-244.

Kingsmore et al., "Multiplexed protein profiling on antibody-based microarrays by rolling circle amplification," Current Opin Biotechnol, Feb. 2003, 14(1):74-81.

Kinsey et al., "Inflammation in Acute Kidney Injury," Nephron Exp Nephrol, 2008, 109(4):e102-e107.

Klein et al., "Renal replacement therapy in acute kidney injury," Medizinische Klinik, Urban & Vogel, Munich, May 2, 2017, 112(5):437-443 (full English translation included).

Komatsuda Atsushi et al., IV. Kanshitsu Nyousaikan, 2. Jin-nyousaikanshougai to heat shock proteins, Annual Review, Jinzou, Jan. 1998:94-102.

Koo et al., "Cadaver versus living donor kidneys: Impact of donor factors on antigen induction before transplantation," Kidney Int., 1999, 56(4):1551-1559.

Kos et al., "Cathepsins B, H, and L and Their Inhibitors Stefin A and Cystatin C in Sera of Melanoma Patients," Clin Cancer Res, Oct. 1997, 3(10):1815-1822.

Kunugi et al., "Inhibition of matrix metalloproteinases reduces ischemia-repertusion acute kidney injury," Lab Invest, 2011, 91(2):170-180.

Kutsukake et al., "Circulating IGF-binding protein 7 (IGFBP7) levels are elevated in patients with endometriosis or undergoing diabetic hemodialysis," Reproductive Biology and Endocrinology, 2008, 6(54):1-6.

Lan, "Clinical significance of determination of serum hyaluronic acid, type III procollagen, collagen IV and laminin in patients with nephropathy," J Guangxi Med Univ., Oct. 2002, 19(5):655-656—incl Engl transl of abstract only.

Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004, 43(2):244-253.

Lang et al., "Heat Shock Protein 60 is Released in Immune-Mediated Glomerulonephritis and Aggravates Disease: In Vivo Evidence for an Immunologic Danger Signal," J Am Soc Nephrol, 2005, 16(2):383-391.

Lapsley et al., "Beta2-glycoprotein-1 (apolipoprotein H) excretion in chronic renal tubular disorders: Comparison with other protein markers of tubular malfunction," J Clin Pathol, 1991, 44(10):812-816.

Larsson et al., "Circulating concentration of FGF-23 increases as renal function declines in patients with chronic kidney disease, but does not change in response to variation in phosphate intake in healthy volunteers," Kidney Int, 2003, 64(6):2272-2279.

Lassnigg et al., "Minimal Changes of Serum Creatinine Predict Prognosis in Patients after Cardiothoracic Surgery: A Prospective Cohort Study," J Am Soc Nephrol, 2004, 15(6):1597-1605.

Lemay et al., "Prominent and Sustained Up-Regulation of GP130-Signaling Cytokines and of the Chemokine MIP-2 in Murine Renal Ischemia-Reperfusion Injury," Transplantation, Mar. 15, 2000, 69(5):959-63.

Li et al., Predictive value of RIFLE classification on prognosis of critically ill patients with acute kidney injury treated with continuous renal replacement therapy, Chin Med J (Engl), May 5, 2009, 122(9):1020-1025.

Liu et al., "Predictive and pathogenetic value of plasma biomarkers for acute kidney injury in patients with acute lung injury," Crit Care Med, 2007, 35(12):2755-2761.

Liu et al., "Serum Interleukin-6 and interleukin-8 are early biomarkers of acute kidney injury and predict prolonged mechanical ventilation in children undergoing cardiac surgery: a case-control study," Critical Care, 2009, 13(4):R104 (9 pp).

Llewelyn et al., "Diagnosis of infection in sepsis," Intensive Care Med, 2001;27 Suppl 1:S10-32.

Lopes-Virella et al., "Urinary High Density Lipoprotein in Minimal Change Glomerular Disease and Chronic Glomerulopathies," Clin Chim Acta, 1979, 94(1):73-81.

López-Bermejo et al., "Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues," J Clin Endocrinol Metab, Jul. 2003, 88(7):3401-3408.

Lu et al., "Biomarker detection in the integration of multiple multi-class genomic studies," Bioinformatics, 2010, 26(3):333-340.

Lu et al., "Increased Macrophage Infiltration and Fractalkine Expression in Cisplatin-Induced Acute Renal Failure in Mice," J Pharmacol Exp Ther, 2008, 324(1):111-117.

MacCallum et al., "Antibody-antigen Interactions: Contact Analysis and Binding Site Topography," J Mol Biol, 1996, 262:732-745.

Maddens et al., "Chitinase-like Proteins are Candidate Biomarkers for Sepsis-induced Acute Kidney Injury," Mol Cell Proteomics, Jan. 10, 2012, 11(6):1-13.

Maier et al., "Massive Chemokine Transcription in Acute Renal Failure Due to Polymicrobial Sepsis," Shock, 2000, 14(2):187-192.

Malm et al., "Changes in the plasma levels of vitamin K-dependent proteins C and S and of C4b-binding protein during pregnancy and oral contraception," Br J Haematol, Apr. 1988, 68(4):437-443.

Malyszko et al., "Visfatin and apelin, new adipocytokines, and their relation to endothelial function in patients with chronic renal failure," Adv Med Sci, 2008, 53(1):32-36.

Mamtani et al., "A simple method to combine multiple molecular biomarkers for dichotomous diagnostic classification," BMC Bioinformatics, Oct. 10, 2006, 7:442, 12 pp.

Mast et al., "Clinical utility of the soluble transferrin receptor and comparison with serum ferritin in several populations," Clin Chem, Jan. 1998, 44(1):45-51.

Matousovic et al., "IgA-containing immune complexes in the urine of IgA nephropathy patients," Nephrol Dial Transplant, Sep. 2006, 21(9):2478-2484.

Matsuda et al., "Beta2-Glycoprotein I—Dependent and -Independent Anticardiolipin Antibody in Patients with End-Stage Renal Disease," Thromb Res., Oct. 15, 1993, 72(2):109-117.

Matsuzaka et al., "Relationship between vitamin K dependent coagulation factors and anticoagulants (protein C and protein S) in neonatal vitamin K deficiency," Arch Dis Childhood, Mar. 1993, 68:297-302.

Mattes, "Experience With a Biomarker Consortium," CPath Predictive Safety Training Consortium, Critical Path Institute, 48 pp.

Mazanowska et al., "Imbalance of metallaproteinase/tissue inhibitors of metalloproteinase system in renal transplant recipients with chronic allograft injury," Transplant Proc, Oct. 2011, 43(8):3000-3003.

McCullough et al., "Contrast-Induced Nephropathy (CIN) Consensus Working Panel: Executive Summary," Rev Cardiovasc Med, 2006, 7(4):177-197.

McIlroy et al., "Biomarkers of Acute Kidney Injury," Anesthesiology, 2010, 112:998-1004.

Meersch et al., "Urinary TIMP-2 and IGFBP7 as Early Biomarkers of Acute Kidney Injury and Renal Recovery following Cardiac Surgery," PLoS One, Mar. 2014; 9(3):e93460, 9 pp.

Meersch et al., "Validation of Cell-Cycle Arrest Biomarkers for Acute Kidney Injury after Pediatric Cardiac Surgery," PLoS One, Oct. 2014, 9(10):e110865. doi: 10.1371/journal.pone.0110865.

Mehran et al., "A Simple Risk Score for Prediction of Contrast-Induced Nephropathy After Percutaneous Coronary Intervention: Development and Initial Validation," J Am Coll Cardiol, 2004, 44(7):1393-1399.

Mehta et al., "Acute Kidney Injury Network: report of an initiative to improve outcomes in acute kidney injury," Crit Care, 2007, 11(2):R31 (8 pp).

Melnikov et al., "Impaired IL-18 processing protects caspase-1-deficient mice from ischemic acute renal failure," J Clin Invest, May 2001, 107(9):1145-1152.

(56) References Cited

OTHER PUBLICATIONS

Mezzano et al., "Endothelial Cell Markers in Chronic Uremia: Relationship with Hemostatic Defects and Severity of Renal Failure," Thromb Res, Dec. 15, 1997, 88(6):465-472.
Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991, 6(4):232-237.
Mishra et al., "Neutrophil gelatinase-associated lipocalin (NGAL) as a biomarker for acute renal injury after cardiac surgery," Lancet, 2005, 365(9466):1231-1238.
Miura et al., "Neutralization of Gro(alpha) and Macrophage Inflammatory Protein-2 Attenuates Renal Ischemia/Reperfusion Injury," Am J Pathol., Dec. 2001, 159(6):2137-2145.
Molls et al., "Keratinocyte-derived chemokine is an early biomarker of ischemic acute kidney injury," Am J Physiol Renal Physiol, May 2006, 290(5):F1187-F1193.
Montagna et al., "Impairment of cellular redox status and membrane protein activities in kidneys from rats with ischemic acute renal failure," Biochim Biophys Acta, 1998, 1407(2):99-108.
Musial et al., "The Heat Shock Protein Profile in Children with Chronic Kidney Disease," Pent Dial Int., 2010, 30(2):227-232.
Musial et al., "Soluble Adhesion Molecules in Chronic Renal Failure (CRF) Children Treated Conservatively," Nephrol Dialysis Transplant, 2002, 17(Abstracts Suppl 1):232.
Nambi et al., "Down regulation of kidney neutral endopeptidase mRNA, protein and activity during acute renal failure: Possible mechanism for ischemia-induced acute renal failure in rats?," Mol Cell Biochem, Jul. 1999, 197(1-2):53-59.
Nejat et al., "Urinary cystatin C is diagnostic of acute kidney injury and sepsis, and predicts mortality in the intensive care unit," Critical Care, 2010, 14(3):R85, 13 pp.
Nelson et al., "A computer program for calculating antibody affinity constants," Comput Methods Programs Biomed, 1988, 27(1):65-68.
Neziri et al., "Cloning and molecular characterization of Dashurin encoded by C20orf116, a PCI-domain containing protein," Biochim Biophys Acta, Apr. 2010, 1800(4):430-438.
Nguyen et al., "Biomarkers for the early detection of acute kidney injury," Pediatr Nephrol, 2008, 23:2151 https://doi.org/10.1007/s00467-007-0470-x.
Nguyen et al., "Heparin-Binding EGF-Like Growth Factor is Up-Regulated in the Obstructed Kidney in a Cell- and Region-Specific Manner and Acts to Inhibit Apoptosis," Am J Pathol, Mar. 2000, 156(3):889-898.
Nishiyama et al., "Up-Regulation of Galectin-3 in Acute Renal Failure of the Rat," Am J Pathol, Sep. 2000, 157(3):815-823.
Norman et al., "Progressive Renal Disease: Fibroblasts, Extracellular Matrix, and Integrins," Exp Nephrol, 1999, 7(2):167-177.
Obuchowski et al., "ROC Curves in Clinical Chemistry: Uses, Misuses, and Possible Solutions," Clinical Chemistry, 2004, 50(7):1118-1125.
Oh, "The insulin-like growth factor system in chronic kidney disease: Pathophysiology and therapeutic opportunities," Kidney Res Clin Pract, 2012;31:26-37.
Ohno et al., "Prognostic significance of tenascin-C expression in clear cell renal cell carcinoma," Oncol Rep, 2008, 20(3):511-516.
Ostermann et al., "Patient Selection and Timing of Continuous Renal Replacement Therapy," Blood Purif, 2016, 42:224-237.
Ozer et al., "A panel of urinary biomarkers to monitor reversibility of renal injury and a serum marker with improved potential to assess renal function," Nat Biotechnol, May 2010, 28(5):486-494.
Pajenda et al., "NephroCheck data compared to serum creatinine in various clinical settings," BMC Nephrology, 2015, 16:206, pp. 1-7.
Parikh et al., "New biomarkers of acute kidney injury," Crit Care Med, 2008, 36(4 Suppl):S159-S165.
Parikh et al., "Urinary IL-18 is an early predictive biomarker of acute kidney injury after cardiac surgery," Kidney Int, 2006, 70(1):199-203.
Paul, "Fundamental Immunology," Third Edition, Structure and Function of Immunoglobulins, 1993, 8:292-295.

Perco et al., "Protein biomarkers associated with acute renal failure and chronic kidney disease," Eur J Clin Invest, 2006, 36(11):753-763.
Picard et al., "Origin of renal myofibroblasts in the model of unilateral ureter obstruction in the rat," Histochem Cell Biol, 2008, 130(1):141-155.
Pilarczyk et al., "Tissue inhibitor of metalloproteinase 2 and insulin-like growth factor-binding protein 7, New biomarker combination for early recognition of acute kidney injury in cardiac surgery," Zeitschrift fur Herz-, Thorax- und Gefaesschirurgie, Mar. 1, 2017, 31:190-199 (full English translation included).
Praught et al., "Are small changes in serum creatinine an important risk factor?," Curr Opin Nephrol Hypertens, 2005, 14(3):265-270.
Price, "Abrupt Changes in Prostate-Specific Antigen Concentration in Acute Renal Failure," Clin Chem, 1993, 39(1):161-162.
Prozialeck et al., "Cell Adhesion Molecules in Chemically-Induced Renal Injury," Pharmacol Ther, Apr. 2007, 114(1):74-93.
Radford, Jr., et al., "Predicting Renal Outcome in IgA Nephropathy," J Am Soc Nephrol, Feb. 1997, 8(2):199-207.
Rajashekar et al., "Systemic diseases with renal manifestations," Prim Care, Jun. 2008, 35(2):297-328.abstract retrieved from URL:www.ncbi.nlm.nih.gov/pubmed/18486717.
Ramesh et al., "Endotoxin and cisplatin synergistically induce renal dysfunction and cytokine production in mice," Am J Physiol Renal Physiol, 2007, 293(1):F325-F332.
Ramesh et al., "TNF-α mediates chemokine and cytokine expression and renal injury in cisplatin nephrotoxicity," J Clin Invest, 2002, 110(6):835-842.
Ramirez et al., "Prospective Study on Autoantibodies Against Apolipoprotein H (Beta2GPI) in Several Clinical Parameters From Patients With Terminal Renal Failure and Functioning Renal Transplants," Transplantation Proceedings, 2009, 41(6):2370-2372.
Ricci et al., "The RIFLE criteria and mortality in acute kidney injury: A systematic review," Kidney Int, 2008, 73(5):538-546.
Ridker, "C-Reactive Protein: A Simple Test to Help Predict Risk of Heart Attack and Stroke," Circulation, 2003, 108:e81-e85, doi:10.1161/01.CIR.0000093381.57779.67.
Rini et al., Renal cell carcinoma. Lancet. Mar. 28, 2009;373(9669):1119-1132.
Ronco et al., "Potential Interventions in Sepsis-Related Acute Kidney Injury," Clin J Am Soc Nephrol, 2008, 3:531-544.
Ronco et al., "The concept of risk and the value of novel markers of acute kidney injury," Critical Care, 2013, 17(117):1-2.
Rosenkranz et al., "P-selectin deficiency exacerbates experimental glomerulonephritis: a protective role for endothelial P-selectin in inflammation," J Clin Invest, 1999, 103(5):649-659.
Rouschop et al., "Pre-transplant plasma and cellular levels of CD44 correlate with acute renal allograft rejection," Nephrol Dial Transplant, 2005, 20(10):2248-2254.
Rouschop et al., "Renal expression of CD44 correlates with acute renal allograft rejection," Kidney Int, 2006, 70(6):1127-1134.
Sabbahy et al., "Ischemic kidney injury and mechanisms of tissue repair," Wiley Interdiscip Rev Syst Biol Med, Sep. 2011, 3(5):606-618.
Sato et al., "Midkine is Involved in Neutrophil Infiltration into the Tubulointerstitium in Ischemic Renal Injury," J Immunol, Sep. 15, 2001, 167(6):3463-3469.
Schaefer et al., "Urinary excretion of cathepsin B and cystatins as parameters of tubular damage," Kidney Int Suppl, Nov. 1994, 47:S64-S67.
Schaefer et al., "Insulin-like Growth Factor-I and the Kidney," Insulin-like Growth Factors, Kluwer Academic/Plenum Publishers, New York, 2003, pp. 244-261.
Schena et al., "EGF and MCP-1 Urinary Excretion is a Suitable Prognostic Marker in IgA Nephropathy," J Am Soc of Nephrology, Meeting of The American Society of Nephrology, Sep. 1, 2002, 13(Program and Abstracts Issue): 458A.
Schiffer et al., "Activated Renal Macrophages are Markers of Disease Onset and Disease Remission in Lupus Nephritis," J Immunol, 2008, 180(3):1938-1947.
Schmaldienst et al., "Angiogenin: A Novel Inhibitor of Neutrophil Lactoferrin Release during Extracorporeal Circulation," Kidney Blood Press Res, 2003, 26(2):107-112.

(56) References Cited

OTHER PUBLICATIONS

Schmidt et al., "Sexual hormone abnormalities in male patients with renal failure," Nephrol Dial Transplant, 2002, 17(3):368-371.
Schulz et al., "Endothelin-1 as an Early Prognostic Marker in Acute Renal Failure (ARF) and Sepsis," Kidney Blood Press Res, 2000, 23(3-5):341-342.
Scott et al., "Searching for Peptide Ligands with an Epitope Library," Science, Jul. 27, 1990, 249:386-390.
Segawa et al., "In situ expression and soluble form of P-selectin in human glomerulonephritis," Kidney Int, 1997, 52(4):1054-1063.
Segerer et al., "Chemokines, Chemokine Receptors, and Renal Disease: From Basic Science to Pathophysiologic and Therapeutic Studies," J Am Soc Nephrol, 2000, 11(1):152-176.
Senatorski et al., "Urine activity of cathepsin B, collagenase and urine excretion of TGF-beta1 and fibronectin in membranous glomerulonephritis," Res Exp Med (Berl), Dec. 1998, 198(4):199-206.
Severini et al., "Diagnostic significance of urinary enzymes: development of a high performance liquid chromatographic method for the measurement of urinary lysozyme," Clinica Chimica Acta, 1987, 163(1):97-103.
Sharma et al., "Two-dimensional fluorescence difference gel electrophoresis analysis of the urine proteome in human diabetic nephropathy," Proteomics, Jul. 2005, 5(10):2648-2655.
Shek et al., "Robotic enzyme-linked immunosorbent assay (ELISA) system for rodent serology: modifications to enhance capacity, throughput and sensitivity," Proc Int Symp Lab Autom Rob, Conference, 1992, pp. 282-298—Abstract only.
Shimoda et al., "Cathepsin G is Required for Sustained Inflammation and Tissue Injury after Reperfusion of Ischemic Kidneys," Am J Pathol, Mar. 2007, 170(3):930-940.
Shlipak et al., "Elevations of Inflammatory and Procoagulant Biomarkers in Elderly Persons With Renal Insufficiency," Circulation, 2003, 107(1):87-92.
Shoji et al., "Plasma angiopoietin-like protein 3 (ANGPTL3) concentration is associated with uremic dyslipidemia," Atherosclerosis, 2009, 207(2):579-584.
Siew et al., "Biological Markers of Acute Kidney Injury," J Am Soc Nephrol, 2011, 22:810-820.
Simmons et al., "Plasma cytokine levels predict mortality in patients with acute renal failure," Kidney Int, Apr. 2004, 65(4):1357-1365.
Song et al., "Expression of TRAIL, DR4, and DR5 in Kidney and Serum From Patients Receiving Renal Transplantation," Transplant Proc, Jun. 2004, 36(5):1340-1343.
Stafford-Smith et al., "Acute Kidney Injury and Chronic Kidney Disease After Cardiac Surgery," Adv Chronic Kidney Dis, Jul. 2008, 15(3):257-277.
Stampfer et al., "Risk Factor Criteria," Circulation, 2004, 109(25 Suppl 1):IV-3-IV-5.
Staško et al., "Soluble P-Selectin During a Single Hemodialysis Session in Patients With Chronic Renal Failure and Erythropoietin Treatment," Clin Appl Thromb Hemost, 2007, 13(4):410-415.
Stenvinkel et al., "High Serum Hyaluronan Indicates Poor Survival in Renal Replacement Therapy," Am J Kidney Dis, Dec. 1999, 34(6):1083-1088.
Stuard et al., "Soluble Adhesion Molecules in Chronic Renal Failure Patients," Nephrol Dialysis Transplant, 1997, 12(9):A100.
Study of the concentration of hyaluronic acid in diabetic nephrophy, Diabetes, 2001, 44(Suppl 1): S-167 [in Japanese] (Tonyobyojinsho Ni Okeru Nyochu Hiaruronsan Nodo No Kento, Tonyobyo, 2001;44(Suppl 1): S-167).
Su et al., "Diagnostic value of urine sTREM-1 for sepsis and relevant acute kidney injuries: a prospective study," Crit Care, 2011, 15:R250, pp. 1-10.
Sun et al., "Enhanced Expression of ANGPTL2 in the Microvascular Lesions of Diabetic Glomerulopathy," Nephron Exp Nephrol, 2007, 105(4):e117-e123.
Sun et al., A Survey on the Relationship between the Epidermal Growth Factor and Renal Function. Int J Transpl Hemopurific Dec. 31, 2006;4(1):41-44 (abstract English translation).
Supavekin et al., "Differential gene expression following early renal ischemia/repertusion," Kidney Int, 2003, 63(5):1714-1724.
Sutton, "Alteration of microvascular permeability in acute kidney injury," Microvasc Res, Jan. 2009, 77(1):4-7.
Sutton et al., Injury of the renal microvascular endothelium alters barrier function after ischemia, Am J Physiol Renal Physiol, 2003, 285(2):F191-F198.
Sutton et al., "Microvascular endothelial injury and dysfunction during ischemic acute renal failure," Kidney Int, 2002, 62(5):1539-1549.
Sykes et al., "Analytical Relationships Among Biosite, Bayer, and Roche Methods for BNP and NT-proBNP," Am J Clin Path+E151ol, 2005, 123:584-590.
Symon et al., "The endogenous insulin-like growth factor system in radiocontrast nephropathy," Am J Physiol Renal Physiol, 1998, 274(3 Pt 2):F490-F497.
Takada et al., "The Cytokine-adhesion Molecule Cascade in Ischemia/Reperfusion Injury of the Rat Kidney," Inhibition by a Soluble P-selectin Ligand, J Clin Invest, Jun. 1997, 99(11):2682-2690.
Tan et al., "The level of urinary secretory immunoglobulin A (sIgA) of patients with IgA nephropathy is elevated and associated with pathological phenotypes," Clin Exp Immunol, Apr. 2009, 156(1):111-116.
Tao et al., "Expression of 60-kDa and Inducible 70-kDa Stress Proteins in Gentamicin-Induced Acute Renal Failure," Clin Exp Nephrol, Jul. 1997, 1:254-260.
Tary-Lehmann et al., "Enzyme-Linked Immunosorbent Assay Spot Detection of Interferon-Gamma and Interleukin 5-Producing Cells as a Predictive Marker for Renal Allograft Failure," Transplantation, Jul. 27, 1998, 66(2):219-224.
Taulan et al., "Comprehensive analysis of the renal transcriptional response to acute uranyl nitrate exposure," BMC Genomics, Jan. 11, 2006, 7(2):1-14.
Teppo et al., "Soluble Intercellular Adhesion Molecule-1 (sICAM-1) after Kidney Transplantation: The Origin and Role of Urinary sICAM-1?," Transplantation, Apr. 27, 2001, 71(8):1113-1119.
Thakar et al., "A Clinical Score to Predict Acute Renal Failure after Cardiac Surgery," J Am Soc Nephrol, 2005, 16:162-168.
Thakar et al., "Identification of thrombospondin 1 (TSP-1) as a novel mediator of cell injury in kidney ischemia," J Clin Invest, Dec. 2005, 115(12):3451-3458.
Thiele et al., "AKI Associated with Cardiac Surgery," Clin J Ann Soc Nephrol, Mar. 2015, 10:500-514.
Thorburn et al., "CXC and CC chemokines induced in human renal epithelial cells by inflammatory cytokines," APMIS, Jul. 2009, 117(7):477-487.
Thurman et al., C3a is Required for the Production of CXC Chemokines by Tubular Epithelial Cells after Renal Ishemia/Repertusion. J Immunol. Feb. 1, 2007;178(3):1819-1828Moda et al., Cathepsin G is Required for Sustained Inflammation and Tissue Injury after Reperfusion of Ischemic Kidneys. Am J Pathol. Mar. 2007;170(3):930-940.
Timoshanko et al., "Interleukin-12 from Intrinsic Cells is an Effector of Renal Injury in Crescentic Glomerulonephritis," J Am Soc Nephrol, 2001, 12(3):464-471.
Torres et al., "The ratio of epidermal growth factor to monocyte chemotactic peptide-1 in the urine predicts renal prognosis in IgA nephropathy," Kidney Int, 2008, 73(3):327-333.
Torzewski et al., "Animal Models of C-Reactive Protein," Hindawi Publishing Corporation, Mediators of Inflammation, 2014, vol. 2014, Article ID 683598 (7 pp).
Triage BNP Test Product Insert: Rapid Quantitative Test B-type Natriuretic Peptide, Alere Catalog #98000XR, 2011, 28 pp.
Vaidya et al., "Biomarkers of Acute Kidney Injury," Annu Rev Pharmacol Toxicol, 2008, 48:463-493.
Vaidya et al., "Mechanistic biomarkers for cytotoxic acute kidney injury," Expert Opin Drug Metab Toxicol, 2006, 2(5):697-713.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Van Der Vekens et al., "Human and equine cardiovascular endrocrinology: beware to compare," Cardiovascular Endocrinology, 2013, 2(4):67-76.

(56) References Cited

OTHER PUBLICATIONS

Van Erp et al., "Application of a Sol Particle Immunoassay to the Determination of Affinity Constants of Monoclonal Antibodies," J Immunoassay, 1991, 12(3):425-443.

Vanhoutte et al., "Biomarker discovery with SELDI-TOF MS in human urine associated with early renal injury: evaluation with computational analytical tools," Nephrol Dial Transplant, 2007, 22(10):2932-2943.

Venugopal et al., "Effect of Remote Ischemic Preconditioning on Acute Kidney Injury in Nondiabetic Patients Undergoing Coronary Artery Bypass Graft Surgery: A Secondary Analysis of 2 Small Randomized Trials," Am J Kidney Dis, Dec. 2010, 56(6-2):1043-1049.

Vijayan et al., "Clinical Use of the Urine Biomarker [TIMP-2] x [IGFBP7] for Acute Kidney Injury Risk Assessment," Am J Kidney Dis, 2016, 68(1):19-28.

Villanueva et al., "Ischemic acute renal failure induces the expression of a wide range of nephrogenic proteins," Am J Physiol Regul Integr Comp Physiol, 2006, 290(4):R861-R870.

Vonderscher, "Biomarker of Drug Induced Kidney Injury Qualification for Regulatory Decision Making," (CRADA). IOM/FDA, Silver Spring, MD, Apr. 2007, 23:1-31.

Voshol et al., Evaluation of Biomarker Discovery Approaches to Detect Protein Biomarkers of Acute Renal Allograft Rejection. J Proteome Res. Jul.-Aug. 2005;4(4):1192-1199.

Waikar et al., "Imperfect Gold Standards for Kidney Injury Biomarker Evaluation," J Am Soc Nephrol, Jan. 2012, 23(1):13-21.

Waikar et al., Diagnosis, Epidemiology and Outcomes of Acute Kidney Injury. Clin J Am Soc Nephrol. May 2008;3 (3):844-861.

Wan et al., "The pathogenesis of septic acute renal failure," Curr Opin Crit Care, Dec. 2003;9(6):496-502.

Wang et al., "Netrin-1 and kidney injury. I. Netrin-1 protects against ischemia-reperfusion injury of the kidney," Am J Physiol Renal Physiol, 2008, 294(4):F739-F747.

Wang et al., "Validation of putative genomic biomarkers of nephrotoxicity in rats," Toxicology, 2008, 246:91-100.

Ward et al., "Binding activities of a repertoire of single immunoglobulin variable domains secreted from *Escherichia coli*," Nature, Oct. 12, 1989, 341:544-546.

Wasung et al., "Biomarkers of renal function, which and when?," Clinica Chimica Acta, 2015, 438:350-357.

Wen et al., "One dose of cyclosporine A is protective at initiation of folic acid-induced acute kidney injury in mice," Nephrol Dial Transplant, 2012, 27:3100-3109.

Wetz et al., "Quantification of urinary TIMP-2 and IGFBP-7: an adequate diagnostic test to predict acute kidney injury after cardiac surgery?," Critical Care, 2015, 19:3, pp. 1-7.

Wijeysundera et al., "Derivation and Validation of a Simplified Predictive Index for Renal Replacement Therapy After Cardiac Surgery," JAMA, Apr. 25, 2007, 297:1801-1809.

WIKI: "Chronic kidney disease," Jan. 3, 2020, 8 pp, retrieved from the internet: URL:https://en.wikipedia.org/wiki/Chronic_kidney_disease [retrieved on Jan. 21, 2020].

Wilson et al., "Simplified conjugation chemistry for coupling peptides to F(ab') fragments: autologous red cell agglutination assay for HIV-1 antibodies," J Immunol Methods, 1994, 175:267-273.

Wilson et al., "Urinary Lysozyme: III. Lysozymuria in Children with the Nephrotic Syndrome," J Pediatr, Feb. 1950, 36(2):199-211.

Winchester et al., "Sorbents in Acute Renal Failure and End-Stage Renal Disease: Middle Molecule and Cytokine Removal," Blood Purif, 2004, 22(1):73-77.

Witzgall et al., "Localization of Proliferating Cell Nuclear Antigen, Vimentin, c-Fos, and Clusterin in the Postischemic Kidney: Evidence for a Heterogenous Genetic Response among Nephron Segments, and a Large Pool of Mitotically Active and Dedifferentiated Cells," J Clin Invest, May 1994, 93:2175-2188.

Yan et al., "Expression of MMP-2 and TIMP-1 in renal tissue of patients with chronic active antibody-mediated renal graft rejection," Diagn Pathol, Oct. 12, 2012;7:141.

Yang et al., "Remote Ischemic Preconditioning for Prevention of Acute Kidney Injury: A Meta-analysis of Randomized Controlled Trials," Am J Kidney Dis, 2014, 64(4):574-583.

Yang et al., "Acute renal failure during sepsis: Potential role of cell cycle regulation," J Infect, 2009, 58:459-464.

Yang et al., Frequency of anti-bactericidal/permeability-increasing protein (BPI) and anti-azurocidin in patients with renal disease, Clin Exp Immunol, 1996, 105(1):125-131.

Yarmush et al., "Coupling of antibody-binding fragments to solid-phase supports: site-directed binding of F(ab')2 fragments," J Biochem Biophys Methods, 1992, 25:285-297.

Yasuda et al., "Insulin-like growth factor-I increases p21 expression and attenuates cisplatin-induced acute renal injury in rats," Clin Exp Nephrol, 2004, 8:27-35.

Yasuda et al., "Simvastatin improves sepsis-induced mortality and acute kidney injury via renal vascular effects," Kidney Int, May 2006, 69(9):1535-1542.

Yu et al., "Urinary biomarkers trefoil factor 3 and albumin enable early detection of kidney tubular injury," Nat Biotechnol, May 2010, 128(5):470-477.

Yuan et al., "Combining Multiple Biomarker Models in Logistic Regression," Biometrics, Jun. 2008, 64:431-439.

Yuen et al., "Ischemic and Nephrotoxic Acute Renal Failure are Distinguished by their Broad Transcriptomic Responses," Physiol Genomics, May 16, 2006, 25(3):375-386.

Zaffanello et al., "Early diagnosis of acute kidney injury with urinary biomarkers in the newborn," J Matern-Fetal Neonatal Med, Oct. 2009, 22(S3):62-66.

Zager et al., "Proximal tubular cytochrome c efflux: Determinant, and potential marker, of mitochondrial injury," Kidney Int, 2004, 65(6):2123-2134.

Zarjou et al., "Sepsis and Acute Kidney Injury," J Am Soc Nephrol, 2011, 22:999-1006.

Zhang et al., "The level of serum secretory IgA of patients with IgA nephropathy is elevated and associated with pathological phenotypes," Nephrol Dial Transplant, Jan. 2008, 23(1):207-212.

Zheng et al., "Antiphospholipid antibody profiles in lupus nephritis with glomerular microthrombosis: a prospective study of 124 cases," Arthritis Research & Therapy, 2009, 11(R93):1-9.

Zhu et al., Expression of Urinary Epidermal Growth Factor and Renal Function. J Clin Urol Dec. 1998 31-13(8):374-379 (abstract English translation).

Office Action and Search Report issued on Mar. 24, 2014 in JP 2012-554148—includes English translation.

Office Action issued on Aug. 28, 2013 in AU 2010330735.

Office Action issued on Jun. 11, 2019 in BR BR1120120151983.

Office Action issued on Feb. 6, 2017 in CA 2,784,889.

Office Action and Search Report issued on Oct. 21, 2016 by SIPO in CN 2015100931563—includes English translation of Search Report only.

Office Action and Search Report issued on Jan. 24, 2014 by SIPO in CN 201080062499.9—includes English translation.

Office Action and Search Report issued on Sep. 15, 2014 by SIPO in CN 201080062499.9—includes English translation.

Office Action and Search Report issued on Apr. 23, 2013 by SIPO in CN 200980140805.3—Includes English Translation.

Office Action issued on May 29, 2013 by SIPO in CN 2009801406946—includes English translation.

Office Action issued on Jun. 25, 2013 by SIPO in CN 201080014932.1—includes English translation.

Office Action issued on Jul. 1, 2013 by SIPO in CN 200980149555.X—includes English translation.

Office Action issued on Jul. 1, 2013 by SIPO in CN 200980149636.X—includes English translation.

Office Action issued on Jul. 18, 2013 by SIPO in CN 201080057014.7—includes English translation.

Non-Final Office Action issued on Dec. 17, 2012 in CN 2009801542245.

Office Action issued on Sep. 8, 2014 in EA 201290387.

Office Action issued on Feb. 7, 2014 in EP 10838357.1.

Office Action issued on Jun. 17, 2014 in EP 10838357.1.

Office Action issued on Aug. 11, 2017 in EP 16165742.4.

Office Action issued on Jan. 11, 2017 in IN 1500/MUMNP/2012.

(56) References Cited

OTHER PUBLICATIONS

Office Action issued on Mar. 14, 2017 in JP 2016-129351—includes English translation.
Office Action issued on Aug. 4, 2015 in JP 2014-237875—includes English translation.
Office Action and Search Report issued on Jun. 24, 2014 in JP 2012-544950—includes English translation.
Non-Final Office Action issued on Feb. 5, 2013 in JP 2011-525262—includes English translation.
Office Action issued on May 17, 2017 in KR 10-2012-7019128—includes English translation.
Office Action issued on May 17, 2017 in KR 10-2012-7024981—includes English translation.
Office Action issued on Aug. 13, 2018 in KR 10-2018-7015064—includes English translation.
Office Action issued on Oct. 18, 2018 in U.S. Appl. No. 15/676,828.
Non-Final Office Action issued on Apr. 6, 2017 in U.S. Appl. No. 13/164,768.
Non-Final Office Action issued on Nov. 15, 2016 in U.S. Appl. No. 14/708,225.
Final Office Action issued on Jun. 7, 2013 in U.S. Appl. No. 13/061,446.
Final Office Action issued on Aug. 23, 2013 in U.S. Appl. No. 13/061,413.
Non-Final Office Action issued on Mar. 5, 2013 in U.S. Appl. No. 13/125,454.
Non-Final Office Action issued on Apr. 18, 2013 in U.S. Appl. No. 13/389,363.
Non-Final Office Action issued on May 1, 2013 in U.S. Appl. No. 13/148,030.
Non-Final Office Action issued on Aug. 27, 2013 in U.S. Appl. No. 13/125,360.
Non-Final Office Action issued on Nov. 27, 2012 in U.S. Appl. No. 13/130,474.
Restriction Requirement issued on Mar. 20, 2013 in U.S. Appl. No. 13/148,031.
Restriction Requirement issued on Jul. 1, 2013 in U.S. Appl. No. 13/517,244.
Restriction Requirement issued on Sep. 5, 2012 in U.S. Appl. No. 13/061,413.
Non-Final Office Action issued on Jun. 20, 2013 in U.S. Appl. No. 13/577,242.
Non-Final Office Action issued on Jan. 2, 2013 in U.S. Appl. No. 13/061,413.
Non-Final Office Action issued on Jan. 24, 2013 in U.S. Appl. No. 13/125,360.
Non-Final Office Action issued on Feb. 1, 2013 in U.S. Appl. No. 13/508,363.
Non-Final Office Action issued on Feb. 14, 2013 in U.S. Appl. No. 13/577,243.
Non-Final Office Action issued on Dec. 18, 2012 in U.S. Appl. No. 13/164,768.
Non-Final Office Action issued on Nov. 16, 2012 in U.S. Appl. No. 13/389,351.
Non-Final Office Action issued on Oct. 12, 2012 in U.S. Appl. No. 13/061,446.
Response to Non-Final Office Action filed on Jul. 2, 2013 in U.S. Appl. No. 13/061,413.
Response to Restriction Requirement filed on Oct. 16, 2012 in U.S. Appl. No. 13/061,413.
Extended European Search Report issued Dec. 3, 2020, in European patent application (No. 18797960.4).
Extended European Search Report issued on Nov. 4, 2016 in EP 15190063.
Extended European Search Report issued on Oct. 17, 2016 in EP 16165742.
Partial European Search Report issued on Jul. 29, 2016 in EP 15190063.6.
Extended European Search Report issued on Nov. 11, 2014 in EP 12802159.
Extended European Search Report and Written Opinion issued on Aug. 13, 2013 in EP 11751238.
Extended European Search Report and Written Opinion issued on Aug. 16, 2013 in EP 11748210.
Extended European Search Report and Written Opinion issued on Apr. 15, 2013 in EP 10817878.
Extended European Search Report and Written Opinion issued on May 21, 2013 in EP 10829198.
Extended European Search Report and Written Opinion issued on May 24, 2013 in EP 10829191.
Extended European Search Report and Written Opinion issued on Jun. 3, 2013 in EP 10838357.
Extended European Search Report and Written Opinion issued on Jun. 6, 2013 in EP 10818036.
Extended European Search Report and Written Opinion issued on Jun. 13, 2013 in EP 11740468.
Extended European Search Report and Written Opinion issued on Jun. 13, 2013 in EP 11740469.
Extended European Search Report and Written Opinion issued on Jun. 18, 2013 in EP 11740470.
Extended European Search Report and Written Opinion issued on Jul. 16, 2013 in EP 10812639.
Extended European Search Report and Written Opinion issued on Dec. 3, 2012 in EP 10807232.3.
Extended European Search Report and Written Opinion issued on Dec. 3, 2012 in EP 10807254.7.
Extended European Search Report and Written Opinion issued on Feb. 22, 2012 in EP 9810705.
Extended European Search Report and Written Opinion issued on Feb. 23, 2012 in EP 2009828325.
Extended European Search Report and Written Opinion issued on Jun. 8, 2012 in EP 09825600.1.
Extended European Search Report and Written Opinion issued on Jul. 27, 2012 in EP 10739152.6.
Extended European Search Report and Written Opinion issued on Aug. 23, 2012 in EP 09822670.7.
Extended European Search Report and Written Opinion issued on Aug. 23, 2012 in EP 10739155.
Extended European Search Report and Written Opinion issued on Oct. 24, 2011 in EP 09810695.8.
Extended European Search Report and Written Opinion issued on Jul. 9, 2012 in EP 10739150.
Response to Extended European Search Report and Written Opinion filed on May 16, 2012 in EP 09810695.8.
International Preliminary Report on Patentability issued on May 24, 2013 in PCT/US2011/055055.
International Preliminary Report on Patentability issued on Sep. 7, 2012 in PCT/US2011/026384.
International Preliminary Report on Patentability issued on Mar. 10, 2011 in PCT/US2009/055449.
International Preliminary Report on Patentability issued on Mar. 10, 2011 in PCT/US2009/055460.
International Preliminary Report on Patentability issued on Mar. 29, 2011 in PCT/US2010/049234.
International Preliminary Report on Patentability issued on Apr. 5, 2012 in PCT/US2010/049695.
International Preliminary Report on Patentability issued on May 5, 2011 in PCT/US2009/061561.
International Preliminary Report on Patentability issued on May 5, 2011 in PCT/US2009/061562.
International Preliminary Report on Patentability issued on May 10, 2011 in PCT/US2009/063906.
International Preliminary Report on Patentability issued on May 18, 2012 in PCT/US2010/055730.
International Preliminary Report on Patentability issued on Jun. 3, 2011 in PCT/US2009/065419.
International Preliminary Report on Patentability issued on Jul. 5, 2012 in PCT/US2010/061377.
International Preliminary Report on Patentability issued on Aug. 16, 2012 in PCT/US2011/023830.
International Preliminary Report on Patentability issued on Aug. 16, 2012 in PCT/US2011/023831.

(56) References Cited

OTHER PUBLICATIONS

International Preliminary Report on Patentability issued on Aug. 16, 2012 in PCT/US2011/023832.
International Preliminary Report on Patentability issued on Aug. 18, 2011 in PCT/US2010/023292.
International Preliminary Report on Patentability issued on Aug. 18, 2011 in PCT/US2010/023294.
International Preliminary Report on Patentability issued on Oct. 21, 2011 in PCT/US2010/023297.
International Search Report and Written Opinion issued on Dec. 3, 2010 in PCT/US2010/049695.
International Search Report and Written Opinion issued on Jun. 18, 2013 in PCT/US2013/028005.
International Search Report and Written Opinion issued on May 15, 2013 in PCT/US2013/023479.
International Search Report and Written Opinion issued on Mar. 15, 2013 in PCT/US2012/066152.
International Search Report and Written Opinion issued on Jan. 15, 2010 in PCT/US2009/063906.
International Search Report and Written Opinion issued on Jan. 18, 2012 in PCT/US2011/053015.
International Search Report and Written Opinion issued on Jan. 19, 2011 in PCT/US2010/055721.
International Search Report and Written Opinion issued on Jan. 20, 2010 in PCT/US2009/061561.
International Search Report and Written Opinion issued on Feb. 8, 2011 in PCT/US2010/055730.
International Search Report and Written Opinion issued on Feb. 24, 2012 in PCT/US2011/055055.
International Search Report and Written Opinion issued on Mar. 8, 2011 in PCT/US2010/061377.
International Search Report and Written Opinion issued on Mar. 30, 2010 in PCT/US2009/065419.
International Search Report and Written Opinion issued on Apr. 13, 2010 in PCT/US2009/061562.
International Search Report and Written Opinion issued on Apr. 22, 2010 in PCT/US2010/023294.
International Search Report and Written Opinion issued on Apr. 27, 2011 in PCT/US2011/023830.
International Search Report and Written Opinion issued on Apr. 27, 2011 in PCT/US2011/023831.
International Search Report and Written Opinion issued on Apr. 29, 2011 in PCT/US2011/023832.
International Search Report and Written Opinion issued on Apr. 30, 2010 in PCT/US2010/023292.
International Search Report and Written Opinion issued on May 2, 2012 in PCT/US2012/022926.
International Search Report and Written Opinion issued on May 10, 2012 in PCT/US2012/020571.
International Search Report and Written Opinion issued on May 17, 2011 in PCT/US2011/026384.
International Search Report and Written Opinion issued on Jun. 3, 2010 in PCT/US2010/023297.
International Search Report and Written Opinion issued on Jun. 3, 2011 in PCT/US2011/026759.
International Search Report and Written Opinion issued on Jun. 20, 2012 in PCT/US2012/020572.
International Search Report and Written Opinion issued on Sep. 7, 2012 in PCT/US2012/043279.
International Search Report and Written Opinion issued on Oct. 8, 2010 in PCT/US2010/044708.
International Search Report and Written Opinion issued on Oct. 28, 2010 in PCT/US2010/044772.
International Search Report and Written Opinion issued on Nov. 18, 2010 in PCT/US2010/046910.
International Search Report and Written Opinion issued on Nov. 25, 2011 in PCT/US2011/001125.
International Search Report and Written Opinion issued on Nov. 25, 2011 in PCT/US2011/001127.
International Search Report and Written Opinion issued on Nov. 25, 2011 in PCT/US2011/001128.
International Search Report and Written Opinion issued on Dec. 3, 2010 in PCT/US2010/049234.
International Search Report and Written Opinion issued on Dec. 10, 2009 in PCT/US2009/055449.
International Search Report and Written Opinion issued on Dec. 15, 2011 in PCT/US2011/001126.
International Search Report and Written Opinion issued on Dec. 31, 2009 in PCT/US2009/055460.
International Search Report and Written Opinion issued on Sep. 21, 2012 in PCT/US2012/045583.
Supplemental European Search Report and Written Opinion issued on Jul. 6, 2012 in EP 09822669.9.
Search Report issued on May 23, 2013 by SIPO in CN 200980149555. X—includes English translation.
Search Report issued on Jun. 9, 2013 by SIPO in CN 201080014932. 1—includes English translation.
Search Report issued on Jun. 17, 2013 by SIPO in CN 200980149636. X—includes English translation.
Search Report issued on Jul. 8, 2013 by SIPO in CN 201080057014. 7—includes English translation.
Search Report and Written Opinion issued on Apr. 15, 2013 by SIPO in CN 2009801406946—includes English translation.
Search Report and Written Opinion issued on Nov. 23, 2012 in CN 200980154224.5—includes English translation.
Kashani et al., "Biomarkers of acute kidney injury: the pathway from discovery to clinical adoption," Clin Chem Lab Med, 2017, 55(8):1074-1089.
Pilarczyk et al., "Urinary [TIMP-2]*[IGFBP7] for early prediction of acute kidney injury after coronary artery bypass surgery," Ann Intensive Care, 2015, 5:50, 11 pp.
Navas et al., "Renal replacement therapy in the critical patient: Treatment variation over time," Med Intensiva, 2012, 36(8):540-547.
Qi et al., "Effects of different peptide fragments derived from proadrenomedullin on gene expression of adrenomedulin gene," Peptides, 2002, 23:1141-1147.

\* cited by examiner

METHODS AND COMPOSITIONS FOR DIAGNOSIS AND PROGNOSIS OF RENAL INJURY AND RENAL FAILURE

The present application claims priority from U.S. Provisional Patent Application 61/288,327 filed Dec. 20, 2009, U.S. Provisional Patent Application 61/308,861 filed Feb. 26, 2010, U.S. Provisional Patent Application 61/410,875 filed Nov. 6, 2010, U.S. Provisional Patent Application 61/410,878 filed Nov. 6, 2010, U.S. Provisional Patent Application 61/410,879 filed Nov. 6, 2010, and U.S. Provisional Patent Application 61/410,880 filed Nov. 6, 2010, each of which is hereby incorporated in its entirety including all tables, figures and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that AR complicates about 5% of hospital admissions, 4-15% of cardiopulmonary bypass surgeries, and up to 30% of intensive care admissions. AR may be categorized as prerenal, intrinsic renal, or postrenal in causation. Intrinsic renal disease an be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in theirentirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |

| Type | Risk Factors |
|---|---|
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., Crit Care. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:
"Loss": persistent need for renal replacement therapy for more than four weeks.
"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al, *Kidney int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of a plurality of assays, wherein one or more of the assays is configured to detect Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 (collectively referred to herein as "kidney injury markers, and individually as a "kidney injury marker") The plurality of assays are combined to provide a "biomarker panel approach" which can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. A plurality of assay results, for example comprising one, two, three, or more measured concentrations of markers selected from the group consisting of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury. Preferred methods comprise at least two assay results selected from the group consisting of a measured concentration of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 2,4, C-X-C motif chemokine 6, C-C motif chemokine 13, C-X-C motif chemokines-1, -2, and -3. In certain of these preferred embodiments, the assay results comprise at least three of a measured concentration of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1.

Preferred panels comprise performing assays that detect at least two of the foregoing kidney injury markers. In certain embodiments, these panels include measurement of Metalloproteinase inhibitor 2 and Interleukin-11; Hyaluronic acid and Immunoglobulin A; Insulin-like growth factor-binding protein 7 and Neutrophil elastase; Metalloproteinase inhibitor 2 and Neutrophil elastase; Hyaluronic acid and Neutrophil elastase; Insulin-like growth factor-binding protein 7 and Metalloproteinase inhibitor 2; Insulin-like growth factor-binding protein 7 and Alpha-1 antitrypsin; Hyaluronic acid and Insulin-like growth factor-binding protein 7; Beta-2-glycoprotein 1 and Insulin-like growth factor-binding protein 7; Hyaluronic acid and Alpha-1 antitrypsin; Serum amyloid P-component and Insulin-like growth factor-binding protein 7; Hyaluronic acid and Serum amyloid P-component; Insulin-like growth factor-binding protein 7 and Immunoglobulin A; Insulin-like growth factor-binding protein 7 and Interleukin-11; Metalloproteinase inhibitor 2 and Hyaluronic acid; Serum amyloid P-component and Metalloproteinase inhibitor 2; Metalloproteinase inhibitor 2 and Alpha-1 antitrypsin; Hyaluronic acid and Interleukin-11; Beta-2-glycoprotein 1 and Hyaluronic acid; Metalloproteinase inhibitor 2 and Immunoglobulin A; Neutrophil elastase and Hepatocyte growth factor; Insulin-like growth factor-binding protein 7 and Hepatocyte growth factor; Insulin-like growth factor-binding protein 7 and CXCL-1-2 and -3; or Neutrophil elastase and Tumor necrosis factor receptor superfamily member 11B; or Metalloproteinase inhibitor 2 and Beta-2-glycoprotein 1.

Still other preferred panels comprise performing assays that detect at least three of the foregoing kidney injury markers. In certain embodiments, these panels include measurement of Beta-2-glycoprotein 1 and Hyaluronic acid and Alpha-1 antitrypsin; Beta-2-glycoprotein 1 and Insulin-like growth factor-binding protein 7 and Alpha-1 antitrypsin; Beta-2-glycoprotein 1 and Metalloproteinase inhibitor 2 and Alpha-1 antitrypsin; Hyaluronic acid and Neutrophil elastase and Insulin-like growth factor-binding protein 7; Neutrophil elastase and Insulin-like growth factor-binding protein 7 and Cathepsin D; Hyaluronic acid and Neutrophil elastase and Alpha-1 antitrypsin; Insulin-like growth factor-binding protein 7 and Hepatocyte growth factor and Alpha-1 antitrypsin; Insulin-like growth factor-binding protein 7 and Immunoglobulin A and Alpha-1 antitrypsin; Hyaluronic acid and Insulin-like growth factor-binding protein 7 and Alpha-1 antitrypsin; Neutrophil elastase and Hepatocyte growth factor and Alpha-1 antitrypsin; Neutrophil elastase and Insulin-like growth factor-binding protein 7 and Alpha-1 antitrypsin; Hyaluronic acid and Immunoglobulin A and Alpha-1 antitrypsin; Neutrophil elastase and Insulin-like growth factor-binding protein 7 and Hepatocyte growth factor, Neutrophil elastase and Insulin-like growth factor-binding protein 7 and Metalloproteinase inhibitor 2; Neutrophil elastase and Metalloproteinase inhibitor 2 and Alpha-1 antitrypsin; Hyaluronic acid and Neutrophil elastase and Hepatocyte growth factor, Neutrophil elastase and Metalloproteinase inhibitor 2 and Hepatocyte growth factor, Neutrophil elastase and Serum amyloid P-component and Alpha-1 antitrypsin; Hyaluronic acid and Serum amyloid P-component and Alpha-1 antitrypsin; Neutrophil elastase and Tumor necrosis factor receptor superfamily member 11B and Alpha-1 antitrypsin; Serum amyloid P-component and Insulin-like growth factor-binding protein 7 and Alpha-1 antitrypsin; Hyaluronic acid and Neutrophil elastase and Cathepsin D; Hyaluronic acid and Insulin-like growth factor-binding protein 7 and Beta-2-glycoprotein-1; Hyaluronic acid and Neutrophil elastase and Serum amyloid P component; Neutrophil elastase and Insulin-like growth factor-binding protein 7 and C-C motif chemokine 24; Cathepsin D and Neutrophil elastase and Metalloproteinase inhibitor 2; Hyaluronic acid and Neutrophil elastase and Metalloproteinase inhibitor 2; or Hyaluronic acid and Insulin-like growth factor-binding protein 7 and Metalloproteinase inhibitor 2.

Most preferably, the plurality of assays comprise assays that detect one, two or three, or more of Insulin-like growth factor-binding protein 7, Metalloproteinase inhibitor 2, Beta-2-glycoprotein 1, Neutrophil elastase, Alpha-1 antitrypsin, Serum amyloid P-component, and Hyaluronic Acid.

In preferred embodiments, the measured marker results are combined to provide a single composite value. Numerous methods are known in the art for combining marker results. In certain embodiments, functions used to combine marker results may be selected from the group consisting of Metalloproteinase inhibitor 2×Interleukin-11; Hyaluronic acid×Immunoglobulin A; Insulin-like growth factor-binding protein 7×Neutrophil elastase; Metalloproteinase inhibitor 2×Neutrophil elastase; Hyaluronic acid×Neutrophil elastase; Insulin-like growth factor-binding protein 7×Metalloproteinase inhibitor 2; Insulin-like growth factor-binding protein 7/Alpha-1 antitrypsin; Hyaluronic acid×Insulin-like growth factor-binding protein 7; Beta-2-glycoprotein 1×Insulin-like growth factor-binding protein 7; Hyaluronic acid/Alpha-1 antitrypsin; Serum amyloid P-component×Insulin-like growth factor-binding protein 7; Hyaluronic acid×Serum amyloid P-component; Insulin-like growth factor-binding protein 7×Immunoglobulin A; Insulin-like growth factor-binding protein 7×Interleukin-11; Metalloproteinase inhibitor 2×Hyaluronic acid; Serum amyloid P-component×Metalloproteinase inhibitor 2; Metalloproteinase inhibitor 2/Alpha-1 antitrypsin; Hyaluronic acid×Interleukin-11; Beta-2-glycoprotein 1×Hyaluronic acid; Metalloproteinase inhibitor 2×Immunoglobulin A; Metalloproteinase inhibitor 2×Beta-2-glycoprotein 1; Beta-2-glycoprotein 1×Hyaluronic acid/Alpha-1 antitrypsin; Beta-2-glycoprotein 1×Insulin-like growth factor-binding protein 7/Alpha-1 antitrypsin; Beta-2-glycoprotein 1×Metalloproteinase inhibitor 2/Alpha-1 antitrypsin; Hyaluronic acid×Neutrophil elastase×Insulin-like growth factor-binding protein 7; Neutrophil elastase×Insulin-like growth factor-binding protein 7×Cathepsin D; Hyaluronic acid×Neutrophil elastase/Alpha-1 antitrypsin; Insulin-like growth factor-binding protein 7×Hepatocyte growth factor/Alpha-1 antitrypsin; Insulin-like growth factor-binding protein 7×Immunoglobulin A/Alpha-1 antitrypsin; Hyaluronic acid×Insulin-like growth factor-binding protein 7/Alpha-1 antitrypsin; Neutrophil elastase×Hepatocyte growth factor/Alpha-1 antitrypsin; Neutrophil elastase×Insulin-like growth factor-binding protein 7/Alpha-1 antitrypsin; Hyaluronic acid×Immunoglobulin A/Alpha-1 antitrypsin; Neutrophil elastase×Insulin-like growth factor-binding protein 7×Hepatocyte growth factor; Neutrophil elastase×Insulin-like growth factor-binding protein 7×Metalloproteinase inhibitor 2; Neutrophil elastase×Metalloproteinase inhibitor 2/Alpha-1 antitrypsin; Hyaluronic acid×Neutrophil elastase×Hepatocyte growth factor; Neutrophil elastase×Metalloproteinase inhibitor 2×Hepatocyte growth factor, Neutrophil elastase×Serum amyloid P-component/Alpha-1 antitrypsin; Hyaluronic acid×Serum amyloid P-component/Alpha-1 antitrypsin; Neutrophil elastase×Tumor necrosis factor receptor superfamily member 11B/Alpha-1 antitrypsin; Serum amyloid P-component×Insulin-like growth factor-binding protein 7/Alpha-1 antitrypsin; Hyaluronic acid×Neutrophil elastase×Cathepsin D; Hyaluronic acid×Insulin-like growth factor-binding protein 7×Beta-2-glycoprotein-1; Hyaluronic acid×Neutrophil elastase×Serum amyloid P component; Neutrophil elastase×Insulin-like growth factor-binding protein 7×C-C motif chemokine 24; Cathepsin D×Neutrophil elastase×Metalloproteinase inhibitor 2; Hyaluronic acid× Neutrophil elastase×Metalloproteinase inhibitor 2; Hyaluronic acid×Insulin-like growth factor-binding protein 7×Metalloproteinase inhibitor 2; Neutrophil elastase×Hepatocyte growth factor, Insulin-like growth factor-binding protein 7×Hepatocyte growth factor, Insulin-like growth factor-binding protein 7×CXCL-1-2 and -3; Neutrophil elastase×Tumor necrosis factor receptor superfamily member 11B. In these functions, the operators "×" and "/" refer to multiplication and division, respectively. Reference to "-" in the foregoing is as part of a biomarker name, and is not intended to refer to subtraction.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold; relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value.

For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing, about to undergo, or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to, or a subject with a condition for which administration is indicated of, one or more nephrotoxic agents (such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin) are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF; or because administration of a nephrotoxic agent or performance of a nephrotoxic medical procedure is indicated, and the artisan desires a pre-treatment rish analysis.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay results, for example comprising one, two, three, or more measured concentrations of markers selected from the group consisting of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of ari injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s) is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay results, for example one, two, three, or more measured concentrations of markers selected from the group consisting of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay results, for example one, two, three, or more measured concentrations of markers selected from the group consisting of Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, and Macrophage colony-stimulating factor 1 are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test or combination of tests to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different-body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, Hyaluronic acid, Immunoglobulin A, Immunoglobulin G1, Immunoglobulin G2, Insulin-like growth factor-binding protein 7, Alpha-1 antitrypsin, Serum amyloid P component, Metalloproteinase inhibitor 2, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain (P01589), Insulin-like growth factor-binding protein 3, and Macrophage colony-stimulating factor 1, or one or more markers related thereto, are combined with one another and/or with one or more additional markers or clinical indicia, and the combination correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq 8.8$ µmol/L), a percentage increase in serum creatinine of greater than or equal to 20% (1.2-fold from baseline), or a reduction in urine output (documented oliguria of less than 0.5 m/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq 26.4$ µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

The following is a list of markers finding use in the present invention. Where applicable, the Swiss-Prot entry number of the human precursor is indicated in parenthesis:

Hyaluronic acid (not a polypeptide antigen), Immunoglobulin A, Immunoglobulin G1, Immunoglobulin G2, Insulin-like growth factor-binding protein 7 (Q16270), Alpha-1 antitrypsin (P01009), Serum amyloid P component (P02743), Metalloproteinase inhibitor 2 (P16035), Hepatocyte growth factor (P14210), Beta-2-glycoprotein 1 (P02749), Interleukin-1 beta (P01584), Intercellular adhesion molecule 1 (P05362), Neutrophil Elastase (P08246), Tumor necrosis factor receptor superfamily member 11B (O00300), Interleukin-11 (P20809), Cathepsin D (P07339), C-C motif chemokine 24 (O00175), C-X-C motif chemokine 6 (P80162), C-C motif chemokine 13 (Q99616), C-X-C motif chemokines-1 (P09341), -2 (P19875), and -3 (P19876), Matrilysin (P09237), Interleukin-2 receptor alpha chain (P01589), Insulin-like growth factor-binding protein 3 (P17936), Macrophage colony-stimulating factor 1 (P09603).

As used herein, a reference to a marker is intended to refer to one or more polypeptides present in a biological sample that are derived from the marker's precursor and that are of a sufficient length for detection in a specific binding assay as an indication of the marker's presence in the sample. In the case of immunoassays, this typically means a polypeptide of at least 8 amino acids (the length of a typical epitope). The skilled artisan understands that proteins are often post-translationally processed into biologically active "mature" polypeptides. The skilled artisan also understands that the signals obtained from specific binding assays (e.g., an immunoassay) are a result of complexes formed between one or more binding species (e.g., antibodies) and those polypeptides derived from the target biomolecule (i.e., the analyte) containing the necessary epitope(s) to which the antibodies bind.

While such assays may detect the full length biomarker and the assay result be expressed as a concentration of a biomarker of interest, the signal from the assay is actually a result of all such "immunoreactive" polypeptides present in the sample. In the case of C-X-C motif chemokines-1, -2, and -3 for example, sufficient sequence identity exists such that one can use an assay which detects each of C-X-C motif chemokine 1 (P09341), C-X-C motif chemokine 2 (P19875), and C-X-C motif chemokine 3 (P19876). Expression of biomarkers may also be determined by means other than immunoassays, including protein measurements (such as dot blots, western blots, chromatographic methods, mass spectrometry, etc.) and nucleic acid measurements (mRNA quantitation). This list is not meant to be limiting. Preferably an assay for use in the present method detects the mature marker; meaning in the case of a soluble protein, the protein without its secretory signal sequence, and in the case of a marker which is a membrane protein, a soluble form thereof.

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), Agro-Gel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Alternatives to antibodies as binding species in assays are well known in the art. These include natural receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities. Exemplary aptamers are described, for example, in Ostroff et al., J. Proteomics 73: 649-66, 2010; DiGiusto et al., ChemBioChem 7: 535-44, 2006; Miyakawa et al., RNA 14: 1154-63, 2008; Charlton et al., Biochemistry 36: 3018-26, 1997; Gold et al., Nature Proceedings: hdl: 10101/npre.2010.4538.1, 2010.

Antibodies or other binding moieties used in the assays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor 1 (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); C-C MOTIF CHEMOKINE 2 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Tumor necrosis factor receptor superfamily member 11B (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member IA (sTNFR-I, P19438); Soluble tumor necrosis factor receptor superfamily member IB (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, gender, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, chronic lung disease, acute lung injury, HIV infection, volume depletion, hypotension, shock, or sepsis; actual drug exposure or drug exposure being contemplated for subject for purposes of diagnosis or treatment (nonlimiting list of common nephrotoxic agents associated with acute renal failure (Source: Critical Care Nephrology, 2nd ed, Eds: Ronco, Bellomo, Kellum, p. 169 Table 30-1, Saunders/Elsevier publisher): Amphotericin B, Angiotensin-converting enzyme inhibitors and angiotensin receptor blockers, Calcineurin inhibitors, Nonsteroidal anti-inflammatory drugs (NSAIDs), Radiocontrast agents, Acyclovir, Aminoglycosides, Carbamazepine, Carboplatin, Cidofovir, Cisplatin, Foscarnet, Ifosfamide, Vancomycin, Allopurinol, Cephalosporins, Cimetidine, Cytosine arabinoside, Furosemide, Penicillins, Phenytoin, Proton pump inhibitors, Quinolones, Rifampicin, Sulfonamides, Thiazide, Indinavir, Methotrexate, Sulfonamides, Triamterene, Clopidogrel, Gemcitabine, Mitomycin C, Quinine/quinidine, Rapamycin, Ticlopidine, Dextran, Hydroxyethyl starch, Immunoglobulins, Mannitol, Sucrose); clinical variables (e.g., blood pressure, temperature, respiration rate); risk scores (APACHE score, PREDICT score, TIMI Risk Score for UA/NSTEMI, Framingham Risk Score, Simplified Acute Physiology score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)); other clinical measurements (a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, and/or a renal failure index calculated as urine sodium/(urine creatinine/plasma creatinine)). Other measures of renal function which may be combined with the kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 $m^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-}corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, NJ, 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria
  males and females 18 years of age or older;
  undergoing a radiographic/angiographic procedure (such as a CT scan or coronary intervention) involving the intravascular administration of contrast media;
  expected to be hospitalized for at least 48 hours after contrast administration.
  able and willing to provide written informed consent for study participation and to comply with all study procedures.

Exclusion Criteria
  renal transplant recipients;
  acutely worsening renal function prior to the contrast procedure;
  already receiving dialysis (either acute or chronic) or in imminent need of dialysis at enrollment;
  expected to undergo a major surgical procedure (such as involving cardiopulmonary bypass) or an additional imaging procedure with contrast media with significant risk for further renal insult within the 48 hrs following contrast administration;
  participation in an interventional clinical study with an experimental therapy within the previous 30 days;
  known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, CA. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m²=2 points, 20-40 mL/min/1.73 m²=4 points, <20 mL/min/1.73 m²=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2: Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
  males and females 18 years of age or older;
  undergoing cardiovascular surgery;
  Toronto/Ottawa Predictive Risk Index for Renal Replacement risk score of at least 2 (Wijeysundera et al., JAMA 297: 1801-9, 2007); and
  able and willing to provide written informed consent for study participation and to comply with all study procedures.
Exclusion Criteria
  known pregnancy;
  previous renal transplantation;
  acutely worsening renal function prior to enrollment (e.g., any category of RIFLE criteria);
  already receiving dialysis (either acute or chronic) or in imminent need of dialysis at enrollment;
  currently enrolled in another clinical study or expected to be enrolled in another clinical study within 7 days of cardiac surgery that involves drug infusion or a therapeutic intervention for AKI;
  known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, CA. The study urine samples are frozen and shipped to Astute Medical, Inc.

Example 3: Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
  males and females 18 years of age or older;
Study population 1: approximately 300 patients that have at least one of:
  shock (SBP<90 mmHg and/or need for vasopressor support to maintain MAP>60 mmHg and/or documented drop in SBP of at least 40 mmHg); and
  sepsis;
Study population 2: approximately 300 patients that have at least one of:
  IV antibiotics ordered in computerized physician order entry (CPOE) within 24 hours of enrollment;
  contrast media exposure within 24 hours of enrollment;
  increased Intra-Abdominal Pressure with-acute decompensated heart failure; and
  severe trauma as the primary reason for ICU admission and likely to be hospitalized in the ICU for 48 hours after enrollment;
Study population 3: approximately 300 patients
  expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.
Exclusion Criteria
  known pregnancy;
  institutionalized individuals;
  previous renal transplantation;
  known acutely worsening renal function prior to enrollment (e.g., any category of RIFLE criteria);
  received dialysis (either acute or chronic) within 5 days prior to enrollment or in imminent need of dialysis at the time of enrollment;
  known infection with human immunodeficiency virus (HIV) or a hepatitis virus;
  meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4. Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, CA 92590 and Virginia Medical Research, Inc., 915 First Colonial Rd., Virginia Beach, VA 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, VA 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 5. Kidney Injury Markers for Evaluating Renal Status in Patients

Patients from the intensive care unit (ICU) (Example 3, above) were used in the following analysis. Each patient was classified by kidney status as non-injury (0), risk of injury (R), injury (I), and failure (F) according to the maximum stage reached within 10 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected, except Hyaluronic Acid, which is a binding assay based on the binding protein Aggrecan. The following is a list of commercial assay reagents used for collecting measuring various markers:

| Marker | Assay name/Vendor |
|---|---|
| Hyaluronic acid | Echelon Hyaluronan Enzyme-Linked Immunosorbent Assay Kit, cat. # K1200 |
| Neutrophil Elastase (ELANE) | Hycult/Cell Sciences Elisa kit for human neutrophil elastase, cat. #HK319 |
| Interleukin-1 beta (IL-1b) | MSD[††] Proinflamm 9-IL-1 96-Well MULTI-ARRAY ® and MULTI-SPOT ® Human Cytokine Assays: Base Kit, Cat# K11007C-2 |
| Interleukin-11 (IL-11) | MP Lmx[†] MP63K 9plex-IL-11 Human Cytokine/Chemokine Panel III, cat. # MPXHCYP3-63K |
| C-X-C motif chemokine 6 (GCP-2) | MP Lmx MP63K 9plex-CXCL6 (GCP2) Human Cytokine/Chemokine Panel III, cat. # MPXHCYP3-63K |
| Macrophage colony-stimulating factor 1 (CSF-1) | MP Lmx MP 63K 9plex-M-CSF Human Cytokine/Chemokine Panel III, cat. # MPXHCYP3-63K |
| Intercellular adhesion molecule 1 (ICAM-1) | MP Lmx HNGD3-36K-7plex-sICAM-1 Human Neurodegenerative Disease Panel 3 Kit 96 Well Plate Assay, cat. # HNDG3-36K |
| Cathepsin-D | MP Lmx HNGD3-36K-7plex-Cathepsin D Human Neurodegenerative Disease Panel 3 Kit 96 Well Plate Assay, cat. # HNDG3-36K |
| C-X-C motif chemokines −1, −2, and −3 (CXCL −1, −2, −3) | MP Lmx MP60K-21plex-GRO Human Cytokine/Chemokine Kit 96-Well Plate Assay, cat. # MPXHCYTO-60K |
| Interleukin-2 receptor alpha chain (IL2Ra) | MP Lmx MP60K-21plex-sIL-2Ra Human Cytokine/Chemokine 96-Well Plate Assay, cat. # MPXHCYTO-60K |
| Immunoglobulin A (IgA) | MP Lmx MP HGAM 6 plex-IgA Human Immunoglobulin Isotyping Kit 96 Well Plate Assay, cat. # HGAM-301 |
| Immunoglobulin G1 (IgG1) | MP Lmx MP HGAM 6 plex-IgG1 Human Immunoglobulin Isotyping Kit 96 Well Plate Assay, cat. # HGAM-301 |
| Immunoglobulin G2 (IgG2) | MP Lmx MP HGAM 6 plex-IgG2 Human Immunoglobulin Isotyping Kit 96 Well Plate Assay, cat. # HGAM-301 |
| Alpha-1 antitrypsin (A1AT) | MP Lmx HNDG2-36K 4plex-Alpha 1 anti-Trypsin Human Neurodegenerative Disease Panel 2 Kit, cat. # HNDG2-36K |
| C-C motif chemokine 13 (MCP-4) | MP Lmx MP 62K - 23plex-MCP-4 Human Cytokine/Chemokine Panel II, cat. # MPXHCYP2-62K |
| C-C motif chemokine 24 (Eotaxin-2) | MP Lmx MP 62K - 23plex-Eotaxin-2 Human Cytokine/Chemokine Panel II, cat. # MPXHCYP2-62K |
| Insulin-like growth factor-binding protein 7 (IGFBP7) | MP Lmx HIGFBP-53K-Plex B-3plex-IGFBP-7 Human IGF Binding Protein (IGFBP) Panel Kit, cat. # HIGFBP-53K |
| Insulin-like growth factor-binding protein 3 (IGFBP3) | MP Lmx HIGFBP-53K-Plex B-3plex-IGFBP-3 Human IGF Binding Protein (IGFBP) Panel Kit, cat. # HIGFBP-53K |
| Metalloproteinase inhibitor 2 (TIMP2) | RND Lmx TIMP-2 Human TIMP Multiplex Kit, cat. # LKT003 |
| Matrilysin (MMP-7) | RND Lmx MMP 3plex Urine-MMP-7 Human MMP MultiAnalyte Profiling Base Kit, cat. # LMP000 |
| Serum amyloid P component (SAP) | EMD Lmx CVD5-SAP BeadPlex ® Human CVD Panel 5 (Acute Phase), cat. # BPHCVD05-8 |
| Beta-2-glycoprotein-1 (ApoH) | EMD Lmx CVD1-APO H BeadPlex ® Human CVD Panel 1 (Apolipoproteins), cat. # BPHCVD01-7 |

| Marker | Assay name/Vendor |
| --- | --- |
| Hepatocyte growth factor (HGF) | MSD Human HGF Cat# N05CA-1 |
| Tumor necrosis factor receptor superfamily member 11B (Osteoprotegerin, OPGN) | MSC Human Osteoprotegerin Cat# N05CA-1 |

†LMX indicates an assay run on a Luminex immunoassay platform.
††MSD indicates an assay run on a Meso Scale Discovery immunoassay platform.
Vendor list:
EMD: EMD Chemicals Inc., 480 South Democrat Road, Gibbstown, NJ 08027
MSD: Meso Scale Discovery, 9238 Gaither Road, Gaithersburg, Maryland 20877
MP: Millipore Inc., 290 Concord Road, Billerica, MA 01821
RND: R&D Systems, Inc., 614 McKinley Place NE Minneapolis, MN 55413
Echelon: Echelon Biosciences Inc., 675 Arapeen Drive, Suite 302, Salt Lake City, UT 84108
Hycult: Hycult Biotech Inc., 600 West Germantown Pike, Suite 400, Plymouth Meeting, PA 1946

Concentrations were reported as follows: Hyaluronic acid—ng/mL, Immunoglobulin A—ng/mL, Immunoglobulin G1—ng/mL, Immunoglobulin G2—ng/mL, Insulin-like growth factor-binding protein 7—ng/mL, Alpha-1 antitrypsin—ng/mL, Serum amyloid P component—ng/mL, Metalloproteinase inhibitor 2—pg/mL, Hepatocyte growth factor—pg/mL, Beta-2-glycoprotein 1—ng/mL, Interleukin-1 beta—pg/mL, Neutrophil Elastase—ng/mL, Tumor necrosis factor receptor superfamily member 11B—pg/mL, Interleukin-11—pg/mL, Intercellular adhesion molecule 1—pg/mL, Cathepsin D—pg/mL, C-C motif chemokine 24—pg/mL, C-X-C motif chemokine 6—pg/mL, C-C motif chemokine 13—pg/mL, C-X-C motif chemokines-4—pg/mL, -2—pg/mL, and -3—pg/mL, Matrilysin—pg/mL, Interleukin-2 receptor alpha chain—pg/mL, Insulin-like growth factor=binding protein 3—ng/mL, and Macrophage colony-stimulating factor 1—pg/mL. With the exception of Alpha-1 antitrypsin, the concentration of which was reduced in the context of AKI relative to control subjects using the foregoing assay, the concentrations of all markers were increased in the context of AKI relative to control subjects using the foregoing assays.

Two cohorts were defined as described in the introduction to each of the following tables. In the following tables, the time "prior to AKI stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) was determined. Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage was used.

The individual marker assay results were combined to provide a single result as indicated below, and the single result treated as an individual biomarker using standard statistical methods. Two exemplary methods for combining marker results are presented in the following tables. In one, referred to in the following tables as the "product model," arithmetic operators such as "×" (multiplication) and "/" (division) were used in their ordinary sense to combine the measured marker levels. In the second, referred to in the following tables as the "logistic regression model," a well known logistic regression method was used. Logistic regression is a method widely used for models which have a binary outcome, such as the "diseased" "non-diseased" dichotomy presented here. The method will be briefly described below, full treatments can be found in the literature. The model used was:

$$\Pi_i(y_i = 1 \mid x_i) = \frac{e^{\alpha + \beta x_i}}{1 + e^{\alpha + \beta x_i}}$$

In this model, x and β are vectors, x representing the different observables or analyte values, $y_i=1$ indicates a diseased state, and $\Pi_i$ is the model probability of this state for the $i^{th}$ case given $x_i$. The panel value for each sample is $\Pi_i$. The log odds or logit is:

$$logit = \ln\left[\frac{\Pi_i(y_i = 1 \mid x_i)}{1 - \Pi_i(y_i = 1 \mid x_i)}\right] = \alpha + \beta x_i$$

Define $p_i$ as probability of observing the true outcome:

$$p_i = \begin{cases} \Pi_i(y_i = 1 \mid x_i) & \text{if deseased} \\ 1 - \Pi_i(y_i = 1 \mid x_i) & \text{if non-diseased} \end{cases}$$

The likelihood function is the product of the probabilities of observing the true outcomes, so the log likelihood (LL) is:

$$LL = \ln(L(\alpha, \beta)) = \Sigma \ln(p_i)$$

To find the parameters, α and β, that best fit the model, the negative log likelihood (−LL) is minimized. This minimization was performed using the Levenberg-Marquardt method (Numerical Recipes The Art of Scientific Computing, Third Edition, Cambridge University Press, 2007). The initial point for each parameter is 0.

A commonly used statistic to compare the fit of two nested models is the likelihood ratio test. This statistic, or the deviance, is the difference in twice the negative log likelihood (−2LL) for the two model, and is asymptotically a $\chi^2$ distribution with DF equal to the change in the number of degrees of freedom (number of analytes) between the models. The p-value is calculated from this statistic. The null hypothesis is that the logistic model is not different than a constant model (β set to 0), is tested for each model using the likelihood ratio test. The 'model p-value' is defined as the probability that the null hypothesis is true. For the constant model, a closed form solution for a and −2LL can be found. It is a function of the number of diseased (#D) and the number of non-diseased (#ND) samples in the data set.

$$\alpha = \ln\left(\frac{\#D}{\#ND}\right)$$

$$-2LL = -2 * [\#ND \ \ln(1-\Pi) + \#D \ \ln(\Pi)]$$

Where: $\Pi = \frac{\#D}{(\#ND + \#D)}$

The ability to distinguish cohort 1 from Cohort 2 was determined using ROC analysis. Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test, and are reported in the following Tables 1-12 as "−" if p<0.05, and as "+" if p≥0.05. All panels reported in Tables 1-12 below are calculated to increase in value in "disease" as compared to "control".

The comparisons reported in the tables are:
A: Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.
B: Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.
C: Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.
D: Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.
E: Comparison of marker levels in enrollment urine samples collected from Cohort 1 (patients that did not progress beyond RIFLE stage 0 or R within 48 hrs) and in enrollment urine samples collected from Cohort 2 (subjects reaching RIFLE stage I or F within 48 hrs). Enrollment samples from patients already at RIFLE stage I or F were included in Cohort 2.

TABLE 1

Significance of exemplary two marker panels; product model; "−" if p < 0.05, and as "+" if p ≥ 0.05

| | | 24 hrs prior to AKI stage | | | | | | | | | | |
|---|---|---|---|---|---|---|---|---|---|---|---|---|
| | | sCr | | | | sCr_UO | | | | UO | | |
| | Panel | Analysis | | | | | | | | | | |
| | # | A | B | C | D | A | B | C | D | A | B | C | D |
| Cathepsin D × Metalloproteinase inhibitor 2 | 1 | − | − | − | − | − | − | − | − | − | − | − | − |
| Hyaluronic acid × Interleukin-11 | 2 | − | − | − | − | − | − | − | − | − | − | − | − |
| C-C motif chemokine 13 × Metalloproteinase inhibitor 2 | 3 | − | − | − | − | − | − | − | − | − | − | − | − |
| Interleukin-11 × Metalloproteinase inhibitor 2 | 4 | − | − | − | − | − | − | − | − | − | − | − | − |
| Neutrophil elastase × Immunoglobulin G2 | 5 | − | − | − | − | − | − | − | − | − | − | − | − |
| Hyaluronic acid × Immunoglobulin G1 | 6 | − | − | − | − | − | − | − | − | − | − | − | − |
| C-C motif chemokine 13 × Hepatocyte growth factor | 7 | − | − | − | − | − | − | − | − | − | − | − | − |
| Neutrophil elastase × C-X-C motif chemokine 6 | 8 | + | − | − | − | − | − | − | − | − | − | − | − |
| Insulin-like growth factor-binding protein 7 × Interleukin-1 beta | 9 | − | − | − | − | − | − | − | − | − | − | − | − |
| Neutrophil elastase × C-C motif chemokine 24 | 10 | − | − | − | − | − | − | − | − | − | − | − | − |
| Hyaluronic acid/(Alpha-1 antitrypsin) | 11 | − | − | − | − | − | − | − | − | − | − | − | − |
| Insulin-like growth factor-binding protein 7 × C-C motif chemokine 24 | 12 | − | − | − | − | − | − | − | − | − | − | − | − |
| Neutrophil elastase × Immunoglobulin A | 13 | + | − | − | − | − | − | − | − | − | − | − | − |
| Immunoglobulin G1 × Metalloproteinase inhibitor 2 | 14 | − | − | − | − | − | − | − | − | − | − | − | − |
| Insulin-like growth factor-binding protein 7 × C-X-C motif chemokine 6 | 15 | − | − | − | − | − | − | − | − | − | − | − | − |
| Neutrophil elastase/(Alpha-1 antitrypsin) | 16 | − | − | − | − | − | − | − | − | − | − | − | − |
| Hyaluronic acid × Beta-2-glycoprotein 1 | 17 | − | − | − | − | − | − | − | − | − | − | − | − |
| Serum amyloid P-component/(Alpha-1 antitrypsin) | 18 | − | − | − | − | − | − | − | − | − | − | − | − |
| Insulin-like growth factor-binding protein 7 × Cathepsin D | 19 | − | − | − | − | − | − | − | − | − | − | − | − |
| Neutrophil elastase × Beta-2-glycoprotein 1 | 20 | + | − | − | − | − | − | − | − | − | − | − | − |
| Serum amyloid P-component × Insulin-like growth factor-binding protein 7 | 21 | − | − | − | − | − | − | − | − | − | − | − | − |
| Hyaluronic acid × Metalloproteinase inhibitor 2 | 22 | − | − | − | − | − | − | − | − | − | − | − | − |

TABLE 1-continued

Significance of exemplary two marker panels; product model; "−" if p < 0.05, and as "+" if p ≥ 0.05

| | | 24 hrs prior to AKI stage | | | | | | | | | | | |
|---|---|---|---|---|---|---|---|---|---|---|---|---|---|
| | | sCr | | | | sCr_UO Analysis | | | | UO | | | |
| Panel | # | A | B | C | D | A | B | C | D | A | B | C | D |
| C-X-C motif chemokines (−1, −2, −3) × Metalloproteinase inhibitor 2 | 23 | − | − | − | − | − | − | − | − | − | − | − | − |
| Immunoglobulin A/(Alpha-1 antitrypsin) | 24 | − | − | − | − | − | − | − | − | − | − | − | − |
| Neutrophil elastase × Metalloproteinase inhibitor 2 | 25 | − | − | − | − | − | − | − | − | − | − | − | − |
| Neutrophil elastase × Hepatocyte growth factor | 26 | − | − | − | − | − | − | − | − | − | − | − | − |
| Hyaluronic acid × Immunoglobulin A | 27 | − | − | − | − | − | − | − | − | − | − | − | − |
| Insulin-like growth factor-binding protein 7 × Immunoglobulin A | 28 | − | − | − | − | − | − | − | − | − | − | − | − |
| Hyaluronic acid × Neutrophil elastase | 29 | + | − | − | − | − | − | − | − | − | − | − | − |
| Neutrophil elastase × C-X-C motif chemokines (−1, −2, −3) | 30 | − | − | − | − | − | − | − | − | − | − | − | − |
| Neutrophil elastase × Cathepsin D | 31 | + | − | − | − | − | − | − | − | − | − | − | − |
| Metalloproteinase inhibitor 2 × Hepatocyte growth factor | 32 | − | − | − | − | − | − | − | − | − | − | − | − |
| Hyaluronic acid × Insulin-like growth factor-binding protein 7 | 33 | − | − | − | − | − | − | − | − | − | − | − | − |
| Serum amyloid P-component × Metalloproteinase inhibitor 2 | 34 | − | − | − | − | − | − | − | − | − | − | − | − |
| Immunoglobulin A × Metalloproteinase inhibitor 2 | 35 | − | − | − | − | − | − | − | − | − | − | − | − |
| Neutrophil elastase × Serum amyloid P-component | 36 | − | − | − | − | − | − | − | − | − | − | − | − |
| Insulin-like growth factor-binding protein 7/(Alpha-1 antitrypsin) | 37 | − | − | − | − | − | − | − | − | − | − | − | − |
| Insulin-like growth factor-binding protein 7 × Metalloproteinase inhibitor 2 | 38 | − | − | − | − | − | − | − | − | − | − | − | − |
| Hyaluronic acid × Serum amyloid P-component | 39 | − | − | − | − | − | − | − | − | − | − | − | − |
| Neutrophil elastase × Tumor necrosis factor receptor superfamily member 11B | 40 | − | − | − | − | − | − | − | − | − | − | − | − |
| Neutrophil elastase × Insulin-like growth factor-binding protein 7 | 41 | − | − | − | − | − | − | − | − | − | − | − | − |
| Hyaluronic acid × C-X-C motif chemokines (−1, −2, −3) | 42 | − | − | − | − | − | − | − | − | − | − | − | − |
| Insulin-like growth factor-binding protein 7 × Immunoglobulin G1 | 43 | − | − | − | − | − | − | − | − | − | − | − | − |
| Insulin-like growth factor-binding protein 7 × Hepatocyte growth factor | 44 | − | − | − | − | − | − | − | − | − | − | − | − |
| Hepatocyte growth factor/(Alpha-1 antitrypsin) | 45 | − | − | − | − | − | − | − | − | − | − | − | − |
| Insulin-like growth factor-binding protein 7 × Interleukin-11 | 46 | − | − | − | − | − | − | − | − | − | − | − | − |
| Beta-2-glycoprotein 1 × Insulin-like growth factor-binding protein 7 | 47 | − | − | − | − | − | − | − | − | − | − | − | − |
| Beta-2-glycoprotein 1 × Metalloproteinase inhibitor 2 | 48 | − | − | − | − | − | − | − | − | − | − | − | − |
| Hyaluronic acid × C-C motif chemokine 13 | 49 | − | − | − | − | − | − | − | − | − | − | − | − |
| Insulin-like growth factor-binding protein 7 × C-X-C motif chemokines (−1, −2, −3) | 50 | − | − | − | − | − | − | − | − | − | − | − | − |
| Insulin-like growth factor-binding protein 7 × C-C motif chemokine 13 | 51 | − | − | − | − | − | − | − | − | − | − | − | − |

TABLE 2

Significance of exemplary two marker panels; logistic regression model, "−" if p < 0.05, and as "+" if p ≥ 0.05

| | | 24 hrs prior to AKI stage | | | | | | | | | | | |
|---|---|---|---|---|---|---|---|---|---|---|---|---|---|
| | | sCr | | | | sCr_UO Analysis | | | | UO | | | |
| Panel | # | A | B | C | D | A | B | C | D | A | B | C | D |
| Cathepsin D; Metalloproteinase inhibitor 2 | 1 | − | − | − | − | − | − | − | − | − | − | − | − |
| Hyaluronic acid; Interleukin-11 | 2 | − | − | − | − | − | − | − | − | − | − | − | − |
| C-C motif chemokine 13; Metalloproteinase inhibitor 2 | 3 | − | − | − | − | − | − | − | − | − | − | − | − |
| Interleukin-11; Metalloproteinase inhibitor 2 | 4 | − | − | − | − | − | − | − | − | − | − | − | − |
| Neutrophil elastase; Immunoglobulin G2 | 5 | − | − | − | − | − | − | − | − | − | − | − | − |
| Hyaluronic acid; Immunoglobulin G1 | 6 | − | − | − | − | − | − | − | − | − | − | − | − |
| C-C motif chemokine 13; Hepatocyte growth factor | 7 | − | − | − | − | − | − | − | − | − | − | − | − |
| Neutrophil elastase; C-X-C motif chemokine 6 | 8 | + | − | − | − | − | − | − | − | − | − | − | − |
| Insulin-like growth factor-binding protein 7; Interleukin-1 beta | 9 | − | − | − | − | − | − | − | − | − | − | − | − |
| Neutrophil elastase; C-C motif chemokine 24 | 10 | − | − | − | − | − | − | − | − | − | − | − | − |
| Hyaluronic acid; (Alpha-1 antitrypsin) | 11 | − | − | − | − | − | − | − | − | − | − | − | − |

TABLE 2-continued

Significance of exemplary two marker panels; logistic regression model, "−" if p < 0.05, and as "+" if p ≥ 0.05

| | | 24 hrs prior to AKI stage | | | | | | | | | | | |
|---|---|---|---|---|---|---|---|---|---|---|---|---|---|
| | | sCr | | | | sCr_UO | | | | UO | | | |
| | Panel | | | | | Analysis | | | | | | | |
| | # | A | B | C | D | A | B | C | D | A | B | C | D |
| Insulin-like growth factor-binding protein 7; C-C motif chemokine 24 | 12 | − | − | − | − | − | − | − | − | − | − | − | − |
| Neutrophil elastase; Immunoglobulin A | 13 | − | − | − | − | − | − | − | − | − | − | − | − |
| Immunoglobulin G1; Metalloproteinase inhibitor 2 | 14 | − | − | − | − | − | − | − | − | − | − | − | − |
| Insulin-like growth factor-binding protein 7; C-X-C motif chemokine 6 | 15 | − | − | − | − | − | − | − | − | − | − | − | − |
| Neutrophil elastase; (Alpha-1 antitrypsin) | 16 | − | − | − | − | − | − | − | − | − | − | − | − |
| Hyaluronic acid; Beta-2-glycoprotein 1 | 17 | − | − | − | − | − | − | − | − | − | − | − | − |
| Serum amyloid P-component; (Alpha-1 antitrypsin) | 18 | − | − | − | − | − | − | − | − | − | − | − | − |
| Insulin-like growth factor-binding protein 7; Cathepsin D | 19 | − | − | − | − | − | − | − | − | − | − | − | − |
| Neutrophil elastase; Beta-2-glycoprotein 1 | 20 | + | − | − | − | − | − | − | − | − | − | − | − |
| Serum amyloid P-component; Insulin-like growth factor-binding protein 7 | 21 | − | − | − | − | − | − | − | − | − | − | − | − |
| Hyaluronic acid; Metalloproteinase inhibitor 2 | 22 | − | − | − | − | − | − | − | − | − | − | − | − |
| C-X-C motif chemokines (−1, −2, −3); Metalloproteinase inhibitor 2 | 23 | − | − | − | − | − | − | − | − | − | − | − | − |
| Immunoglobulin A; (Alpha-1 antitrypsin) | 24 | − | − | − | − | − | − | − | − | − | − | − | − |
| Neutrophil elastase; Metalloproteinase inhibitor 2 | 25 | − | − | − | − | − | − | − | − | − | − | − | − |
| Neutrophil elastase; Hepatocyte growth factor | 26 | − | − | − | − | − | − | − | − | − | − | − | − |
| Hyaluronic acid; Immunoglobulin A | 27 | − | − | − | − | − | − | − | − | − | − | − | − |
| Insulin-like growth factor-binding protein 7; Immunoglobulin A | 28 | − | − | − | − | − | − | − | − | − | − | − | − |
| Hyaluronic acid; Neutrophil elastase | 29 | − | − | − | − | − | − | − | − | − | − | − | − |
| Neutrophil elastase; C-X-C motif chemokines (−1, −2, −3) | 30 | − | − | − | − | − | − | − | − | − | − | − | − |
| Neutrophil elastase; Cathepsin D | 31 | − | − | − | − | − | − | − | − | − | − | − | − |
| Metalloproteinase inhibitor 2; Hepatocyte growth factor | 32 | − | − | − | − | − | − | − | − | − | − | − | − |
| Hyaluronic acid; Insulin-like growth factor-binding protein 7 | 33 | − | − | − | − | − | − | − | − | − | − | − | − |
| Serum amyloid P-component; Metalloproteinase inhibitor 2 | 34 | − | − | − | − | − | − | − | − | − | − | − | − |
| Immunoglobulin A; Metalloproteinase inhibitor 2 | 35 | − | − | − | − | − | − | − | − | − | − | − | − |
| Neutrophil elastase; Serum amyloid P-component | 36 | − | − | − | − | − | − | − | − | − | − | − | − |
| Insulin-like growth factor-binding protein 7; (Alpha-1 antitrypsin) | 37 | − | − | − | − | − | − | − | − | − | − | − | − |
| Insulin-like growth factor-binding protein 7; Metalloproteinase inhibitor 2 | 38 | − | − | − | − | − | − | − | − | − | − | − | − |
| Hyaluronic acid; Serum amyloid P-component | 39 | − | − | − | − | − | − | − | − | − | − | − | − |
| Neutrophil elastase; Tumor necrosis factor receptor superfamily member 11B | 40 | − | − | − | − | − | − | − | − | − | − | − | − |
| Neutrophil elastase; Insulin-like growth factor-binding protein 7 | 41 | − | − | − | − | − | − | − | − | − | − | − | − |
| Hyaluronic acid; C-X-C motif chemokines (−1, −2, −3) | 42 | − | − | − | − | − | − | − | − | − | − | − | − |
| Insulin-like growth factor-binding protein 7; Immunoglobulin G1 | 43 | − | − | − | − | − | − | − | − | − | − | − | − |
| Insulin-like growth factor-binding protein 7; Hepatocyte growth factor | 44 | − | − | − | − | − | − | − | − | − | − | − | − |
| Hepatocyte growth factor; (Alpha-1 antitrypsin) | 45 | − | − | − | − | − | − | − | − | − | − | − | − |
| Insulin-like growth factor-binding protein 7; Interleukin-11 | 46 | − | − | − | − | − | − | − | − | − | − | − | − |
| Beta-2-glycoprotein 1; Insulin-like growth factor-binding protein 7 | 47 | − | − | − | − | − | − | − | − | − | − | − | − |
| Beta-2-glycoprotein 1; Metalloproteinase inhibitor 2 | 48 | − | − | − | − | − | − | − | − | − | − | − | − |
| Hyaluronic acid; C-C motif chemokine 13 | 49 | − | − | − | − | − | − | − | − | − | − | − | − |
| Insulin-like growth factor-binding protein 7; C-X-C motif chemokines (−1, −2, −3) | 50 | − | − | − | − | − | − | − | − | − | − | − | − |
| Insulin-like growth factor-binding protein 7; C-C motif chemokine 13 | 51 | − | − | − | − | − | − | − | − | − | − | − | − |

TABLE 3

Significance of exemplary two marker panels, analysis E; product model

| | Panel # | Analysis | sCr E | sCr_UO E | UO E |
|---|---|---|---|---|---|
| Cathepsin D × Metalloproteinase inhibitor 2 | 1 | Z | − | − | − |
| Hyaluronic acid × Interleukin-11 | 2 | | − | − | − |
| C-C motif chemokine 13 × Metalloproteinase inhibitor 2 | 3 | | − | − | − |

TABLE 3-continued

Significance of exemplary two marker panels, analysis E; product model

| | Panel # | Analysis | sCr E | sCr_UO E | UO E |
|---|---|---|---|---|---|
| Interleukin-11 × Metalloproteinase inhibitor 2 | 4 | | − | − | − |
| Neutrophil elastase × Immunoglobulin G2 | 5 | | − | − | − |
| Hyaluronic acid × Immunoglobulin G1 | 6 | | − | − | − |
| C-C motif chemokine 13 × Hepatocyte growth factor | 7 | | − | − | − |
| Neutrophil elastase × C-X-C motif chemokine 6 | 8 | | + | − | − |
| Insulin-like growth factor-binding protein 7 × Interleukin-1 beta | 9 | | − | − | − |
| Neutrophil elastase × C-C motif chemokine 24 | 10 | | − | − | − |
| Hyaluronic acid/(Alpha-1 antitrypsin) | 11 | | − | − | − |
| Insulin-like growth factor-binding protein 7 × C-C motif chemokine 24 | 12 | | − | − | − |
| Neutrophil elastase × Immunoglobulin A | 13 | | + | − | − |
| Immunoglobulin G1 × Metalloproteinase inhibitor 2 | 14 | | − | − | − |
| Insulin-like growth factor-binding protein 7 × C-X-C motif chemokine 6 | 15 | | − | − | − |
| Neutrophil elastase/(Alpha-1 antitrypsin) | 16 | | − | − | − |
| Hyaluronic acid × Beta-2-glycoprotein 1 | 17 | | − | − | − |
| Serum amyloid P-component/(Alpha-1 antitrypsin) | 18 | | − | − | − |
| Insulin-like growth factor-binding protein 7 × Cathepsin D | 19 | | − | − | − |
| Neutrophil elastase × Beta-2-glycoprotein 1 | 20 | | − | − | − |
| Serum amyloid P-component × Insulin-like growth factor-binding protein 7 | 21 | | − | − | − |
| Hyaluronic acid × Metalloproteinase inhibitor 2 | 22 | | − | − | − |
| C-X-C motif chemokines (−1, −2, −3) × Metalloproteinase inhibitor 2 | 23 | | − | − | − |
| Immunoglobulin A/(Alpha-1 antitrypsin) | 24 | | − | − | − |
| Neutrophil elastase × Metalloproteinase inhibitor 2 | 25 | | − | − | − |
| Neutrophil elastase × Hepatocyte growth factor | 26 | | − | − | − |
| Hyaluronic acid × Immunoglobulin A | 27 | | − | − | − |
| Insulin-like growth factor-binding protein 7 × Immunoglobulin A | 28 | | − | − | − |
| Hyaluronic acid × Neutrophil elastase | 29 | | + | − | − |
| Neutrophil elastase × C-X-C motif chemokines (−1, −2, −3) | 30 | | − | − | − |
| Neutrophil elastase × Cathepsin D | 31 | | + | − | − |
| Metalloproteinase inhibitor 2 × Hepatocyte growth factor | 32 | | − | − | − |
| Hyaluronic acid × Insulin-like growth factor-binding protein 7 | 33 | | − | − | − |
| Serum amyloid P-component × Metalloproteinase inhibitor 2 | 34 | | − | − | − |
| Immunoglobulin A × Metalloproteinase inhibitor 2 | 35 | | − | − | − |
| Neutrophil elastase × Serum amyloid P-component | 36 | | − | − | − |
| Insulin-like growth factor-binding protein 7/(Alpha-1 antitrypsin) | 37 | | − | − | − |
| Insulin-like growth factor-binding protein 7 × Metalloproteinase inhibitor 2 | 38 | | − | − | − |
| Hyaluronic acid × Serum amyloid P-component | 39 | | − | − | − |
| Neutrophil elastase × Tumor necrosis factor receptor superfamily member 11B | 40 | | − | − | − |
| Neutrophil elastase × Insulin-like growth factor-binding protein 7 | 41 | | − | − | − |
| Hyaluronic acid × C-X-C motif chemokines (−1, −2, −3) | 42 | | − | − | − |
| Insulin-like growth factor-binding protein 7 × Immunoglobulin G1 | 43 | | − | − | − |
| Insulin-like growth factor-binding protein 7 × Hepatocyte growth factor | 44 | | − | − | − |
| Hepatocyte growth factor/(Alpha-1 antitrypsin) | 45 | | − | − | − |
| Insulin-like growth factor-binding protein 7 × Interleukin-11 | 46 | | − | − | − |
| Beta-2-glycoprotein 1 × Insulin-like growth factor-binding protein 7 | 47 | | − | − | − |
| Beta-2-glycoprotein 1 × Metalloproteinase inhibitor 2 | 48 | | − | − | − |
| Hyaluronic acid × C-C motif chemokine 13 | 49 | | − | − | − |
| Insulin-like growth factor-binding protein 7 × C-X-C motif chemokines (−1, −2, −3) | 50 | | − | − | − |
| Insulin-like growth factor-binding protein 7 × C-C motif chemokine 13 | 51 | | − | − | − |

TABLE 4

Significance of exemplary two marker panels, analysis E; logistic regression model, "−" if p < 0.05, and as "+" if p ≥ 0.05

| Marker Panel | Panel # | Analysis | sCr E | sCr_UO E | UO E |
|---|---|---|---|---|---|
| Cathepsin D; Metalloproteinase inhibitor 2 | 1 | Z | − | − | − |
| Hyaluronic acid; Interleukin-11 | 2 | | − | − | − |
| C-C motif chemokine 13; Metalloproteinase inhibitor 2 | 3 | | − | − | − |
| Interleukin-11; Metalloproteinase inhibitor 2 | 4 | | − | − | − |
| Neutrophil elastase; Immunoglobulin G2 | 5 | | − | − | − |
| Hyaluronic acid; Immunoglobulin G1 | 6 | | − | − | − |
| C-C motif chemokine 13; Hepatocyte growth factor | 7 | | − | − | − |
| Neutrophil elastase; C-X-C motif chemokine 6 | 8 | | − | − | − |
| Insulin-like growth factor-binding protein 7; Interleukin-1 beta | 9 | | − | − | − |
| Neutrophil elastase; C-C motif chemokine 24 | 10 | | − | − | − |
| Hyaluronic acid; (Alpha-1 antitrypsin) | 11 | | − | − | − |
| Insulin-like growth factor-binding protein 7; C-C motif chemokine 24 | 12 | | − | − | − |
| Neutrophil elastase; Immunoglobulin A | 13 | | + | − | − |
| Immunoglobulin G1; Metalloproteinase inhibitor 2 | 14 | | − | − | − |
| Insulin-like growth factor-binding protein 7; C-X-C motif chemokine 6 | 15 | | − | − | − |
| Neutrophil elastase; (Alpha-1 antitrypsin) | 16 | | − | − | − |
| Hyaluronic acid; Beta-2-glycoprotein 1 | 17 | | − | − | − |
| Serum amyloid P-component; (Alpha-1 antitrypsin) | 18 | | − | − | − |
| Insulin-like growth factor-binding protein 7; Cathepsin D | 19 | | − | − | − |
| Neutrophil elastase; Beta-2-glycoprotein 1 | 20 | | − | − | − |
| Serum amyloid P-component; Insulin-like growth factor-binding protein 7 | 21 | | − | − | − |
| Hyaluronic acid; Metalloproteinase inhibitor 2 | 22 | | − | − | − |
| C-X-C motif chemokines (−1, −2, −3); Metalloproteinase inhibitor 2 | 23 | | − | − | − |
| Immunoglobulin A; (Alpha-1 antitrypsin) | 24 | | − | − | − |
| Neutrophil elastase; Metalloproteinase inhibitor 2 | 25 | | − | − | − |
| Neutrophil elastase; Hepatocyte growth factor | 26 | | − | − | − |
| Hyaluronic acid; Immunoglobulin A | 27 | | − | − | − |
| Insulin-like growth factor-binding protein 7; Immunoglobulin A | 28 | | − | − | − |
| Hyaluronic acid; Neutrophil elastase | 29 | | − | − | − |
| Neutrophil elastase; C-X-C motif chemokines (−1, −2, −3) | 30 | | − | − | − |
| Neutrophil elastase; Cathepsin D | 31 | | − | − | − |
| Metalloproteinase inhibitor 2; Hepatocyte growth factor | 32 | | − | − | − |
| Hyaluronic acid; Insulin-like growth factor-binding protein 7 | 33 | | − | − | − |
| Serum amyloid P-component; Metalloproteinase inhibitor 2 | 34 | | − | − | − |
| Immunoglobulin A; Metalloproteinase inhibitor 2 | 35 | | − | − | − |
| Neutrophil elastase; Serum amyloid P-component | 36 | | − | − | − |
| Insulin-like growth factor-binding protein 7; (Alpha-1 antitrypsin) | 37 | | − | − | − |
| Insulin-like growth factor-binding protein 7; Metalloproteinase inhibitor 2 | 38 | | − | − | − |
| Hyaluronic acid; Serum amyloid P-component | 39 | | − | − | − |
| Neutrophil elastase; Tumor necrosis factor receptor superfamily member 11B | 40 | | − | − | − |
| Neutrophil elastase; Insulin-like growth factor-binding protein 7 | 41 | | − | − | − |
| Hyaluronic acid; C-X-C motif chemokines (−1, −2, −3) | 42 | | − | − | − |
| Insulin-like growth factor-binding protein 7; Immunoglobulin G1 | 43 | | − | − | − |
| Insulin-like growth factor-binding protein 7; Hepatocyte growth factor | 44 | | − | − | − |
| Hepatocyte growth factor; (Alpha-1 antitrypsin) | 45 | | − | − | − |
| Insulin-like growth factor-binding protein 7; Interleukin-11 | 46 | | − | − | − |
| Beta-2-glycoprotein 1; Insulin-like growth factor-binding protein 7 | 47 | | − | − | − |
| Beta-2-glycoprotein 1; Metalloproteinase inhibitor 2 | 48 | | − | − | − |
| Hyaluronic acid; C-C motif chemokine 13 | 49 | | − | − | − |
| Insulin-like growth factor-binding protein 7; C-X-C motif chemokines (−1, −2, −3) | 50 | | − | − | − |
| Insulin-like growth factor-binding protein 7; C-C motif chemokine 13 | 51 | | − | − | − |

TABLE 5

Significance of exemplary two marker panels; product model, "−" if p < 0.05, and as "+" if p ≥ 0.05

| | Analysis | | Significant panels (P value less than or equal to 0.05) by analysis. Panel numbers are as listed in Table 1 |
|---|---|---|---|
| sCr | 0 hrs prior to AKI stage | A | 4, 11, 12, 14, 16, 18, 19, 21, 24, 34, 36, 37, 43, 45, 46, 50 |
| | | B | 1, 3, 4, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 6, 9, 10, 11, 12, 14, 16, 18, 19, 21, 23, 24, 27, 28, 30, 34, 35, 36, 37, 38, 39, 40, 42, 43, 45, 50 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | |
| | | B | 1, 3, 4, 7, 11, 12, 14, 18, 19, 21, 23, 24, 28, 32, 33, 34, 35, 37, 38, 39, 42, 43, 44, 45, 46, 50, 51 |
| | | C | 1, 7, 11, 12, 17, 18, 19, 21, 22, 28, 32, 33, 34, 37, 38, 39, 43, 44, 45, 46, 47, 48, 50, 51 |
| | | D | 1, 2, 3, 4, 5, 6, 7, 9, 11, 12, 14, 15, 17, 18, 19, 20, 21, 22, 23, 25, 26, 28, 30, 32, 33, 34, 35, 36, 37, 38, 39, 40, 41, 42, 43, 44, 45, 46, 47, 48, 49, 50, 51 |
| sCr_UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 3, 4, 5, 6, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | 6, 7, 11, 18, 22, 26, 32, 33, 44, 45 |
| | | B | 1, 3, 6, 7, 9, 11, 12, 14, 18, 19, 21, 22, 23, 24, 27, 28, 32, 33, 34, 35, 36, 37, 38, 39, 42, 43, 44, 45, 46, 47, 50, 51 |
| | | C | 19, 21, 28, 44 |
| | | D | 1, 2, 3, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 3, 4, 5, 6, 7, 8, 9, 10, 11, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 51 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | 6, 7, 9, 11, 17, 26, 27, 32, 33, 42, 44, 45, 49 |
| | | B | 1, 3, 5, 6, 7, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 28 |
| | | D | 1, 2, 3, 4, 6, 7, 9, 11, 12, 13, 14, 15, 17, 18, 19, 21, 22, 23, 24, 25, 26, 27, 28, 29, 30, 32, 33, 34, 35, 37, 38, 39, 40, 41, 42, 43, 44, 45, 46, 47, 48, 49, 50, 51 |

TABLE 6

Significance of exemplary two marker panels; logistic regression model; "−" if p < 0.05, and as "+" if p ≥ 0.05

| | Analysis | | Significant panels (P value less than or equal to 0.05) by analysis. Panel numbers are as listed in Table 2 |
|---|---|---|---|
| sCr | 0 hrs prior to AKI stage | A | 1, 4, 6, 9, 10, 11, 12, 14, 16, 18, 19, 21, 22, 24, 28, 31, 33, 34, 36, 37, 39, 42, 45, 46, 51 |
| | | B | 1, 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 3, 4, 5, 6, 9, 10, 11, 12, 13, 14, 16, 18, 19, 21, 22, 23, 24, 25, 27, 28, 30, 31, 32, 34, 35, 36, 37, 38, 39, 40, 42, 43, 45, 50, 51 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | 8, 9, 16, 46 |
| | | B | 1, 5, 9, 11, 16, 18, 19, 21, 24, 25, 31, 32, 33, 34, 36, 37, 39, 40, 41, 44, 45 |
| | | C | 1, 5, 7, 9, 18, 19, 20, 21, 25, 31, 32, 34, 36, 39, 40, 41, 44, 45, 51 |
| | | D | 1, 2, 3, 4, 5, 6, 7, 8, 9, 11, 12, 14, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| sCr_UO | 0 hrs prior to AKI stage | A | 1, 2, 3, 4, 5, 6, 7, 8, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 3, 4, 5, 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 51 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | 2, 4, 6, 7, 11, 17, 22, 26, 27, 29, 32, 33, 39, 42, 44, 45, 49 |
| | | B | 1, 2, 3, 4, 6, 7, 9, 11, 12, 14, 15, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51 |
| | | C | 2, 4, 9, 12, 13, 15, 19, 21, 28, 33, 37, 38, 39, 40, 41, 43, 44, 46, 47, 50, 51 |

TABLE 6-continued

Significance of exemplary two marker panels; logistic regression model; "−" if p < 0.05, and as "+" if p ≥ 0.05

| | | Analysis | Significant panels (P value less than or equal to 0.05) by analysis. Panel numbers are as listed in Table 2 |
|---|---|---|---|
| UO | 0 hrs prior to AKI stage | D | 1, 2, 3, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 50, 51 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | 48 hrs prior to AKI stage | A | 2, 6, 7, 11, 17, 22, 26, 27, 29, 32, 33, 39, 40, 42, 44, 45, 49 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 |
| | | C | 12, 13, 28, 35, 38, 46, 47 |
| | | D | 1, 2, 3, 4, 5, 7, 8, 9, 11, 12, 13, 14, 15, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51 |

TABLE 7

Significance of exemplary three marker panels, product model; "−" if p < 0.05, and as "+" if p ≥ 0.05

| | | 24 hrs prior to AKI stage | | | | | | | | | | | |
|---|---|---|---|---|---|---|---|---|---|---|---|---|
| | | sCr | | | | sCr_UO | | | | UO | | | |
| | Panel | Analysis | | | | | | | | | | | |
| | # | A | B | C | D | A | B | C | D | A | B | C | D |
| Neutrophil elastase × Hyaluronic acid × Interleukin-11 | 1 | − | − | − | − | − | − | − | − | − | − | − | − |
| Macrophage colony-stimulating factor 1 × Neutrophil elastase/(Alpha-1 antitrypsin) | 2 | − | − | − | + | − | − | − | − | − | − | − | − |
| Serum amyloid P-component × Neutrophil elastase × C-C motif chemokine 24 | 3 | − | − | − | − | − | − | − | − | − | − | − | − |
| Neutrophil elastase × Insulin-like growth factor-binding protein 7 × C-X-C motif chemokine 6 | 4 | − | − | − | − | − | − | − | − | − | − | − | − |
| Serum amyloid P-component × Neutrophil elastase × Hepatocyte growth factor | 5 | − | − | − | − | − | − | − | − | − | − | − | − |
| Hyaluronic acid × Neutrophil elastase × Immunoglobulin G2 | 6 | − | − | − | − | − | − | − | − | − | − | − | − |
| Beta-2-glycoprotein 1 × Insulin-like growth factor-binding protein 7 × Interleukin-11 | 7 | − | − | − | − | − | − | − | − | − | − | − | − |
| Cathepsin D × Neutrophil elastase × Hepatocyte growth factor | 8 | − | − | − | − | − | − | − | − | − | − | − | − |
| Immunoglobulin G1 × Hepatocyte growth factor/(Alpha-1 antitrypsin) | 9 | − | − | − | − | − | − | − | − | − | − | − | − |
| Insulin-like growth factor-binding protein 7 × Interleukin-1 beta/(Alpha-1 antitrypsin) | 10 | − | − | − | − | − | − | − | − | − | − | − | − |
| Serum amyloid P-component × Insulin-like growth factor-binding protein 7 × Interleukin-11 | 11 | − | − | − | − | − | − | − | − | − | − | − | − |
| Neutrophil elastase × Immunoglobulin A × Metalloproteinase inhibitor 2 | 12 | − | − | − | − | − | − | − | − | − | − | − | − |
| Insulin-like growth factor-binding protein 7 × Metalloproteinase inhibitor 2 × Hepatocyte growth factor | 13 | − | − | − | − | − | − | − | − | − | − | − | − |
| Neutrophil elastase × Cathepsin D/(Alpha-1 antitrypsin) | 14 | − | − | − | − | − | − | − | − | − | − | − | − |
| C-C motif chemokine 24 × Neutrophil elastase × Metalloproteinase inhibitor 2 | 15 | − | − | − | − | − | − | − | − | − | − | − | − |
| Neutrophil elastase × Insulin-like growth factor-binding protein 7 × Immunoglobulin G1 | 16 | − | − | − | − | − | − | − | − | − | − | − | − |
| Hyaluronic acid × Immunoglobulin A × Metalloproteinase inhibitor 2 | 17 | − | − | − | − | − | − | − | − | − | − | − | − |
| Neutrophil elastase × Hyaluronic acid × Immunoglobulin G1 | 18 | − | − | − | − | − | − | − | − | − | − | − | − |
| Hyaluronic acid × Insulin-like growth factor-binding protein 7 × Cathepsin D | 19 | − | − | − | − | − | − | − | − | − | − | − | − |
| Hyaluronic acid × Insulin-like growth factor-binding protein 7 × Hepatocyte growth factor | 20 | − | − | − | − | − | − | − | − | − | − | − | − |
| C-C motif chemokine 24 × Serum amyloid P-component/(Alpha-1 antitrypsin) | 21 | − | − | − | − | − | − | − | − | − | − | − | − |
| Insulin-like growth factor-binding protein 7 × Interleukin-11 × Metalloproteinase inhibitor 2 | 22 | − | − | − | − | − | − | − | − | − | − | − | − |

TABLE 7-continued

Significance of exemplary three marker panels, product model; "−" if p < 0.05, and as "+" if p ≥ 0.05

| Panel | Panel # | 24 hrs prior to AKI stage |||| |||| ||||
|---|---|---|---|---|---|---|---|---|---|---|---|---|---|
| | | sCr |||| sCr_UO Analysis |||| UO ||||
| | | A | B | C | D | A | B | C | D | A | B | C | D |
| Serum amyloid P-component × Insulin-like growth factor-binding protein 7 × Metalloproteinase inhibitor 2 | 23 | − | − | − | − | − | − | − | − | − | − | − | − |
| Hyaluronic acid × Neutrophil elastase × Immunoglobulin A | 24 | − | − | − | − | − | − | − | − | − | − | − | − |
| Hyaluronic acid × Insulin-like growth factor-binding protein 7 × Immunoglobulin G1 | 25 | − | − | − | − | − | − | − | − | − | − | − | − |
| Neutrophil elastase × Insulin-like growth factor-binding protein 7 × Interleukin-11 | 26 | − | − | − | − | − | − | − | − | − | − | − | − |
| Hyaluronic acid × Serum amyloid P-component × Metalloproteinase inhibitor 2 | 27 | − | − | − | − | − | − | − | − | − | − | − | − |
| Immunoglobulin G1 × Metalloproteinase inhibitor 2/(Alpha-1 antitrypsin) | 28 | − | − | − | − | − | − | − | − | − | − | − | − |
| Neutrophil elastase × Serum amyloid P-component × Metalloproteinase inhibitor 2 | 29 | − | − | − | − | − | − | − | − | − | − | − | − |
| Neutrophil elastase × Beta-2-glycoprotein 1 × Metalloproteinase inhibitor 2 | 30 | − | − | − | − | − | − | − | − | − | − | − | − |
| Interleukin-2 receptor alpha chain × Neutrophil elastase/(Alpha-1 antitrypsin) | 31 | − | − | − | + | − | − | − | − | − | − | − | − |
| Immunoglobulin G2 × Insulin-like growth factor-binding protein 7/(Alpha-1 antitrypsin) | 32 | − | − | − | − | − | − | − | − | − | − | − | − |
| Hyaluronic acid × Beta-2-glycoprotein 1 × Metalloproteinase inhibitor 2 | 33 | − | − | − | − | − | − | − | − | − | − | − | − |
| Interleukin-11 × Serum amyloid P-component/(Alpha-1 antitrypsin) | 34 | − | − | − | − | − | − | − | − | − | − | − | − |
| Insulin-like growth factor-binding protein 7 × Immunoglobulin A × Metalloproteinase inhibitor 2 | 35 | − | − | − | − | − | − | − | − | − | − | − | − |
| Beta-2-glycoprotein 1 × Insulin-like growth factor-binding protein 7 × Hepatocyte growth factor | 36 | − | − | − | − | − | − | − | − | − | − | − | − |
| Hyaluronic acid × Neutrophil elastase × Beta-2-glycoprotein 1 | 37 | + | − | − | − | − | − | − | − | − | − | − | − |
| Matrilysin × Neutrophil elastase/(Alpha-1 antitrypsin) | 38 | − | − | − | − | − | − | − | − | − | − | − | − |
| Hyaluronic acid × Neutrophil elastase × C-C motif chemokine 24 | 39 | − | − | − | − | − | − | − | − | − | − | − | − |
| Metalloproteinase inhibitor 2 × Neutrophil elastase × Tumor necrosis factor receptor superfamily member 11B | 40 | − | − | − | − | − | − | − | − | − | − | − | − |
| Neutrophil elastase × Hepatocyte growth factor/(Alpha-1 antitrypsin) | 41 | − | − | − | − | − | − | − | − | − | − | − | − |
| Insulin-like growth factor-binding protein 3 × Neutrophil elastase/(Alpha-1 antitrypsin) | 42 | − | − | − | − | − | − | − | − | − | − | − | − |
| Neutrophil elastase × Insulin-like growth factor-binding protein 7 × Immunoglobulin A | 43 | − | − | − | − | − | − | − | − | − | − | − | − |
| Hyaluronic acid × Insulin-like growth factor-binding protein 7 × C-C motif chemokine 13 | 44 | − | − | − | − | − | − | − | − | − | − | − | − |
| Hyaluronic acid × Serum amyloid P-component × Insulin-like growth factor-binding protein 7 | 45 | − | − | − | − | − | − | − | − | − | − | − | − |
| Hyaluronic acid × Neutrophil elastase × Tumor necrosis factor receptor superfamily member 11B | 46 | − | − | − | − | − | − | − | − | − | − | − | − |
| Insulin-like growth factor-binding protein 7 × Immunoglobulin A/(Alpha-1 antitrypsin) | 47 | − | − | − | − | − | − | − | − | − | − | − | − |
| Hyaluronic acid × Insulin-like growth factor-binding protein 7 × Interleukin-11 | 48 | − | − | − | − | − | − | − | − | − | − | − | − |
| Insulin-like growth factor-binding protein 7 × Neutrophil elastase × Tumor necrosis factor receptor superfamily member 11B | 49 | − | − | − | − | − | − | − | − | − | − | − | − |
| Neutrophil elastase × Serum amyloid P-component × Insulin-like growth factor-binding protein 7 | 50 | − | − | − | − | − | − | − | − | − | − | − | − |
| Hyaluronic acid × Hepatocyte growth factor/(Alpha-1 antitrypsin) | 51 | − | − | − | − | − | − | − | − | − | − | − | − |
| Neutrophil elastase × Immunoglobulin A/(Alpha-1 antitrypsin) | 52 | − | − | − | − | − | − | − | − | − | − | − | − |
| Beta-2-glycoprotein 1 × Neutrophil elastase/(Alpha-1 antitrypsin) | 53 | − | − | − | − | − | − | − | − | − | − | − | − |
| Hyaluronic acid × Insulin-like growth factor-binding protein 7/(Alpha-1 antitrypsin) | 54 | − | − | − | − | − | − | − | − | − | − | − | − |
| Hyaluronic acid × Immunoglobulin A/(Alpha-1 antitrypsin) | 55 | − | − | − | − | − | − | − | − | − | − | − | − |
| Hyaluronic acid × Serum amyloid P-component/(Alpha-1 antitrypsin) | 56 | − | − | − | − | − | − | − | − | − | − | − | − |
| Neutrophil elastase × C-C motif chemokine 24/(Alpha-1 antitrypsin) | 57 | − | − | − | − | − | − | − | − | − | − | − | − |
| Hyaluronic acid × Neutrophil elastase/(Alpha-1 antitrypsin) | 58 | − | − | − | − | − | − | − | − | − | − | − | − |
| Hyaluronic acid × Neutrophil elastase × Insulin-like growth factor-binding protein 7 | 59 | − | − | − | − | − | − | − | − | − | − | − | − |

TABLE 7-continued

Significance of exemplary three marker panels, product model; "−" if p < 0.05, and as "+" if p ≥ 0.05

| | | 24 hrs prior to AKI stage ||||||||||||
|---|---|---|---|---|---|---|---|---|---|---|---|---|
| | | sCr |||| sCr_UO Analysis |||| UO ||||
| Panel | # | A | B | C | D | A | B | C | D | A | B | C | D |
| Neutrophil elastase × Cathepsin D × Metalloproteinase inhibitor 2 | 60 | − | − | − | − | − | − | − | − | − | − | − | − |
| Beta-2-glycoprotein 1 × Metalloproteinase inhibitor 2/(Alpha-1 antitrypsin) | 61 | − | − | − | − | − | − | − | − | − | − | − | − |
| Hyaluronic acid × Neutrophil elastase × Serum amyloid P-component | 62 | − | − | − | − | − | − | − | − | − | − | − | − |
| Neutrophil elastase × Insulin-like growth factor-binding protein 7 × C-C motif chemokine 24 | 63 | − | − | − | − | − | − | − | − | − | − | − | − |
| Insulin-like growth factor-binding protein 7 × Metalloproteinase inhibitor 2/(Alpha-1 antitrypsin) | 64 | − | − | − | − | − | − | − | − | − | − | − | − |
| Hyaluronic acid × Neutrophil elastase × Metalloproteinase inhibitor 2 | 65 | − | − | − | − | − | − | − | − | − | − | − | − |
| Immunoglobulin A × Hepatocyte growth factor/(Alpha-1 antitrypsin) | 66 | − | − | − | − | − | − | − | − | − | − | − | − |
| Serum amyloid P-component × Hepatocyte growth factor/(Alpha-1 antitrypsin) | 67 | − | − | − | − | − | − | − | − | − | − | − | − |
| Neutrophil elastase × Insulin-like growth factor-binding protein 7/(Alpha-1 antitrypsin) | 68 | − | − | − | − | − | − | − | − | − | − | − | − |
| Hyaluronic acid × Neutrophil elastase × Cathepsin D | 69 | − | − | − | − | − | − | − | − | − | − | − | − |
| Insulin-like growth factor-binding protein 7 × Immunoglobulin G1/(Alpha-1 antitrypsin) | 70 | − | − | − | − | − | − | − | − | − | − | − | − |
| Hyaluronic acid × Insulin-like growth factor-binding protein 7 × Metalloproteinase inhibitor 2 | 71 | − | − | − | − | − | − | − | − | − | − | − | − |
| Immunoglobulin A × Metalloproteinase inhibitor 2/(Alpha-1 antitrypsin) | 72 | − | − | − | − | − | − | − | − | − | − | − | − |
| Hyaluronic acid × Beta-2-glycoprotein 1 × Insulin-like growth factor-binding protein 7 | 73 | − | − | − | − | − | − | − | − | − | − | − | − |
| Neutrophil elastase × Metalloproteinase inhibitor 2 × Hepatocyte growth factor | 74 | − | − | − | − | − | − | − | − | − | − | − | − |
| Hyaluronic acid × Neutrophil elastase × Hepatocyte growth factor | 75 | − | − | − | − | − | − | − | − | − | − | − | − |
| Neutrophil elastase × Insulin-like growth factor-binding protein 7 × Cathepsin D | 76 | − | − | − | − | − | − | − | − | − | − | − | − |
| Neutrophil elastase × Tumor necrosis factor receptor superfamily member 11B/(Alpha-1 antitrypsin) | 77 | − | − | − | − | − | − | − | − | − | − | − | − |
| Beta-2-glycoprotein 1 × Insulin-like growth factor-binding protein 7/(Alpha-1 antitrypsin) | 78 | − | − | − | − | − | − | − | − | − | − | − | − |
| Neutrophil elastase × Metalloproteinase inhibitor 2/(Alpha-1 antitrypsin) | 79 | − | − | − | − | − | − | − | − | − | − | − | − |
| Insulin-like growth factor-binding protein 7 × Hepatocyte growth factor/(Alpha-1 antitrypsin) | 80 | − | − | − | − | − | − | − | − | − | − | − | − |
| Beta-2-glycoprotein 1 × Hyaluronic acid/(Alpha-1 antitrypsin) | 81 | − | − | − | − | − | − | − | − | − | − | − | − |
| Neutrophil elastase × Insulin-like growth factor-binding protein 7 × Hepatocyte growth factor | 82 | − | − | − | − | − | − | − | − | − | − | − | − |
| Serum amyloid P-component × Insulin-like growth factor-binding protein 7/(Alpha-1 antitrypsin) | 83 | − | − | − | − | − | − | − | − | − | − | − | − |
| Neutrophil elastase × Beta-2-glycoprotein 1 × Insulin-like growth factor-binding protein 7 | 84 | − | − | − | − | − | − | − | − | − | − | − | − |
| Neutrophil elastase × Insulin-like growth factor-binding protein 7 × Metalloproteinase inhibitor 2 | 85 | − | − | − | − | − | − | − | − | − | − | − | − |
| Beta-2-glycoprotein 1 × Insulin-like growth factor-binding protein 7 × Metalloproteinase inhibitor 2 | 86 | − | − | − | − | − | − | − | − | − | − | − | − |
| Beta-2-glycoprotein 1 × Hepatocyte growth factor/(Alpha-1 antitrypsin) | 87 | − | − | − | − | − | − | − | − | − | − | − | − |
| Hyaluronic acid × Insulin-like growth factor-binding protein 7 × Immunoglobulin A | 88 | − | − | − | − | − | − | − | − | − | − | − | − |
| Serum amyloid P-component × Metalloproteinase inhibitor 2/(Alpha-1 antitrypsin) | 89 | − | − | − | − | − | − | − | − | − | − | − | − |
| Metalloproteinase inhibitor 2 × Hepatocyte growth factor/(Alpha-1 antitrypsin) | 90 | − | − | − | − | − | − | − | − | − | − | − | − |
| Hyaluronic acid × Immunoglobulin G1/(Alpha-1 antitrypsin) | 91 | − | − | − | − | − | − | − | − | − | − | − | − |
| Hyaluronic acid × Metalloproteinase inhibitor 2/(Alpha-1 antitrypsin) | 92 | − | − | − | − | − | − | − | − | − | − | − | − |
| Neutrophil elastase × Serum amyloid P-component/(Alpha-1 antitrypsin) | 93 | − | − | − | − | − | − | − | − | − | − | − | − |
| Beta-2-glycoprotein 1 × Metalloproteinase inhibitor 2/(Intercellular adhesion molecule 1) | 94 | − | − | − | − | − | − | − | − | − | − | − | − |

TABLE 8

Significance of exemplary three marker panels, logistic regression model; "−" if p < 0.05, and as "+" if p ≥ 0.05

| | | 24 hrs prior to AKI stage | | | | | | | | | | | |
|---|---|---|---|---|---|---|---|---|---|---|---|---|---|
| | | sCr | | | | sCr_UO Analysis | | | | UO | | | |
| Panel | # | A | B | C | D | A | B | C | D | A | B | C | D |
| Neutrophil elastase; Hyaluronic acid; Interleukin-11 | 1 | − | − | − | − | − | − | − | − | − | − | − | − |
| Macrophage colony-stimulating factor 1; Neutrophil elastase; (Alpha-1 antitrypsin) | 2 | − | − | − | − | − | − | − | − | − | − | − | − |
| Serum amyloid P-component; Neutrophil elastase; C-C motif chemokine 24 | 3 | − | − | − | − | − | − | − | − | − | − | − | − |
| Neutrophil elastase; Insulin-like growth factor-binding protein 7; C-X-C motif chemokine 6 | 4 | − | − | − | − | − | − | − | − | − | − | − | − |
| Serum amyloid P-component; Neutrophil elastase; Hepatocyte growth factor | 5 | − | − | − | − | − | − | − | − | − | − | − | − |
| Hyaluronic acid; Neutrophil elastase; Immunoglobulin G2 | 6 | − | − | − | − | − | − | − | − | − | − | − | − |
| Beta-2-glycoprotein 1; Insulin-like growth factor-binding protein 7; Interleukin-11 | 7 | − | − | − | − | − | − | − | − | − | − | − | − |
| Cathepsin D; Neutrophil elastase; Hepatocyte growth factor | 8 | − | − | − | − | − | − | − | − | − | − | − | − |
| Immunoglobulin G1; Hepatocyte growth factor; (Alpha-1 antitrypsin) | 9 | − | − | − | − | − | − | − | − | − | − | − | − |
| Insulin-like growth factor-binding protein 7; Interleukin-1 beta; (Alpha-1 antitrypsin) | 10 | − | − | − | − | − | − | − | − | − | − | − | − |
| Serum amyloid P-component; Insulin-like growth factor-binding protein 7; Interleukin-11 | 11 | − | − | − | − | − | − | − | − | − | − | − | − |
| Neutrophil elastase; Immunoglobulin A; Metalloproteinase inhibitor 2 | 12 | − | − | − | − | − | − | − | − | − | − | − | − |
| Insulin-like growth factor-binding protein 7; Metalloproteinase inhibitor 2; Hepatocyte growth factor | 13 | − | − | − | + | − | − | − | − | − | − | − | − |
| Neutrophil elastase; Cathepsin D; (Alpha-1 antitrypsin) | 14 | − | − | − | − | − | − | − | − | − | − | − | − |
| C-C motif chemokine 24; Neutrophil elastase; Metalloproteinase inhibitor 2 | 15 | − | − | − | − | − | − | − | − | − | − | − | − |
| Neutrophil elastase; Insulin-like growth factor-binding protein 7; Immunoglobulin G1 | 16 | − | − | − | − | − | − | − | − | − | − | − | − |
| Hyaluronic acid; Immunoglobulin A; Metalloproteinase inhibitor 2 | 17 | − | − | − | − | − | − | − | − | − | − | − | − |
| Neutrophil elastase; Hyaluronic acid; Immunoglobulin G1 | 18 | − | − | − | − | − | − | − | − | − | − | − | − |
| Hyaluronic acid; Insulin-like growth factor-binding protein 7; Cathepsin D | 19 | − | − | − | − | − | − | − | − | − | − | − | − |
| Hyaluronic acid; Insulin-like growth factor-binding protein 7; Hepatocyte growth factor | 20 | − | − | − | − | − | − | − | − | − | − | − | − |
| C-C motif chemokine 24; Serum amyloid P-component; (Alpha-1 antitrypsin) | 21 | − | − | − | − | − | − | − | − | − | − | − | − |
| Insulin-like growth factor-binding protein 7; Interleukin-11; Metalloproteinase inhibitor 2 | 22 | − | − | − | − | − | − | − | − | − | − | − | − |
| Serum amyloid P-component; Insulin-like growth factor-binding protein 7; Metalloproteinase inhibitor 2 | 23 | − | − | − | − | − | − | − | − | − | − | − | − |
| Hyaluronic acid; Neutrophil elastase; Immunoglobulin A | 24 | − | − | − | − | − | − | − | − | − | − | − | − |
| Hyaluronic acid; Insulin-like growth factor-binding protein 7; Immunoglobulin G1 | 25 | − | − | − | − | − | − | − | − | − | − | − | − |
| Neutrophil elastase; Insulin-like growth factor-binding protein 7; Interleukin-11 | 26 | − | − | − | − | − | − | − | − | − | − | − | − |
| Hyaluronic acid; Serum amyloid P-component; Metalloproteinase inhibitor 2 | 27 | − | − | − | − | − | − | − | − | − | − | − | − |
| Immunoglobulin G1; Metalloproteinase inhibitor 2; (Alpha-1 antitrypsin) | 28 | − | − | − | − | − | − | − | − | − | − | − | − |
| Neutrophil elastase; Serum amyloid P-component; Metalloproteinase inhibitor 2 | 29 | − | − | − | − | − | − | − | − | − | − | − | − |
| Neutrophil elastase; Beta-2-glycoprotein 1; Metalloproteinase inhibitor 2 | 30 | − | − | − | − | − | − | − | − | − | − | − | − |
| Interleukin-2 receptor alpha chain; Neutrophil elastase; (Alpha-1 antitrypsin) | 31 | − | − | − | − | − | − | − | − | − | − | − | − |
| Immunoglobulin G2; Insulin-like growth factor-binding protein 7; (Alpha-1 antitrypsin) | 32 | − | − | − | − | − | − | − | − | − | − | − | − |
| Hyaluronic acid; Beta-2-glycoprotein 1; Metalloproteinase inhibitor 2 | 33 | − | − | − | − | − | − | − | − | − | − | − | − |
| Interleukin-11; Serum amyloid P-component; (Alpha-1 antitrypsin) | 34 | − | − | − | − | − | − | − | − | − | − | − | − |
| Insulin-like growth factor-binding protein 7; Immunoglobulin A; Metalloproteinase inhibitor 2 | 35 | − | − | − | − | − | − | − | − | − | − | − | − |
| Beta-2-glycoprotein 1; Insulin-like growth factor-binding protein 7; Hepatocyte growth factor | 36 | − | − | − | − | − | − | − | − | − | − | − | − |
| Hyaluronic acid; Neutrophil elastase; Beta-2-glycoprotein 1 | 37 | − | − | − | − | − | − | − | − | − | − | − | − |
| Matrilysin; Neutrophil elastase; (Alpha-1 antitrypsin) | 38 | − | − | − | − | − | − | − | − | − | − | − | − |
| Hyaluronic acid; Neutrophil elastase; C-C motif chemokine 24 | 39 | − | − | − | − | − | − | − | − | − | − | − | − |
| Metalloproteinase inhibitor 2; Neutrophil elastase; Tumor necrosis factor receptor superfamily member 11B | 40 | − | − | − | − | − | − | − | − | − | − | − | − |

TABLE 8-continued

Significance of exemplary three marker panels, logistic regression model; "−" if p < 0.05, and as "+" if p ≥ 0.05

| Panel | # | 24 hrs prior to AKI stage ||||||||||||
|---|---|---|---|---|---|---|---|---|---|---|---|---|---|
| | | sCr |||| sCr_UO Analysis |||| UO ||||
| | | A | B | C | D | A | B | C | D | A | B | C | D |
| Neutrophil elastase; Hepatocyte growth factor; (Alpha-1 antitrypsin) | 41 | − | − | − | − | − | − | − | − | − | − | − | − |
| Insulin-like growth factor-binding protein 3; Neutrophil elastase; (Alpha-1 antitrypsin) | 42 | − | − | − | − | − | − | − | − | − | − | − | − |
| Neutrophil elastase; Insulin-like growth factor-binding protein 7; Immunoglobulin A | 43 | − | − | − | − | − | − | − | − | − | − | − | − |
| Hyaluronic acid; Insulin-like growth factor-binding protein 7; C-C motif chemokine 13 | 44 | − | − | − | − | − | − | − | − | − | − | − | − |
| Hyaluronic acid; Serum amyloid P-component; Insulin-like growth factor-binding protein 7 | 45 | − | − | − | − | − | − | − | − | − | − | − | − |
| Hyaluronic acid; Neutrophil elastase; Tumor necrosis factor receptor superfamily member 11B | 46 | − | − | − | − | − | − | − | − | − | − | − | − |
| Insulin-like growth factor-binding protein 7; Immunoglobulin A; (Alpha-1 antitrypsin) | 47 | − | − | − | − | − | − | − | − | − | − | − | − |
| Hyaluronic acid; Insulin-like growth factor-binding protein 7; Interleukin-11 | 48 | − | − | − | − | − | − | − | − | − | − | − | − |
| Insulin-like growth factor-binding protein 7; Neutrophil elastase; Tumor necrosis factor receptor superfamily member 11B | 49 | − | − | − | − | − | − | − | − | − | − | − | − |
| Neutrophil elastase; Serum amyloid P-component; Insulin-like growth factor-binding protein 7 | 50 | − | − | − | − | − | − | − | − | − | − | − | − |
| Hyaluronic acid; Hepatocyte growth factor; (Alpha-1 antitrypsin) | 51 | − | − | − | − | − | − | − | − | − | − | − | − |
| Neutrophil elastase; Immunoglobulin A; (Alpha-1 antitrypsin) | 52 | − | − | − | − | − | − | − | − | − | − | − | − |
| Beta-2-glycoprotein 1; Neutrophil elastase; (Alpha-1 antitrypsin) | 53 | − | − | − | − | − | − | − | − | − | − | − | − |
| Hyaluronic acid; Insulin-like growth factor-binding protein 7; (Alpha-1 antitrypsin) | 54 | − | − | − | − | − | − | − | − | − | − | − | − |
| Hyaluronic acid; Immunoglobulin A; (Alpha-1 antitrypsin) | 55 | − | − | − | − | − | − | − | − | − | − | − | − |
| Hyaluronic acid; Serum amyloid P-component; (Alpha-1 antitrypsin) | 56 | − | − | − | − | − | − | − | − | − | − | − | − |
| Neutrophil elastase; C-C motif chemokine 24; (Alpha-1 antitrypsin) | 57 | − | − | − | − | − | − | − | − | − | − | − | − |
| Hyaluronic acid; Neutrophil elastase; (Alpha-1 antitrypsin) | 58 | − | − | − | − | − | − | − | − | − | − | − | − |
| Hyaluronic acid; Neutrophil elastase; Insulin-like growth factor-binding protein 7 | 59 | − | − | − | − | − | − | − | − | − | − | − | − |
| Neutrophil elastase; Cathepsin D; Metalloproteinase inhibitor 2 | 60 | − | − | − | − | − | − | − | − | − | − | − | − |
| Beta-2-glycoprotein 1; Metalloproteinase inhibitor 2; (Alpha-1 antitrypsin) | 61 | − | − | − | − | − | − | − | − | − | − | − | − |
| Hyaluronic acid; Neutrophil elastase; Serum amyloid P-component | 62 | − | − | − | − | − | − | − | − | − | − | − | − |
| Neutrophil elastase; Insulin-like growth factor-binding protein 7; C-C motif chemokine 24 | 63 | − | − | − | − | − | − | − | − | − | − | − | − |
| Insulin-like growth factor-binding protein 7; Metalloproteinase inhibitor 2; (Alpha-1 antitrypsin) | 64 | − | − | − | − | − | − | − | − | − | − | − | − |
| Hyaluronic acid; Neutrophil elastase; Metalloproteinase inhibitor 2 | 65 | − | − | − | − | − | − | − | − | − | − | − | − |
| Immunoglobulin A; Hepatocyte growth factor; (Alpha-1 antitrypsin) | 66 | − | − | − | − | − | − | − | − | − | − | − | − |
| Serum amyloid P-component; Hepatocyte growth factor; (Alpha-1 antitrypsin) | 67 | − | − | − | − | − | − | − | − | − | − | − | − |
| Neutrophil elastase; Insulin-like growth factor-binding protein 7; (Alpha-1 antitrypsin) | 68 | − | − | − | − | − | − | − | − | − | − | − | − |
| Hyaluronic acid; Neutrophil elastase; Cathepsin D | 69 | − | − | − | − | − | − | − | − | − | − | − | − |
| Insulin-like growth factor-binding protein 7; Immunoglobulin G1; (Alpha-1 antitrypsin) | 70 | − | − | − | − | − | − | − | − | − | − | − | − |
| Hyaluronic acid; Insulin-like growth factor-binding protein 7; Metalloproteinase inhibitor 2 | 71 | − | − | − | − | − | − | − | − | − | − | − | − |
| Immunoglobulin A; Metalloproteinase inhibitor 2; (Alpha-1 antitrypsin) | 72 | − | − | − | − | − | − | − | − | − | − | − | − |
| Hyaluronic acid; Beta-2-glycoprotein 1; Insulin-like growth factor-binding protein 7 | 73 | − | − | − | − | − | − | − | − | − | − | − | − |
| Neutrophil elastase; Metalloproteinase inhibitor 2; Hepatocyte growth factor | 74 | − | − | − | − | − | − | − | − | − | − | − | − |
| Hyaluronic acid; Neutrophil elastase; Hepatocyte growth factor | 75 | − | − | − | − | − | − | − | − | − | − | − | − |
| Neutrophil elastase; Insulin-like growth factor-binding protein 7; Cathepsin D | 76 | − | − | − | − | − | − | − | − | − | − | − | − |
| Neutrophil elastase; Tumor necrosis factor receptor superfamily member 11B; (Alpha-1 antitrypsin) | 77 | − | − | − | − | − | − | − | − | − | − | − | − |

TABLE 8-continued

Significance of exemplary three marker panels, logistic regression model; "−" if p < 0.05, and as "+" if p ≥ 0.05

| | | 24 hrs prior to AKI stage | | | | | | | | | | | |
|---|---|---|---|---|---|---|---|---|---|---|---|---|---|
| | | sCr | | | | sCr_UO | | | | UO | | | |
| | Panel | | | | | Analysis | | | | | | | |
| | # | A | B | C | D | A | B | C | D | A | B | C | D |
| Beta-2-glycoprotein 1; Insulin-like growth factor-binding protein 7; (Alpha-1 antitrypsin) | 78 | − | − | − | − | − | − | − | − | − | − | − | − |
| Neutrophil elastase; Metalloproteinase inhibitor 2; (Alpha-1 antitrypsin) | 79 | − | − | − | − | − | − | − | − | − | − | − | − |
| Insulin-like growth factor-binding protein 7; Hepatocyte growth factor; (Alpha-1 antitrypsin) | 80 | − | − | − | − | − | − | − | − | − | − | − | − |
| Beta-2-glycoprotein 1; Hyaluronic acid; (Alpha-1 antitrypsin) | 81 | − | − | − | − | − | − | − | − | − | − | − | − |
| Neutrophil elastase; Insulin-like growth factor-binding protein 7; Hepatocyte growth factor | 82 | − | − | − | − | − | − | − | − | − | − | − | − |
| Serum amyloid P-component; Insulin-like growth factor-binding protein 7; (Alpha-1 antitrypsin) | 83 | − | − | − | − | − | − | − | − | − | − | − | − |
| Neutrophil elastase; Beta-2-glycoprotein 1; Insulin-like growth factor-binding protein 7 | 84 | − | − | − | − | − | − | − | − | − | − | − | − |
| Neutrophil elastase; Insulin-like growth factor-binding protein 7; Metalloproteinase inhibitor 2 | 85 | − | − | − | − | − | − | − | − | − | − | − | − |
| Beta-2-glycoprotein 1; Insulin-like growth factor-binding protein 7; Metalloproteinase inhibitor 2 | 86 | − | − | − | − | − | − | − | − | − | − | − | − |
| Beta-2-glycoprotein 1; Hepatocyte growth factor; (Alpha-1 antitrypsin) | 87 | − | − | − | − | − | − | − | − | − | − | − | − |
| Hyaluronic acid; Insulin-like growth factor-binding protein 7; Immunoglobulin A | 88 | − | − | − | − | − | − | − | − | − | − | − | − |
| Serum amyloid P-component; Metalloproteinase inhibitor 2; (Alpha-1 antitrypsin) | 89 | − | − | − | − | − | − | − | − | − | − | − | − |
| Metalloproteinase inhibitor 2; Hepatocyte growth factor; (Alpha-1 antitrypsin) | 90 | − | − | − | − | − | − | − | − | − | − | − | − |
| Hyaluronic acid; Immunoglobulin G1; (Alpha-1 antitrypsin) | 91 | − | − | − | − | − | − | − | − | − | − | − | − |
| Hyaluronic acid; Metalloproteinase inhibitor 2; (Alpha-1 antitrypsin) | 92 | − | − | − | − | − | − | − | − | − | − | − | − |
| Neutrophil elastase; Serum amyloid P-component; (Alpha-1 antitrypsin) | 93 | − | − | − | − | − | − | − | − | − | − | − | − |
| Beta-2-glycoprotein 1; Metalloproteinase inhibitor 2; (Intercellular adhesion molecule 1) | 94 | − | − | − | − | − | − | − | − | − | − | − | − |

TABLE 9

Significance of exemplary three marker panels, analysis E, product model; "−" if p < 0.05, and as "+" if p ≥ 0.05

| | Panel # | Analysis | sCr E | sCr_UO E | UO E |
|---|---|---|---|---|---|
| Neutrophil elastase × Hyaluronic acid × Interleukin-11 | 1 | | − | − | − |
| Macrophage colony-stimulating factor 1 × Neutrophil elastase/(Alpha-1 antitrypsin) | 2 | | − | − | − |
| Serum amyloid P-component × Neutrophil elastase × C-C motif chemokine 24 | 3 | | − | − | − |
| Neutrophil elastase × Insulin-like growth factor-binding protein 7 × C-X-C motif chemokine 6 | 4 | | − | − | − |
| Serum amyloid P-component × Neutrophil elastase × Hepatocyte growth factor | 5 | | − | − | − |
| Hyaluronic acid × Neutrophil elastase × Immunoglobulin G2 | 6 | | − | − | − |
| Beta-2-glycoprotein 1 × Insulin-like growth factor-binding protein 7 × Interleukin-11 | 7 | | − | − | − |
| Cathepsin D × Neutrophil elastase × Hepatocyte growth factor | 8 | | − | − | − |
| Immunoglobulin G1 × Hepatocyte growth factor/(Alpha-1 antitrypsin) | 9 | | − | − | − |
| Insulin-like growth factor-binding protein 7 × Interleukin-1 beta/(Alpha-1 antitrypsin) | 10 | | − | − | − |
| Serum amyloid P-component × Insulin-like growth factor-binding protein 7 × Interleukin-11 | 11 | | − | − | − |
| Neutrophil elastase × Immunoglobulin A × Metalloproteinase inhibitor 2 | 12 | | − | − | − |
| Insulin-like growth factor-binding protein 7 × Metalloproteinase inhibitor 2 × Hepatocyte growth factor | 13 | | − | − | − |
| Neutrophil elastase × Cathepsin D/(Alpha-1 antitrypsin) | 14 | | − | − | − |
| C-C motif chemokine 24 × Neutrophil elastase × Metalloproteinase inhibitor 2 | 15 | | − | − | − |
| Neutrophil elastase × Insulin-like growth factor-binding protein 7 × Immunoglobulin G1 | 16 | | − | − | − |
| Hyaluronic acid × Immunoglobulin A × Metalloproteinase inhibitor 2 | 17 | | − | − | − |
| Neutrophil elastase × Hyaluronic acid × Immunoglobulin G1 | 18 | | − | − | − |
| Hyaluronic acid × Insulin-like growth factor-binding protein 7 × Cathepsin D | 19 | | − | − | − |
| Hyaluronic acid × Insulin-like growth factor-binding protein 7 × Hepatocyte growth factor | 20 | | − | − | − |

TABLE 9-continued

Significance of exemplary three marker panels, analysis E, product model; "−" if p < 0.05, and as "+" if p ≥ 0.05

| | Panel # | Analysis | sCr E | sCr_UO E | UO E |
|---|---|---|---|---|---|
| C-C motif chemokine 24 × Serum amyloid P-component/(Alpha-1 antitrypsin) | 21 | | − | − | − |
| Insulin-like growth factor-binding protein 7 × Interleukin-11 × Metalloproteinase inhibitor 2 | 22 | | − | − | − |
| Serum amyloid P-component × Insulin-like growth factor-binding protein 7 × Metalloproteinase inhibitor 2 | 23 | | − | − | − |
| Hyaluronic acid × Neutrophil elastase × Immunoglobulin A | 24 | | − | − | − |
| Hyaluronic acid × Insulin-like growth factor-binding protein 7 × Immunoglobulin G1 | 25 | | − | − | − |
| Neutrophil elastase × Insulin-like growth factor-binding protein 7 × Interleukin-11 | 26 | | − | − | − |
| Hyaluronic acid × Serum amyloid P-component × Metalloproteinase inhibitor 2 | 27 | | − | − | − |
| Immunoglobulin G1 × Metalloproteinase inhibitor 2/(Alpha-1 antitrypsin) | 28 | | − | − | − |
| Neutrophil elastase × Serum amyloid P-component × Metalloproteinase inhibitor 2 | 29 | | − | − | − |
| Neutrophil elastase × Beta-2-glycoprotein 1 × Metalloproteinase inhibitor 2 | 30 | | − | − | − |
| Interleukin-2 receptor alpha chain × Neutrophil elastase/(Alpha-1 antitrypsin) | 31 | | − | − | − |
| Immunoglobulin G2 × Insulin-like growth factor-binding protein 7/(Alpha-1 antitrypsin) | 32 | | − | − | − |
| Hyaluronic acid × Beta-2-glycoprotein 1 × Metalloproteinase inhibitor 2 | 33 | | − | − | − |
| Interleukin-11 × Serum amyloid P-component/(Alpha-1 antitrypsin) | 34 | | − | − | − |
| Insulin-like growth factor-binding protein 7 × Immunoglobulin A × Metalloproteinase inhibitor 2 | 35 | | − | − | − |
| Beta-2-glycoprotein 1 × Insulin-like growth factor-binding protein 7 × Hepatocyte growth factor | 36 | | − | − | − |
| Hyaluronic acid × Neutrophil elastase × Beta-2-glycoprotein 1 | 37 | | − | − | − |
| Matrilysin × Neutrophil elastase/(Alpha-1 antitrypsin) | 38 | | − | − | − |
| Hyaluronic acid × Neutrophil elastase × C-C motif chemokine 24 | 39 | | − | − | − |
| Metalloproteinase inhibitor 2 × Neutrophil elastase × Tumor necrosis factor receptor superfamily member 11B | 40 | | − | − | − |
| Neutrophil elastase × Hepatocyte growth factor/(Alpha-1 antitrypsin) | 41 | | − | − | − |
| Insulin-like growth factor-binding protein 3 × Neutrophil elastase/(Alpha-1 antitrypsin) | 42 | | − | − | − |
| Neutrophil elastase × Insulin-like growth factor-binding protein 7 × Immunoglobulin A | 43 | | − | − | − |
| Hyaluronic acid × Insulin-like growth factor-binding protein 7 × C-C motif chemokine 13 | 44 | | − | − | − |
| Hyaluronic acid × Serum amyloid P-component × Insulin-like growth factor-binding protein 7 | 45 | | − | − | − |
| Hyaluronic acid × Neutrophil elastase × Tumor necrosis factor receptor superfamily member 11B | 46 | | − | − | − |
| Insulin-like growth factor-binding protein 7 × Immunoglobulin A/(Alpha-1 antitrypsin) | 47 | | − | − | − |
| Hyaluronic acid × Insulin-like growth factor-binding protein 7 × Interleukin-11 | 48 | | − | − | − |
| Insulin-like growth factor-binding protein 7 × Neutrophil elastase × Tumor necrosis factor receptor superfamily member 11B | 49 | | − | − | − |
| Neutrophil elastase × Serum amyloid P-component × Insulin-like growth factor-binding protein 7 | 50 | | − | − | − |
| Hyaluronic acid × Hepatocyte growth factor/(Alpha-1 antitrypsin) | 51 | | − | − | − |
| Neutrophil elastase × Immunoglobulin A/(Alpha-1 antitrypsin) | 52 | | − | − | − |
| Beta-2-glycoprotein 1 × Neutrophil elastase/(Alpha-1 antitrypsin) | 53 | | − | − | − |
| Hyaluronic acid × Insulin-like growth factor-binding protein 7/(Alpha-1 antitrypsin) | 54 | | − | − | − |
| Hyaluronic acid × Immunoglobulin A/(Alpha-1 antitrypsin) | 55 | | − | − | − |
| Hyaluronic acid × Serum amyloid P-component/(Alpha-1 antitrypsin) | 56 | | − | − | − |
| Neutrophil elastase × C-C motif chemokine 24/(Alpha-1 antitrypsin) | 57 | | − | − | − |
| Hyaluronic acid × Neutrophil elastase/(Alpha-1 antitrypsin) | 58 | | − | − | − |
| Hyaluronic acid × Neutrophil elastase × Insulin-like growth factor-binding protein 7 | 59 | | − | − | − |
| Neutrophil elastase × Cathepsin D × Metalloproteinase inhibitor 2 | 60 | | − | − | − |
| Beta-2-glycoprotein 1 × Metalloproteinase inhibitor 2/(Alpha-1 antitrypsin) | 61 | | − | − | − |
| Hyaluronic acid × Neutrophil elastase × Serum amyloid P-component | 62 | | − | − | − |
| Neutrophil elastase × Insulin-like growth factor-binding protein 7 × C-C motif chemokine 24 | 63 | | − | − | − |
| Insulin-like growth factor-binding protein 7 × Metalloproteinase inhibitor 2/(Alpha-1 antitrypsin) | 64 | | − | − | − |
| Hyaluronic acid × Neutrophil elastase × Metalloproteinase inhibitor 2 | 65 | | − | − | − |
| Immunoglobulin A × Hepatocyte growth factor/(Alpha-1 antitrypsin) | 66 | | − | − | − |
| Serum amyloid P-component × Hepatocyte growth factor/(Alpha-1 antitrypsin) | 67 | | − | − | − |
| Neutrophil elastase × Insulin-like growth factor-binding protein 7/(Alpha-1 antitrypsin) | 68 | | − | − | − |
| Hyaluronic acid × Neutrophil elastase × Cathepsin D | 69 | | − | − | − |
| Insulin-like growth factor-binding protein 7 × Immunoglobulin G1/(Alpha-1 antitrypsin) | 70 | | − | − | − |
| Hyaluronic acid × Insulin-like growth factor-binding protein 7 × Metalloproteinase inhibitor 2 | 71 | | − | − | − |
| Immunoglobulin A × Metalloproteinase inhibitor 2/(Alpha-1 antitrypsin) | 72 | | − | − | − |
| Hyaluronic acid × Beta-2-glycoprotein 1 × Insulin-like growth factor-binding protein 7 | 73 | | − | − | − |

TABLE 9-continued

Significance of exemplary three marker panels, analysis E, product model; "−" if p < 0.05, and as "+" if p ≥ 0.05

| | Panel # | Analysis | sCr E | sCr_UO E | UO E |
|---|---|---|---|---|---|
| Neutrophil elastase × Metalloproteinase inhibitor 2 × Hepatocyte growth factor | 74 | | − | − | − |
| Hyaluronic acid × Neutrophil elastase × Hepatocyte growth factor | 75 | | − | − | − |
| Neutrophil elastase × Insulin-like growth factor-binding protein 7 × Cathepsin D | 76 | | − | − | − |
| Neutrophil elastase × Tumor necrosis factor receptor superfamily member 11B/(Alpha-1 antitrypsin) | 77 | | − | − | − |
| Beta-2-glycoprotein 1 × Insulin-like growth factor-binding protein 7/(Alpha-1 antitrypsin) | 78 | | − | − | − |
| Neutrophil elastase × Metalloproteinase inhibitor 2/(Alpha-1 antitrypsin) | 79 | | − | − | − |
| Insulin-like growth factor-binding protein 7 × Hepatocyte growth factor/(Alpha-1 antitrypsin) | 80 | | − | − | − |
| Beta-2-glycoprotein 1 × Hyaluronic acid/(Alpha-1 antitrypsin) | 81 | | − | − | − |
| Neutrophil elastase × Insulin-like growth factor-binding protein 7 × Hepatocyte growth factor | 82 | | − | − | − |
| Serum amyloid P-component × Insulin-like growth factor-binding protein 7/(Alpha-1 antitrypsin) | 83 | | − | − | − |
| Neutrophil elastase × Beta-2-glycoprotein 1 × Insulin-like growth factor-binding protein 7 | 84 | | − | − | − |
| Neutrophil elastase × Insulin-like growth factor-binding protein 7 × Metalloproteinase inhibitor 2 | 85 | | − | − | − |
| Beta-2-glycoprotein 1 × Insulin-like growth factor-binding protein 7 × Metalloproteinase inhibitor 2 | 86 | | − | − | − |
| Beta-2-glycoprotein 1 × Hepatocyte growth factor/(Alpha-1 antitrypsin) | 87 | | − | − | − |
| Hyaluronic acid × Insulin-like growth factor-binding protein 7 × Immunoglobulin A | 88 | | − | − | − |
| Serum amyloid P-component × Metalloproteinase inhibitor 2/(Alpha-1 antitrypsin) | 89 | | − | − | − |
| Metalloproteinase inhibitor 2 × Hepatocyte growth factor/(Alpha-1 antitrypsin) | 90 | | − | − | − |
| Hyaluronic acid × Immunoglobulin G1/(Alpha-1 antitrypsin) | 91 | | − | − | − |
| Hyaluronic acid × Metalloproteinase inhibitor 2/(Alpha-1 antitrypsin) | 92 | | − | − | − |
| Neutrophil elastase × Serum amyloid P-component/(Alpha-1 antitrypsin) | 93 | | − | − | − |
| Beta-2-glycoprotein 1 × Metalloproteinase inhibitor 2/(Intercellular adhesion molecule 1) | 94 | | − | − | − |

TABLE 10

Significance of exemplary three marker panels, analysis E, logistic regression model; "−" if p < 0.05, and as "+" if p ≥ 0.05

| | Panel # | Analysis | sCr E | sCr_UO E | UO E |
|---|---|---|---|---|---|
| Neutrophil elastase; Hyaluronic acid; Interleukin-11 | 1 | | − | − | − |
| Macrophage colony-stimulating factor 1; Neutrophil elastase; (Alpha-1 antitrypsin) | 2 | | − | − | − |
| Serum amyloid P-component; Neutrophil elastase; C-C motif chemokine 24 | 3 | | − | − | − |
| Neutrophil elastase; Insulin-like growth factor-binding protein 7; C-X-C motif chemokine 6 | 4 | | − | − | − |
| Serum amyloid P-component; Neutrophil elastase; Hepatocyte growth factor | 5 | | − | − | − |
| Hyaluronic acid; Neutrophil elastase; Immunoglobulin G2 | 6 | | − | − | − |
| Beta-2-glycoprotein 1; Insulin-like growth factor-binding protein 7; Interleukin-11 | 7 | | − | − | − |
| Cathepsin D; Neutrophil elastase; Hepatocyte growth factor | 8 | | − | − | − |
| Immunoglobulin G1; Hepatocyte growth factor; (Alpha-1 antitrypsin) | 9 | | − | − | − |
| Insulin-like growth factor-binding protein 7; Interleukin-1 beta; (Alpha-1 antitrypsin) | 10 | | − | − | − |
| Serum amyloid P-component; Insulin-like growth factor-binding protein 7; Interleukin-11 | 11 | | − | − | − |
| Neutrophil elastase; Immunoglobulin A; Metalloproteinase inhibitor 2 | 12 | | − | − | − |
| Insulin-like growth factor-binding protein 7; Metalloproteinase inhibitor 2; Hepatocyte growth factor | 13 | | − | − | − |
| Neutrophil elastase; Cathepsin D; (Alpha-1 antitrypsin) | 14 | | − | − | − |
| C-C motif chemokine 24; Neutrophil elastase; Metalloproteinase inhibitor 2 | 15 | | − | − | − |
| Neutrophil elastase; Insulin-like growth factor-binding protein 7; Immunoglobulin G1 | 16 | | − | − | − |
| Hyaluronic acid; Immunoglobulin A; Metalloproteinase inhibitor 2 | 17 | | − | − | − |
| Neutrophil elastase; Hyaluronic acid; Immunoglobulin G1 | 18 | | − | − | − |
| Hyaluronic acid; Insulin-like growth factor-binding protein 7; Cathepsin D | 19 | | − | − | − |
| Hyaluronic acid; Insulin-like growth factor-binding protein 7; Hepatocyte growth factor | 20 | | − | − | − |
| C-C motif chemokine 24; Serum amyloid P-component; (Alpha-1 antitrypsin) | 21 | | − | − | − |
| Insulin-like growth factor-binding protein 7; Interleukin-11; Metalloproteinase inhibitor 2 | 22 | | − | − | − |
| Serum amyloid P-component; Insulin-like growth factor-binding protein 7; Metalloproteinase inhibitor 2 | 23 | | − | − | − |
| Hyaluronic acid; Neutrophil elastase; Immunoglobulin A | 24 | | − | − | − |
| Hyaluronic acid; Insulin-like growth factor-binding protein 7; Immunoglobulin G1 | 25 | | − | − | − |
| Neutrophil elastase; Insulin-like growth factor-binding protein 7; Interleukin-11 | 26 | | − | − | − |

TABLE 10-continued

Significance of exemplary three marker panels, analysis E, logistic regression model; "−" if p < 0.05, and as "+" if p ≥ 0.05

|  | Panel # | Analysis | sCr E | sCr_UO E | UO E |
|---|---|---|---|---|---|
| Hyaluronic acid; Serum amyloid P-component; Metalloproteinase inhibitor 2 | 27 |  | − | − | − |
| Immunoglobulin G1; Metalloproteinase inhibitor 2; (Alpha-1 antitrypsin) | 28 |  | − | − | − |
| Neutrophil elastase; Serum amyloid P-component; Metalloproteinase inhibitor 2 | 29 |  | − | − | − |
| Neutrophil elastase; Beta-2-glycoprotein 1; Metalloproteinase inhibitor 2 | 30 |  | − | − | − |
| Interleukin-2 receptor alpha chain; Neutrophil elastase; (Alpha-1 antitrypsin) | 31 |  | − | − | − |
| Immunoglobulin G2; Insulin-like growth factor-binding protein 7; (Alpha-1 antitrypsin) | 32 |  | − | − | − |
| Hyaluronic acid; Beta-2-glycoprotein 1; Metalloproteinase inhibitor 2 | 33 |  | − | − | − |
| Interleukin-11; Serum amyloid P-component; (Alpha-1 antitrypsin) | 34 |  | − | − | − |
| Insulin-like growth factor-binding protein 7; Immunoglobulin A; Metalloproteinase inhibitor 2 | 35 |  | − | − | − |
| Beta-2-glycoprotein 1; Insulin-like growth factor-binding protein 7; Hepatocyte growth factor | 36 |  | − | − | − |
| Hyaluronic acid; Neutrophil elastase; Beta-2-glycoprotein 1 | 37 |  | − | − | − |
| Matrilysin; Neutrophil elastase; (Alpha-1 antitrypsin) | 38 |  | − | − | − |
| Hyaluronic acid; Neutrophil elastase; C-C motif chemokine 24 | 39 |  | − | − | − |
| Metalloproteinase inhibitor 2; Neutrophil elastase; Tumor necrosis factor receptor superfamily member 11B | 40 |  | − | − | − |
| Neutrophil elastase; Hepatocyte growth factor; (Alpha-1 antitrypsin) | 41 |  | − | − | − |
| Insulin-like growth factor-binding protein 3; Neutrophil elastase; (Alpha-1 antitrypsin) | 42 |  | − | − | − |
| Neutrophil elastase; Insulin-like growth factor-binding protein 7; Immunoglobulin A | 43 |  | − | − | − |
| Hyaluronic acid; Insulin-like growth factor-binding protein 7; C-C motif chemokine 13 | 44 |  | − | − | − |
| Hyaluronic acid; Serum amyloid P-component; Insulin-like growth factor-binding protein 7 | 45 |  | − | − | − |
| Hyaluronic acid; Neutrophil elastase; Tumor necrosis factor receptor superfamily member 11B | 46 |  | − | − | − |
| Insulin-like growth factor-binding protein 7; Immunoglobulin A; (Alpha-1 antitrypsin) | 47 |  | − | − | − |
| Hyaluronic acid; Insulin-like growth factor-binding protein 7; Interleukin-11 | 48 |  | − | − | − |
| Insulin-like growth factor-binding protein 7; Neutrophil elastase; Tumor necrosis factor receptor superfamily member 11B | 49 |  | − | − | − |
| Neutrophil elastase; Serum amyloid P-component; Insulin-like growth factor-binding protein 7 | 50 |  | − | − | − |
| Hyaluronic acid; Hepatocyte growth factor; (Alpha-1 antitrypsin) | 51 |  | − | − | − |
| Neutrophil elastase; Immunoglobulin A; (Alpha-1 antitrypsin) | 52 |  | − | − | − |
| Beta-2-glycoprotein 1; Neutrophil elastase; (Alpha-1 antitrypsin) | 53 |  | − | − | − |
| Hyaluronic acid; Insulin-like growth factor-binding protein 7; (Alpha-1 antitrypsin) | 54 |  | − | − | − |
| Hyaluronic acid; Immunoglobulin A; (Alpha-1 antitrypsin) | 55 |  | − | − | − |
| Hyaluronic acid; Serum amyloid P-component; (Alpha-1 antitrypsin) | 56 |  | − | − | − |
| Neutrophil elastase; C-C motif chemokine 24; (Alpha-1 antitrypsin) | 57 |  | − | − | − |
| Hyaluronic acid; Neutrophil elastase; (Alpha-1 antitrypsin) | 58 |  | − | − | − |
| Hyaluronic acid; Neutrophil elastase; Insulin-like growth factor-binding protein 7 | 59 |  | − | − | − |
| Neutrophil elastase; Cathepsin D; Metalloproteinase inhibitor 2 | 60 |  | − | − | − |
| Beta-2-glycoprotein 1; Metalloproteinase inhibitor 2; (Alpha-1 antitrypsin) | 61 |  | − | − | − |
| Hyaluronic acid; Neutrophil elastase; Serum amyloid P-component | 62 |  | − | − | − |
| Neutrophil elastase; Insulin-like growth factor-binding protein 7; C-C motif chemokine 24 | 63 |  | − | − | − |
| Insulin-like growth factor-binding protein 7; Metalloproteinase inhibitor 2; (Alpha-1 antitrypsin) | 64 |  | − | − | − |
| Hyaluronic acid; Neutrophil elastase; Metalloproteinase inhibitor 2 | 65 |  | − | − | − |
| Immunoglobulin A; Hepatocyte growth factor; (Alpha-1 antitrypsin) | 66 |  | − | − | − |
| Serum amyloid P-component; Hepatocyte growth factor; (Alpha-1 antitrypsin) | 67 |  | − | − | − |
| Neutrophil elastase; Insulin-like growth factor-binding protein 7; (Alpha-1 antitrypsin) | 68 |  | − | − | − |
| Hyaluronic acid; Neutrophil elastase; Cathepsin D | 69 |  | − | − | − |
| Insulin-like growth factor-binding protein 7; Immunoglobulin G1; (Alpha-1 antitrypsin) | 70 |  | − | − | − |
| Hyaluronic acid; Insulin-like growth factor-binding protein 7; Metalloproteinase inhibitor 2 | 71 |  | − | − | − |
| Immunoglobulin A; Metalloproteinase inhibitor 2; (Alpha-1 antitrypsin) | 72 |  | − | − | − |
| Hyaluronic acid; Beta-2-glycoprotein 1; Insulin-like growth factor-binding protein 7 | 73 |  | − | − | − |
| Neutrophil elastase; Metalloproteinase inhibitor 2; Hepatocyte growth factor | 74 |  | − | − | − |
| Hyaluronic acid; Neutrophil elastase; Hepatocyte growth factor | 75 |  | − | − | − |
| Neutrophil elastase; Insulin-like growth factor-binding protein 7; Cathepsin D | 76 |  | − | − | − |
| Neutrophil elastase; Tumor necrosis factor receptor superfamily member 11B; (Alpha-1 antitrypsin) | 77 |  | − | − | − |
| Beta-2-glycoprotein 1; Insulin-like growth factor-binding protein 7; (Alpha-1 antitrypsin) | 78 |  | − | − | − |
| Neutrophil elastase; Metalloproteinase inhibitor 2; (Alpha-1 antitrypsin) | 79 |  | − | − | − |
| Insulin-like growth factor-binding protein 7; Hepatocyte growth factor; (Alpha-1 antitrypsin) | 80 |  | − | − | − |
| Beta-2-glycoprotein 1; Hyaluronic acid; (Alpha-1 antitrypsin) | 81 |  | − | − | − |

TABLE 10-continued

Significance of exemplary three marker panels, analysis E, logistic regression model; "−" if p < 0.05, and as "+" if p ≥ 0.05

| | Panel # | Analysis | sCr E | sCr_UO E | UO E |
|---|---|---|---|---|---|
| Neutrophil elastase; Insulin-like growth factor-binding protein 7; Hepatocyte growth factor | 82 | | − | − | − |
| Serum amyloid P-component; Insulin-like growth factor-binding protein 7; (Alpha-1 antitrypsin) | 83 | | − | − | − |
| Neutrophil elastase; Beta-2-glycoprotein 1; Insulin-like growth factor-binding protein 7 | 84 | | − | − | − |
| Neutrophil elastase; Insulin-like growth factor-binding protein 7; Metalloproteinase inhibitor 2 | 85 | | − | − | − |
| Beta-2-glycoprotein 1; Insulin-like growth factor-binding protein 7; Metalloproteinase inhibitor 2 | 86 | | − | − | − |
| Beta-2-glycoprotein 1; Hepatocyte growth factor; (Alpha-1 antitrypsin) | 87 | | − | − | − |
| Hyaluronic acid; Insulin-like growth factor-binding protein 7; Immunoglobulin A | 88 | | − | − | − |
| Serum amyloid P-component; Metalloproteinase inhibitor 2; (Alpha-1 antitrypsin) | 89 | | − | − | − |
| Metalloproteinase inhibitor 2; Hepatocyte growth factor; (Alpha-1 antitrypsin) | 90 | | − | − | − |
| Hyaluronic acid; Immunoglobulin G1; (Alpha-1 antitrypsin) | 91 | | − | − | − |
| Hyaluronic acid; Metalloproteinase inhibitor 2; (Alpha-1 antitrypsin) | 92 | | − | − | − |
| Neutrophil elastase; Serum amyloid P-component; (Alpha-1 antitrypsin) | 93 | | − | − | − |
| Beta-2-glycoprotein 1; Metalloproteinase inhibitor 2; (Intercellular adhesion molecule 1) | 94 | | − | − | − |

TABLE 11

Significance of exemplary three marker panels, product model; Panel numbers are as listed in Table 7; "−" if p < 0.05, and as "+" if p ≥ 0.05

| | | | |
|---|---|---|---|
| sCr | 0 hrs prior to AKI stage | A | 3, 5, 9, 11, 14, 16, 21, 22, 23, 28, 29, 32, 34, 38, 41, 42, 47, 49, 50, 51, 52, 53, 54, 55, 56, 57, 58, 61, 63, 64, 66, 67, 68, 70, 72, 77, 78, 79, 80, 81, 83, 87, 89, 90, 91, 92, 93 |
| | | B | 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 3, 9, 10, 11, 12, 14, 15, 16, 17, 18, 21, 23, 25, 27, 28, 29, 32, 34, 35, 38, 39, 40, 41, 42, 43, 45, 46, 47, 49, 50, 51, 52, 53, 54, 55, 56, 57, 58, 60, 61, 62, 63, 64, 66, 67, 68, 70, 72, 77, 78, 79, 80, 81, 83, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | 48 hrs prior to AKI stage | A | 32, 70 |
| | | B | 3, 5, 9, 11, 13, 14, 15, 17, 19, 20, 21, 22, 23, 25, 27, 28, 29, 32, 34, 35, 36, 41, 42, 44, 45, 47, 48, 50, 51, 52, 53, 54, 55, 56, 57, 61, 62, 63, 64, 66, 67, 68, 70, 71, 72, 77, 78, 79, 80, 81, 83, 86, 87, 88, 89, 90, 91, 92, 93, 94 |
| | | C | 5, 7, 9, 10, 11, 13, 17, 19, 20, 21, 22, 23, 25, 27, 32, 33, 34, 35, 36, 44, 45, 47, 48, 51, 54, 55, 56, 61, 64, 66, 67, 70, 71, 73, 78, 80, 81, 83, 86, 87, 88, 89, 90, 91, 92 |
| | | D | 2, 3, 4, 5, 6, 7, 8, 9, 10, 11, 12, 13, 16, 17, 18, 19, 20, 21, 22, 23, 25, 26, 27, 28, 29, 30, 31, 32, 33, 34, 35, 36, 37, 38, 40, 42, 43, 44, 45, 46, 47, 48, 49, 50, 51, 53, 54, 55, 56, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| sCr_UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | 48 hrs prior to AKI stage | A | 8, 9, 20, 28, 41, 46, 51, 54, 55, 56, 58, 66, 67, 69, 74, 75, 80, 82, 89, 90, 91, 92 |
| | | B | 3, 5, 8, 9, 11, 12, 13, 16, 17, 18, 19, 20, 21, 22, 23, 25, 27, 28, 29, 32, 33, 34, 35, 36, 40, 43, 44, 45, 46, 47, 48, 49, 50, 51, 54, 55, 56, 57, 59, 60, 62, 63, 64, 65, 66, 67, 70, 71, 72, 73, 74, 75, 76, 77, 78, 80, 81, 82, 83, 85, 86, 87, 88, 89, 90, 91, 92, 93 |
| | | C | 45 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |

TABLE 11-continued

Significance of exemplary three marker panels, product model; Panel numbers are as listed in Table 7; "−" if p < 0.05, and as "+" if p ≥ 0.05

| | | | |
|---|---|---|---|
| UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | 48 hrs prior to AKI stage | A | 8, 9, 10, 19, 20, 25, 36, 41, 46, 51, 54, 55, 56, 66, 67, 75, 80, 81, 87, 90, 91, 92 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |

TABLE 12

Significance of exemplary three marker panels, logistic regression model; Panel numbers are as listed in Table 8; "−" if p < 0.05, and as "+" if p ≥ 0.05

| | | | |
|---|---|---|---|
| sCr | 0 hrs prior to AKI stage | A | 1, 2, 3, 5, 9, 10, 11, 13, 14, 17, 18, 19, 20, 21, 22, 23, 25, 26, 27, 28, 29, 31, 32, 33, 34, 35, 37, 38, 39, 41, 42, 43, 44, 45, 46, 47, 48, 49, 50, 51, 52, 53, 54, 55, 56, 57, 58, 59, 60, 61, 62, 64, 65, 66, 67, 68, 69, 70, 71, 72, 73, 75, 76, 77, 78, 79, 80, 81, 83, 87, 88, 89, 90, 91, 92, 93, 94 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 2, 3, 5, 6, 8, 9, 10, 11, 12, 13, 14, 15, 16, 17, 18, 19, 20, 21, 22, 23, 24, 25, 27, 28, 29, 31, 32, 33, 34, 35, 38, 39, 40, 41, 42, 43, 44, 45, 46, 47, 49, 50, 51, 52, 53, 54, 55, 56, 57, 58, 60, 61, 62, 63, 64, 65, 66, 67, 68, 69, 70, 71, 72, 74, 76, 77, 78, 79, 80, 81, 82, 83, 85, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | 48 hrs prior to AKI stage | A | 2, 3, 4, 5, 8, 9, 10, 11, 14, 15, 16, 20, 22, 26, 31, 32, 36, 38, 40, 41, 42, 49, 50, 51, 52, 53, 56, 57, 58, 59, 63, 68, 70, 75, 76, 77, 79, 84, 93 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 2, 3, 4, 5, 6, 7, 8, 9, 10, 11, 12, 13, 14, 15, 16, 17, 18, 19, 20, 21, 22, 23, 25, 26, 27, 28, 29, 30, 32, 34, 35, 36, 37, 38, 40, 41, 42, 43, 44, 45, 46, 47, 48, 49, 50, 51, 52, 53, 54, 55, 56, 57, 58, 59, 60, 61, 62, 63, 65, 66, 67, 68, 69, 70, 72, 73, 74, 75, 76, 77, 78, 79, 80, 81, 82, 83, 84, 85, 87, 88, 89, 90, 91, 92, 93 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| sCr_UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |

TABLE 12-continued

Significance of exemplary three marker panels, logistic regression model; Panel numbers are as listed in Table 8; "−" if p < 0.05, and as "+" if p ≥ 0.05

| | | | |
|---|---|---|---|
| | 48 hrs prior to AKI stage | A | 1, 5, 6, 8, 9, 13, 14, 17, 18, 19, 20, 22, 24, 25, 26, 27, 28, 30, 33, 36, 37, 38, 39, 41, 42, 44, 45, 46, 48, 51, 52, 53, 54, 55, 56, 58, 59, 61, 62, 64, 65, 66, 67, 68, 69, 70, 71, 72, 73, 74, 75, 79, 80, 81, 82, 84, 86, 87, 88, 89, 90, 91, 92, 93 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 1, 3, 4, 5, 7, 10, 11, 12, 13, 15, 16, 19, 20, 21, 22, 23, 24, 25, 26, 27, 32, 34, 35, 36, 39, 40, 43, 44, 45, 47, 48, 49, 50, 52, 54, 56, 59, 63, 64, 66, 67, 68, 70, 71, 73, 76, 77, 78, 80, 82, 83, 84, 85, 86, 88 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| UO | 0 hrs prior to AKI stage | A | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | 48 hrs prior to AKI stage | A | 1, 5, 6, 8, 9, 13, 17, 18, 19, 20, 24, 25, 26, 27, 33, 36, 37, 39, 40, 41, 42, 44, 45, 46, 48, 49, 51, 54, 55, 56, 58, 59, 62, 65, 66, 67, 69, 71, 73, 74, 75, 77, 80, 81, 82, 87, 88, 90, 91, 92 |
| | | B | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |
| | | C | 3, 7, 11, 12, 13, 17, 21, 22, 23, 26, 35, 36, 43, 45, 47, 48, 52, 63, 66, 71, 72, 73, 78, 84, 86, 88 |
| | | D | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 |

For exemplary purposes, the patient population from a selected set of the foregoing analyses was segregated based on the panel results using threshold values which divided the population into thirds ("tertiles"). Patients with panel results in the lower, middle, and upper third comprise the first, second, and third tertiles, respectively. The relative risk of reaching the inidicated AKI stage was calculated for the second and third tertiles, relative to a value of 1 for the first tertile, as indicated in the following tables 13 and 14.

TABLE 13

Relative risk of developing at least RIFLE I (Analysis B and E) or RIFLE F (Analysis C) for exemplary 2-Marker Panels.

| | Analysis B | | | | Analysis C | | | | Analysis E | | | |
|---|---|---|---|---|---|---|---|---|---|---|---|---|
| Panel | T2 | p2 | T3 | p3 | T2 | p2 | T3 | p3 | T2 | p2 | T3 | p3 |
| Neutrophil elastase × Insulin-like growth factor-binding protein 7 | 3.3 | 7.0E−02 | 11.3 | 6.7E−05 | >2.0 | <0.57 | >13.0 | <0.014 | 3.0 | 1.9E−01 | 11.9 | 9.4E−04 |
| Hyaluronic acid × Neutrophil elastase | 2.0 | 2.7E−01 | 8.7 | 5.3E−05 | >1 | <1 | >14.0 | <0.011 | 1.7 | 4.9E−01 | 7.9 | 9.7E−04 |
| Neutrophil elastase × Metalloproteinase inhibitor 2 | 3.0 | 1.0E−01 | 11.6 | 5.5E−05 | >1.0 | <1 | >14.0 | <0.011 | 2.0 | 4.3E−01 | 12.9 | 6.2E−04 |
| Hyaluronic acid × Insulin-like growth factor-binding protein 7 | 3.0 | 1.0E−01 | 12.0 | 4.5E−05 | 1.0 | 1.0 | 14.0 | 1.1E−02 | 3.0 | 1.9E−01 | 11.9 | 9.4E−04 |
| Insulin-like growth factor-binding protein 7 × Metalloproteinase inhibitor 2 | 1.7 | 3.8E−01 | 9.2 | 3.2E−05 | 1.0 | 1.0 | 14.0 | 1.1E−02 | 2.5 | 2.8E−01 | 12.4 | 7.6E−04 |
| Neutrophil elastase × Hepatocyte growth factor | 2.7 | 1.5E−01 | 12.0 | 4.5E−05 | >1 | <1 | >14.0 | <0.011 | 1.3 | 7.1E−01 | 8.3 | 7.4E−04 |
| Hyaluronic acid × Metalloproteinase inhibitor 2 | 3.0 | 1.0E−01 | 12.0 | 4.3E−05 | 3.0 | 3.4E−01 | 12.0 | 1.7E−02 | 2.0 | 3.4E−01 | 7.6 | 1.3E−03 |
| Beta-2-glycoprotein 1 × Insulin-like growth factor-binding protein 7 | 3.0 | 1.0E−01 | 12.0 | 4.5E−05 | 0.0 | na | 15.0 | 8.9E−03 | 4.5 | 6.0E−02 | 10.4 | 1.9E−03 |

TABLE 13-continued

Relative risk of developing at least RIFLE I (Analysis B and E) or RIFLE F (Analysis C) for exemplary 2-Marker Panels.

| | Analysis B | | | | Analysis C | | | | Analysis E | | | |
|---|---|---|---|---|---|---|---|---|---|---|---|---|
| Panel | T2 | p2 | T3 | p3 | T2 | p2 | T3 | p3 | T2 | p2 | T3 | p3 |
| Insulin-like growth factor-binding protein 7 × Hepatocyte growth factor | 6.0 | 2.0E−02 | 16.9 | 1.1E−04 | 2.0 | 5.7E−01 | 13.0 | 1.4E−02 | 3.5 | 1.2E−01 | 11.4 | 1.2E−03 |
| Insulin-like growth factor-binding protein 7 × CXCL-1-2 and -3 | 6.5 | 1.4E−02 | 16.5 | 1.3E−04 | >3.0 | <0.34 | >13.0 | <0.014 | >9.0 | <0.038 | >23 | <0.0023 |
| Insulin-like growth factor-binding protein 7 × Immunoglobulin A | 1.2 | 7.7E−01 | 7.4 | 3.7E−05 | 0.0 | na | 15.0 | 8.9E−03 | 2.3 | 2.3E−01 | 7.3 | 1.7E−03 |
| Neutrophil elastase × Tumor necrosis factor receptor superfamily member 11B | 2.3 | 1.8E−01 | 8.5 | 6.8E−05 | >2 | <0.57 | >13.0 | <0.014 | 2.5 | 2.8E−01 | 12.4 | 7.6E−04 |
| Serum amyloid P-component × Insulin-like growth factor-binding protein 7 | 3.3 | 7.1E−02 | 11.6 | 5.5E−05 | 2.0 | 5.7E−01 | 13.0 | 1.4E−02 | 3.5 | 1.2E−01 | 11.5 | 1.1E−03 |
| Hyaluronic acid × Serum amyloid P-component | 4.0 | 3.3E−02 | 11.0 | 8.4E−05 | 2.0 | 5.7E−01 | 13.0 | 1.4E−02 | 3.5 | 1.2E−01 | 11.4 | 1.2E−03 |
| Insulin-like growth factor-binding protein 7/(Alpha-1 antitrypsin) | 1.0 | 1.0E+00 | 7.6 | 2.9E−05 | 0.0 | na | 15.0 | 9.0E−03 | 4.0 | 8.4E−02 | 10.9 | 1.5E−03 |
| Interleukin-11 × Metalloproteinase inhibitor 2 | 4.0 | 3.3E−02 | 10.7 | 1.1E−04 | >2.0 | <0.57 | >13.0 | <0.014 | 7.9 | 5.3E−02 | 21.8 | 2.8E−03 |
| Hyaluronic acid × Interleukin-11 | 1.8 | 3.0E−01 | 6.6 | 1.2E−04 | 1.0 | 1.0 | 13.0 | 1.4E−02 | 1.7 | 4.9E−01 | 7.6 | 1.3E−03 |
| Insulin-like growth factor-binding protein 7 × Interleukin-11 | 4.0 | 3.3E−02 | 10.6 | 1.1E−04 | >2.0 | <0.57 | >13.0 | <0.014 | 9.0 | 3.9E−02 | 21.0 | 3.2E−03 |
| Hyaluronic acid/(Alpha-1 antitrypsin) | 3.0 | 1.0E−01 | 12.0 | 4.5E−05 | 1.0 | 1.0 | 14.0 | 1.1E−02 | 10.9 | 2.3E−02 | 19.8 | 3.9E−03 |
| Hyaluronic acid × Immunoglobulin A | 1.0 | 9.9E−01 | 6.0 | 7.1E−05 | 2.0 | 5.7E−01 | 13.0 | 1.4E−02 | 2.7 | 1.6E−01 | 7.0 | 2.1E−03 |
| Immunoglobulin A × Metalloproteinase inhibitor 2 | 1.8 | 3.8E−01 | 9.2 | 3.2E−05 | 0.0 | na | 15.0 | 9.0E−03 | 4.0 | 8.4E−02 | 10.9 | 1.5E−03 |
| Beta-2-glycoprotein 1 × Metalloproteinase inhibitor 2 | 1.6 | 4.2E−01 | 7.0 | 6.4E−05 | 0.0 | na | 15.0 | 8.9E−03 | 2.0 | 3.4E−01 | 7.6 | 1.3E−03 |
| Metalloproteinase inhibitor 2/(Alpha-1 antitrypsin) | 4.3 | 2.4E−02 | 10.6 | 1.1E−04 | 1.0 | 1.0 | 14.0 | 1.1E−02 | >10.0 | <0.029 | >22 | <0.0027 |
| Serum amyloid P-component × Metalloproteinase inhibitor 2 | 2.5 | 1.3E−01 | 8.5 | 6.6E−05 | 2.0 | 5.7E−01 | 13.0 | 1.4E−02 | 3.5 | 1.3E−01 | 11.4 | 1.2E−03 |
| Hyaluronic acid × Beta-2-glycoprotein 1 | 1.8 | 3.0E−01 | 6.8 | 8.7E−05 | 2.0 | 5.7E−01 | 13.0 | 1.4E−02 | 1.5 | 5.4E−01 | 5.5 | 2.4E−03 |

Collection time is 24 hr prior to RIFLE I for Analysis B and C. Collection time is at enrollment for Analysis E, and subjects at RIFLE stage I or F at enrollment were excluded. T2, p2, T3, and p3 are the relative risk and corresponding p value for the second and third tertile (relative to the first tertile), respsectively.

TABLE 14

Relative risk of developing at least RIFLE I (Analysis B and E) or RIFLE F (Analysis C) for exemplary 3-Marker Panels.

| | Analysis B | | | | Analysis C | | | | Analysis E | | | |
|---|---|---|---|---|---|---|---|---|---|---|---|---|
| Panel | T2 | p2 | T3 | p3 | T2 | p2 | T3 | p3 | T2 | p2 | T3 | p3 |
| Hyaluronic acid × Beta-2-glycoprotein 1/(Alpha-1 antitrypsin) | 5.0 | 4.0E−02 | 17.9 | 8.1E−05 | >3.0 | <3.4E−01 | >13.0 | <1.4E−02 | >9.1 | <3.8E−02 | >23.2 | <2.3E−03 |
| Beta-2-glycoprotein 1 × Insulin-like growth factor-binding protein 7/(Alpha-1 antitrypsin) | 5.0 | 3.9E−02 | 17.9 | 8.1E−05 | >2.0 | <5.7E−01 | >14.0 | <1.1E−02 | >7.0 | <7.1E−02 | >25.0 | <1.8E−03 |
| Beta-2-glycoprotein 1 × Metalloproteinase inhibitor 2/(Alpha-1 antitrypsin) | 5.5 | 2.8E−02 | 17.4 | 9.6E−05 | >2.0 | <5.7E−01 | >14.0 | <1.1E−02 | >9.0 | <3.9E−02 | >23.0 | <2.3E−03 |
| Hyaluronic acid × Neutrophil elastase × Insulin-like growth factor-binding protein 7 | 3.0 | 1.0E−01 | 11.6 | 5.5E−05 | >2.0 | <5.7E−01 | >13.0 | <1.4E−02 | 3.5 | 1.2E−01 | 11.4 | 1.2E−03 |
| Neutrophil elastase × Insulin-like growth factor-binding protein 7 × Cathepsin D | 3.0 | 1.0E−01 | 11.7 | 5.4E−05 | >2.0 | <5.7E−01 | >13.0 | <1.4E−02 | 6.9 | 7.2E−02 | 23.8 | 2.1E−03 |
| Hyaluronic acid × Neutrophil elastase/(Alpha-1 antitrypsin) | 2.7 | 1.5E−01 | 12.0 | 4.5E−05 | >1.0 | <1.0E00 | >14.0 | <1.1E−02 | 3.5 | 1.2E−01 | 11.4 | 1.2E−03 |
| Insulin-like growth factor-binding protein 7 × Hepatocyte growth factor/(Alpha-1 antitrypsin) | 2.3 | 2.2E−01 | 12.6 | 2.9E−05 | 0.0 | na | 15.0 | 9.0E−03 | >6.1 | <9.8E−02 | >26.0 | <1.5E−03 |

TABLE 14-continued

Relative risk of developing at least RIFLE I (Analysis B and E) or RIFLE F (Analysis C) for exemplary 3-Marker Panels.

| Panel | Analysis B | | | | Analysis C | | | | Analysis E | | | |
|---|---|---|---|---|---|---|---|---|---|---|---|---|
| | T2 | p2 | T3 | p3 | T2 | p2 | T3 | p3 | T2 | p2 | T3 | p3 |
| Insulin-like growth factor-binding protein 7 × Immunoglobulin A/(Alpha-1 antitrypsin) | 5.0 | 3.9E−02 | 18.0 | 7.9E−05 | >1.0 | <1.0E00 | >15.0 | <8.9E−03 | >8.1 | <5.1E−02 | >24.0 | <2.0E−03 |
| Hyaluronic acid × Insulin-like growth factor-binding protein 7/(Alpha-1 antitrypsin) | 2.3 | 2.3E−01 | 12.6 | 2.9E−05 | >1.0 | <1.0E00 | >15.0 | <8.9E−03 | 5.9 | 1.0E−01 | 24.8 | 1.8E−03 |
| Neutrophil elastase × Hepatocyte growth factor/(Alpha-1 antitrypsin) | 5.0 | 3.9E−02 | 17.5 | 9.4E−05 | >1.0 | <1.0E00 | >14.0 | <1.1E−02 | 2.5 | 2.8E−01 | 12.4 | 7.6E−04 |
| Neutrophil elastase × Insulin-like growth factor-binding protein 7/(Alpha-1 antitrypsin) | 2.0 | 2.6E−01 | 8.8 | 5.1E−05 | >1.0 | <1.0E00 | >14.0 | <1.1E−02 | 7.9 | 5.3E−02 | 22.8 | 2.4E−03 |
| Hyaluronic acid × Immunoglobulin A/(Alpha-1 antitrypsin) | 4.0 | 8.2E−02 | 18.9 | 5.8E−05 | >2.0 | <5.7E−01 | >14.0 | <1.1E−02 | >8.1 | <5.1E−02 | >24.2 | <2.0E−03 |
| Neutrophil elastase × Insulin-like growth factor-binding protein 7 × Hepatocyte growth factor | 5.5 | 2.8E−02 | 17.0 | 1.1E−04 | >2.0 | <5.7E−01 | >13.0 | <1.4E−02 | 3.5 | 1.3E−01 | 11.4 | 1.2E−03 |
| Neutrophil elastase × Insulin-like growth factor-binding protein 7 × Metalloproteinase inhibitor 2 | 3.0 | 1.0E−01 | 11.6 | 5.5E−05 | >2.0 | <5.7E−01 | >13.0 | <1.4E−02 | 3.5 | 1.3E−01 | 11.4 | 1.2E−03 |
| Neutrophil elastase × Metalloproteinase inhibitor 2/(Alpha-1 antitrypsin) | 1.8 | 3.8E−01 | 9.0 | 4.1E−05 | >1.0 | <1.0E00 | >14.0 | <1.1E−02 | 5.9 | 1.0E−01 | 24.8 | 1.8E−03 |
| Hyaluronic acid × Neutrophil elastase × Hepatocyte growth factor | 4.0 | 8.2E−02 | 18.4 | 6.8E−05 | >2.0 | <5.7E−01 | >13.0 | <1.4E−02 | 3.0 | 1.8E−01 | 11.9 | 9.4E−04 |
| Neutrophil elastase × Metalloproteinase inhibitor 2 × Hepatocyte growth factor | 4.5 | 5.7E−02 | 17.9 | 8.1E−05 | >2.0 | <5.7E−01 | >13.0 | <1.4E−02 | 2.5 | 2.8E−01 | 12.4 | 7.6E−04 |
| Neutrophil elastase × Serum amyloid P-component/(Alpha-1 antitrypsin) | 0.6 | 3.8E−01 | 5.1 | 1.1E−04 | 0.0 | na | 14.0 | 1.1E−02 | 3.0 | 1.8E−01 | 11.9 | 9.4E−04 |
| Hyaluronic acid × Serum amyloid P-component/(Alpha-1 antitrypsin) | 4.0 | 8.1E−02 | 19.0 | 5.6E−05 | >1.0 | <1.0E00 | >15.0 | <8.9E−03 | 4.0 | 2.2E−01 | 26.8 | 1.4E−03 |
| Neutrophil elastase × Tumor necrosis factor receptor superfamily member 11B/(Alpha-1 antitrypsin) | 2.0 | 2.6E−01 | 8.8 | 5.1E−05 | >1.0 | <1.0E00 | >14.0 | <1.1E−02 | 5.9 | 1.0E−01 | 24.8 | 1.8E−03 |
| Serum amyloid P-component × Insulin-like growth factor-binding protein 7/(Alpha-1 antitrypsin) | 2.0 | 3.3E−01 | 12.9 | 2.4E−05 | >2.0 | <5.7E−01 | >14.0 | <1.1E−02 | 5.0 | 1.4E−01 | 26.0 | 1.5E−03 |
| Hyaluronic acid × Neutrophil elastase × Cathepsin D | 1.5 | 5.4E−01 | 9.2 | 3.2E−05 | >1.0 | <1.0E00 | >14.0 | <1.1E−02 | 1.7 | 4.9E−01 | 7.9 | 9.7E−04 |
| Hyaluronic acid × Beta-2-glycoprotein 1 × Insulin-like growth factor-binding protein 7 | 3.3 | 7.1E−02 | 11.6 | 5.5E−05 | 0.0 | na | 15.0 | 9.0E−03 | 2.0 | 3.4E−01 | 7.7 | 1.2E−03 |
| Hyaluronic acid × Neutrophil elastase × Serum amyloid P-component | 1.4 | 5.7E−01 | 7.0 | 6.4E−05 | 1.0 | 1.0E00 | 13.0 | 1.4E−02 | 3.0 | 1.8E−01 | 12.0 | 9.0E−04 |
| Neutrophil elastase × Insulin-like growth factor-binding protein 7 × C-C motif chemokine 24 | 1.5 | 5.3E−01 | 9.2 | 3.2E−05 | 1.0 | 1.0E00 | 13.0 | 1.4E−02 | 8.0 | 5.2E−02 | 22.8 | 2.4E−03 |
| Metalloproteinase inhibitor 2 × Neutrophil elastase × Cathepsin D | 3.3 | 7.0E−02 | 11.3 | 6.9E−05 | >1.0 | <1.0E00 | >14.0 | <1.1E−02 | 5.0 | 1.5E−01 | 25.8 | 1.6E−03 |
| Hyaluronic acid × Neutrophil elastase × Metalloproteinase inhibitor 2 | 2.3 | 2.2E−01 | 12.3 | 3.5E−05 | >2.0 | <5.7E−01 | >13.0 | <1.4E−02 | 2.5 | 2.8E−01 | 12.4 | 7.6E−04 |

TABLE 14-continued

Relative risk of developing at least RIFLE I (Analysis B and E) or RIFLE F (Analysis C) for exemplary 3-Marker Panels.

| Panel | Analysis B | | | | Analysis C | | | | Analysis E | | | |
|---|---|---|---|---|---|---|---|---|---|---|---|---|
| | T2 | p2 | T3 | p3 | T2 | p2 | T3 | p3 | T2 | p2 | T3 | p3 |
| Hyaluronic acid × Insulin-like growth factor-binding protein 7 × Metalloproteinase inhibitor 2 | 3.3 | 7.0E−02 | 11.7 | 5.4E−05 | 1.0 | 1.0E00 | 14.0 | 1.1E−02 | 2.5 | 2.8E−01 | 12.4 | 7.6E−04 |

Collection time is 24 hr prior to RIFLE I for Analysis B and C. Collection time is at enrollment for Analysis E, and subjects at RIFLE stage I or F at enrollment were excluded. T2, p2, T3, and p3 are the relative risk and corresponding p value for the second and third tertile (relative to the first tertile), respsectively.

Example 6. Kidney Injury Markers for Evaluating Mortality Risk in Patients

Patients from the intensive care unit (ICU) were enrolled in the following study. Each patient was classified by kidney status as non-injury (0), risk of injury (R), injury (I), and failure (F) according to the maximum stage reached within 48 hours of enrollment as determined by the RIFLE criteria. EDTA anti-coagulated blood samples (10 mL) and a urine samples (25-30 mL) were collected from each patient at the time of enrollment into the study. Markers were each measured by standard immunoassay methods using commercially available assay reagents in the urine samples and the plasma component of the blood samples collected.

The individual marker assay results obtained from the enrollment sample were combined to provide a single result as indicated herein, and the single result treated as an individual biomarker using standard statistical methods. In expressing these combinations, the arithmetic operators such as "×" (multiplication) and "/" (division) are used in their ordinary mathematical sense. The patient population was segregated based on the panel results using threshold values which divided the population into thirds ("tertiles"). Patients with panel results in the lower, middle, and upper third comprise the first, second, and third tertiles, respectively. The relative risk of AKI-related mortality within 7, 14, and 28 days was calculated for the second and third tertiles, relative to a value of 1 for the first tertile, as indicated in the following table. "AKI-related mortality" or "AKI-related death" was defined as death accompanied by a minimum RIFLE stage of R.

TABLE 15

Relative risk of AKI-related death within 7, 14, and 28 days from enrollment for the third tertile compared to the first tertile of panel results.

| Panel | Relative Risk for Third Tertile ($p < 0.05$) |
|---|---|
| AKI-Related Death within 7 Days after enrollment | |
| Insulin-like growth factor-binding protein 7 × Metalloproteinase inhibitor 2 | 10.0 |
| Insulin-like growth factor-binding protein 7 × Hepatocyte growth factor | 11.0 |
| Neutrophil elastase × Serum amyloid P-component | 5.0 |
| Hyaluronic acid × Serum amyloid P-component | 5.0 |
| Neutrophil elastase × Tumor necrosis factor receptor superfamily member 11B | 9.0 |
| Hyaluronic acid × Insulin-like growth factor-binding protein 7 | 10.0 |
| Insulin-like growth factor-binding protein 7 × C-C motif chemokine 13 | 6.0 |
| Insulin-like growth factor-binding protein 7 × Immunoglobulin A | 5.0 |
| Beta-2-glycoprotein 1 × Insulin-like growth factor-binding protein 7 | 5.0 |
| Serum amyloid P-component × Insulin-like growth factor-binding protein 7 | 5.0 |
| Hyaluronic acid × Neutrophil elastase × Insulin-like growth factor-binding protein 7 | 5.0 |
| Neutrophil elastase × Insulin-like growth factor-binding protein 7 × Metalloproteinase inhibitor 2 | 10.0 |
| Hyaluronic acid × Neutrophil elastase × Serum amyloid P-component | 5.0 |
| Hyaluronic acid × Neutrophil elastase × Hepatocyte growth factor | 9.0 |
| Hyaluronic acid × Insulin-like growth factor-binding protein 7 × Metalloproteinase inhibitor 2 | 5.0 |
| Hyaluronic acid × Beta-2-glycoprotein 1 × Insulin-like growth factor-binding protein 7 | 5.5 |
| Neutrophil elastase × Metalloproteinase inhibitor 2 × Hepatocyte growth factor | 5.0 |
| Neutrophil elastase × Insulin-like growth factor-binding protein 7 × C-C motif chemokine 24 | 5.5 |
| Neutrophil elastase × Serum amyloid P-component/(Alpha-1 antitrypsin) | 5.0 |
| AKI-Related Death within 14 Days after enrollment | |
| Insulin-like growth factor-binding protein 7 × Metalloproteinase inhibitor 2 | 6.0 |
| Neutrophil elastase × Insulin-like growth factor-binding protein 7 | 6.0 |
| Neutrophil elastase × Metalloproteinase inhibitor 2 | 6.0 |
| Insulin-like growth factor-binding protein 7 × Hepatocyte growth factor | 7.0 |
| Neutrophil elastase × Serum amyloid P-component | 7.0 |
| Hyaluronic acid × Serum amyloid P-component | 5.5 |
| Hyaluronic acid × Neutrophil elastase | 4.0 |
| Neutrophil elastase × Hepatocyte growth factor | 5.5 |
| Neutrophil elastase × Tumor necrosis factor receptor superfamily member 11B | 12.0 |
| Hyaluronic acid × Insulin-like growth factor-binding protein 7 | 12.0 |
| Insulin-like growth factor-binding protein 7 × C-C motif chemokine 13 | 7.0 |
| Insulin-like growth factor-binding protein 7 × Immunoglobulin A | 4.3 |

TABLE 15-continued

Relative risk of AKI-related death within 7, 14, and 28 days from enrollment for the third tertile compared to the first tertile of panel results.

| Panel | Relative Risk for Third Tertile ($p < 0.05$) |
|---|---|
| Insulin-like growth factor-binding protein 7 × C-X-C motif chemokines (−1, −2, −3) | 5.5 |
| Beta-2-glycoprotein 1 × Insulin-like growth factor-binding protein 7 | 6.0 |
| Serum amyloid P-component × Insulin-like growth factor-binding protein 7 | 6.0 |
| Beta-2-glycoprotein 1 × Metalloproteinase inhibitor 2/(Alpha-1 antitrypsin) | 3.7 |
| AKI-Related Death within 7 Days after enrollment | |
| Beta-2-glycoprotein 1 × Hyaluronic acid/(Alpha-1 antitrypsin) | 5.0 |
| Beta-2-glycoprotein 1 × Insulin-like growth factor-binding protein 7/(Alpha-1 antitrypsin) | 5.0 |
| Hyaluronic acid × Neutrophil elastase × Insulin-like growth factor-binding protein 7 | 6.5 |
| Neutrophil elastase × Insulin-like growth factor-binding protein 7 × Metalloproteinase inhibitor 2 | 13.0 |
| Hyaluronic acid × Neutrophil elastase × Serum amyloid P-component | 6.0 |
| Hyaluronic acid × Immunoglobulin A/(Alpha-1 antitrypsin) | 3.7 |
| Hyaluronic acid × Neutrophil elastase/(Alpha-1 antitrypsin) | 4.0 |
| Hyaluronic acid × Neutrophil elastase × Hepatocyte growth factor | 11.0 |
| Hyaluronic acid × Neutrophil elastase × Cathepsin D | 6.5 |
| Hyaluronic acid × Neutrophil elastase × Metalloproteinase inhibitor 2 | 4.0 |
| Hyaluronic acid × Insulin-like growth factor-binding protein 7 × Metalloproteinase inhibitor 2 | 6.0 |
| Hyaluronic acid × Beta-2-glycoprotein 1 × Insulin-like growth factor-binding protein 7 | 6.5 |
| Neutrophil elastase × Hepatocyte growth factor/(Alpha-1 antitrypsin) | 4.3 |
| Neutrophil elastase × Metalloproteinase inhibitor 2 × Hepatocyte growth factor | 6.5 |
| Neutrophil elastase × Metalloproteinase inhibitor 2/(Alpha-1 antitrypsin) | 3.7 |
| Neutrophil elastase × Insulin-like growth factor-binding protein 7 × Cathepsin D | 4.0 |
| Neutrophil elastase × Tumor necrosis factor receptor superfamily member 11B/(Alpha-1 antitrypsin) | 3.3 |
| Neutrophil elastase × Insulin-like growth factor-binding protein 7/(Alpha-1 antitrypsin) | 4.7 |
| Neutrophil elastase × Insulin-like growth factor-binding protein 7 × Hepatocyte growth factor | 4.3 |
| Neutrophil elastase × Insulin-like growth factor-binding protein 7 × C-C motif chemokine 24 | 7.0 |
| Neutrophil elastase × Cathepsin D × Metalloproteinase inhibitor 2 | 4.0 |
| Neutrophil elastase × Serum amyloid P-component/(Alpha-1 antitrypsin) | 7.0 |
| AKI-Related Death within 28 Days after enrollment | |
| Insulin-like growth factor-binding protein 7 × Metalloproteinase inhibitor 2 | 4.3 |
| Neutrophil elastase × Insulin-like growth factor-binding protein 7 | 4.3 |
| Neutrophil elastase × Metalloproteinase inhibitor 2 | 4.3 |
| Insulin-like growth factor-binding protein 7 × Hepatocyte growth factor | 5.0 |
| Neutrophil elastase × Serum amyloid P-component | 4.7 |
| Hyaluronic acid × Serum amyloid P-component | 3.7 |
| Hyaluronic acid × Neutrophil elastase | 3.3 |
| Neutrophil elastase × Hepatocyte growth factor | 4.0 |
| Neutrophil elastase × Tumor necrosis factor receptor superfamily member 11B | 6.5 |
| Hyaluronic acid × Insulin-like growth factor-binding protein 7 | 6.5 |
| AKI-Related Death within 7 Days after enrollment | |
| Insulin-like growth factor-binding protein 7 × C-C motif chemokine 13 | 5.0 |
| Insulin-like growth factor-binding protein 7 × Immunoglobulin A | 3.3 |
| Insulin-like growth factor-binding protein 7 × C-X-C motif chemokines (−1, −2, −3) | 4.0 |
| Beta-2-glycoprotein 1 × Insulin-like growth factor-binding protein 7 | 4.0 |
| Serum amyloid P-component × Insulin-like growth factor-binding protein 7 | 4.0 |
| Beta-2-glycoprotein 1 × Hyaluronic acid/(Alpha-1 antitrypsin) | 3.7 |
| Beta-2-glycoprotein 1 × Insulin-like growth factor-binding protein 7/(Alpha-1 antitrypsin) | 3.7 |
| Hyaluronic acid × Neutrophil elastase × Insulin-like growth factor-binding protein 7 | 4.7 |
| Neutrophil elastase × Insulin-like growth factor-binding protein 7 × Metalloproteinase inhibitor 2 | 7.0 |
| Hyaluronic acid × Neutrophil elastase × Serum amyloid P-component | 4.3 |
| Hyaluronic acid × Neutrophil elastase/(Alpha-1 antitrypsin) | 3.3 |
| Hyaluronic acid × Neutrophil elastase × Hepatocyte growth factor | 6.0 |
| Hyaluronic acid × Neutrophil elastase × Cathepsin D | 4.7 |
| Hyaluronic acid × Neutrophil elastase × Metalloproteinase inhibitor 2 | 3.3 |
| Hyaluronic acid × Insulin-like growth factor-binding protein 7 × Metalloproteinase inhibitor 2 | 4.3 |
| Hyaluronic acid × Beta-2-glycoprotein 1 × Insulin-like growth factor-binding protein 7 | 4.7 |
| Neutrophil elastase × Hepatocyte growth factor/(Alpha-1 antitrypsin) | 3.5 |
| Neutrophil elastase × Metalloproteinase inhibitor 2 × Hepatocyte growth factor | 4.7 |
| Neutrophil elastase × Insulin-like growth factor-binding protein 7 × Cathepsin D | 3.3 |
| Neutrophil elastase × Tumor necrosis factor receptor superfamily member 11B/(Alpha-1 antitrypsin) | 2.8 |
| Neutrophil elastase × Insulin-like growth factor-binding protein 7/(Alpha-1 antitrypsin) | 3.8 |
| Neutrophil elastase × Insulin-like growth factor-binding protein 7 × Hepatocyte growth factor | 3.5 |
| Neutrophil elastase × Insulin-like growth factor-binding protein 7 × C-C motif chemokine 24 | 5.0 |
| Neutrophil elastase × Cathepsin D × Metalloproteinase inhibitor 2 | 3.3 |
| Neutrophil elastase × Serum amyloid P-component/(Alpha-1 antitrypsin) | 5.0 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of treating a subject having an increased risk of experiencing a detrimental outcome related to a renal injury, the method comprising:
   correlating an assay result measuring levels of kidney injury markers in one or more body fluid samples obtained from the subject to an increased risk of experiencing a detrimental outcome related to a renal injury when the assay result is above a predetermined threshold, wherein the kidney injury markers comprise Insulin-like growth factor-binding protein 7 (IGFB7) and Metalloproteinase inhibitor 2 (TIMP2) and the assay result combines the levels of the kidney injury markers into a single composite result;
   treating the subject having an increased risk of experiencing a detrimental outcome related to a renal injury with a compatible treatment, wherein the compatible treatment comprises one or more of initiating renal replacement therapy, withdrawing delivery of compounds that are known to be damaging to the kidney, delaying procedures that are known to be damaging to the kidney and modifying diuretic administration.

2. The method of claim 1, wherein the risk of experiencing a detrimental outcome related to a renal injury comprises a risk of needing renal replacement therapy, a risk of requiring withdrawal of renal toxins, a risk of progressing to a worsening stage of AKI, a risk of end stage renal disease, a risk of a major adverse cardiac event, a risk of developing chronic kidney disease, or a risk of death.

3. The method of claim 1, wherein the subject has been staged as not having acute kidney injury.

4. The method of claim 1, wherein the subject has been staged as having RIFLE stage R or AKIN stage I acute kidney injury.

5. The method of claim 4, wherein the subject meets only the serum creatinine criteria of RIFLE stage R or AKIN stage I acute kidney injury.

6. The method of claim 4, wherein the subject meets only the urine output criteria of RIFLE stage R or AKIN stage I acute kidney injury.

7. The method of claim 4, wherein the subject meets both the serum creatinine and the urine output criteria of RIFLE stage R or AKIN stage I acute kidney injury.

8. The method of claim 1, wherein the subject has been staged as having RIFLE stage I or AKIN stage II acute kidney injury.

9. The method of claim 8, wherein the subject meets only the serum creatinine criteria of RIFLE stage I or AKIN stage II acute kidney injury.

10. The method of claim 8, wherein the subject meets only the urine output criteria of RIFLE stage I or AKIN stage II acute kidney injury.

11. The method of claim 8, wherein the subject meets both the serum creatinine and the urine output criteria of RIFLE stage I or AKIN stage II acute kidney injury.

12. The method of claim 1, wherein the subject has been staged as having RIFLE stage F or AKIN stage III acute kidney injury.

13. The method of claim 12, wherein the subject meets only the serum creatinine criteria of RIFLE stage F or AKIN stage III acute kidney injury.

14. The method of claim 12, wherein the subject meets only the urine output criteria of RIFLE stage F or AKIN stage III acute kidney injury.

15. The method of claim 12, wherein the subject meets both the serum creatinine and the urine output criteria of RIFLE stage F or AKIN stage III acute kidney injury.

16. The method of claim 1, wherein the single composite result is a concentration of IFGBP7multiplied by a concentration of TIMP2.

17. The method of claim 1, wherein the body fluid sample is a urine sample.

18. The method of claim 1, wherein the risk of experiencing a detrimental outcome related to a renal injury is a risk of experiencing the detrimental outcome within 7 days.

19. The method of claim 1, wherein the subject is selected for evaluation based on the pre-existence in the subject of one or more known risk factors for prerenal, intrinsic renal, or post renal acute kidney injury.

20. The method of claim 1, wherein the subject is selected for evaluation based on an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, aneurism, chronic lung disease, acute lung injury, HIV infection, volume depletion, hypotension, shock, sepsis, injury to renal function, reduced renal function, or acute kidney injury; or based on undergoing or having undergone major vascular surgery, coronary artery bypass, or other cardiac surgery; or based on previous or anticipated exposure to one or more nephrotoxic agents; or based on one or more risk scores.

* * * * *